(12) United States Patent
Zonana et al.

(10) Patent No.: US 6,355,782 B1
(45) Date of Patent: Mar. 12, 2002

(54) HYPOHIDROTIC ECTODERMAL DYPLASIA GENES AND PROTEINS

(75) Inventors: Jonathan Zonana; Betsy M. Ferguson, both of Portland, OR (US); Denis Headon; Paul Overbeek, both of Houston, TX (US)

(73) Assignees: Baylor College of Medicine, Houston, TX (US); Oregon Health & Science University, Portland, OR (US)

( * ) Notice: Subject to any disclaimer, the term of this patent is extended or adjusted under 35 U.S.C. 154(b) by 0 days.

(21) Appl. No.: 09/342,681

(22) Filed: Jun. 29, 1999

Related U.S. Application Data

(60) Provisional application No. 60/112,366, filed on Dec. 15, 1998, and provisional application No. 60/092,279, filed on Jul. 9, 1998.

(51) Int. Cl.[7] ........................ C07K 14/00; C07K 14/475
(52) U.S. Cl. ........................ 530/399; 530/350
(58) Field of Search ....................... 514/2, 44; 530/350, 530/399

(56) References Cited

U.S. PATENT DOCUMENTS

| 5,556,786 A | 9/1996 | Kere et al. |
| 5,700,926 A | 12/1997 | Kere et al. |

OTHER PUBLICATIONS

Pakula, et al., 1989. Annual Review of Genetics, vol. 23,pp. 289–310.*

Ezer, S. et al.: "Anhidrotic ectodermal dysplasia (EDA) protein expressed in MCF–7 cells associates with cell membrane and induces rounding" Hum. Molec. Genetics, 1997, 6:1581–1587.

Ferguson, B. et al.: "Cloning of Tabby, the murine homolog of the human EDA gene: evidence for a membrane–associated protein with a short collagenous domain" Hum. Molec. Genetics, 1997, 6: 1589–1594.

GenBank Accession No. AF004435.

Kere, J. et al.: "X–Linked anhidrotic (hypohidrotic) ectodermal dysplasia is caused by mutation in a novel transmembrane protein" Nature Genetics, 1996, 13:409–416.

GenBank Accession No. U59227.

Majumder, K. et al.: "YAC rescue of downless locus mutations in mice" Mammalian Genome, 1998, 9:863–868.

Srivastava, A. et al.: "The Tabby phenotype is caused by mutation in a mouse homologue of the EDA gene that reveals novel mouse and human exons and encodes a protein (ectodysplasin–A) with collagenous domains" Proc. Natl. Acad. Sci. USA, 1997, 94:13069–13074.

GenBank Accession No. AF016628.

* cited by examiner

*Primary Examiner*—Deborah Crouch
*Assistant Examiner*—Anne-Marie Baker
(74) *Attorney, Agent, or Firm*—Klarquist Sparkman, LLP

(57) ABSTRACT

The DNA and amino acid sequences are disclosed for the protein ligand (EDA1-II) and receptors (dl and DL) involved in ectodermal dysplasia. Also disclosed are variant DNA and amino acid sequences, and therapeutic applications of the ligands and receptors.

19 Claims, 8 Drawing Sheets

```
EDA    1   MGYPEVERRELLPAAAPRERGSQGCGCGGAPARAGEGNSCL|FLGFFGLSLALHLLTLCC|*****
TA         MGYPEVERREPLPAAAPRERGSQGCGCGRGAPARAGEGNSCR LFLGFFGLSLALHLLTLCC *****
           ***                                                         ***

EDA   61   YLELRSELRRERGAESRLGGSGTPGTSGTLSSLGGLDPDSPITSHLGQPSPKQQPLEPGE *****
TA         YLELRSELRRERGTESRLGGPGAPGTSGTLSSPGSLDPVGPITRHLGQPSFQQQPLEPGE *****
           ***                                                         ***

EDA  121   AALHSDSQDGHQ|M|ALLNFFFPDEKPYSEEESRRVRRNKRSKSNEGADGPVKNKKGKKAG *****
TA         DPLPPESQDRHQ|M|ALLNFFFPDEKAYSEEESRRVRRNKRSKSGEGADGPVKNKKGKKAG *****
           ***                                                         ***

EDA  181   PPGPNGPPGPPGPPGPQGPPGPQGPPGIPGIPGTT|VM|GPPGPPGPQGPPGLQGPSGAADK *****
TA         PPGPNGPPGPPGPPGPQGPPGPQGPPGIPGIPGTT|VM|GPPGPPGPQGPPGLQGPSGAADK *****
           ***                                                         ***

EDA  241   AGTRENQPAVVHLQGQGSAIQVKNDLSGGVLNDWSRITMNPKVFKLHPRSGELEVLVDGT *****
TA         TGTRENQPAVVHLQGQGSAIQVKNDLSGGVLNDWSRITMNPKVFKLHPRSGELEVLVDGT *****
           ***                                                         ***

EDA  301   YFIYSQVEVYYINFTDFASYEVVVDEKPFLQCTRSIETGKTNYNTCYTAGVCLLKARQKI *****
TA         YFIYSQVEVYYINFTDFASYEVVVDEKPFLQCTRSIETGKTNYNTCYTAGVCLLKARQKI *****
           ***                                                         ***

EDA  361   AVKMVHADISINMSKHTTFFGAIRLGEAPAS ***
TA         AVKMVHADISINMSKHTTFFGAIRLGEAPAS ***
```

FIG. 1

|       |   |   |   |   |   |   |   |   |   |   |   |   |   |   |
|-------|---|---|---|---|---|---|---|---|---|---|---|---|---|---|
| EDA   | L | E | V | L | V | D | G | T | Y | F | I | Y | S | Q | V | E | V |
| HuTNF | L | V | V | P | S | E | G | L | Y | L | I | Y | S | Q | V | L | F |
| CD40L | L | T | V | K | R | Q | G | L | Y | Y | I | Y | A | Q | V | T | F |
| LTα   | L | L | V | P | T | S | G | I | Y | F | V | Y | S | Q | V | V | F |
| LTβ   | L | A | L | P | Q | D | G | L | Y | Y | L | Y | C | L | V | G | Y |
| FAS   | L | V | I | N | E | A | G | L | Y | F | V | Y | S | K | V | Y | F |
| CD40L | L | T | V | K | R | Q | G | L | Y | Y | I | Y | A | Q | V | T | F |

FIG. 4

```
DL    1    MAHVGDCTQT  PWLPVLVVSL  MCSARAEYS N CGENEYYNQT  TGLCQECPPC
           ::::::::    ::::::::::  :::::.::  : ::::::  :::  ::::::::::
dl    1    MAHVGDCKWM  SWLPVLVVSL  MCSAKAEDS N CGENEYHNQT  TGLCQQCPPC

DL   51    GPGEEPYLSC  GYGTKDEDYG  C VPCPAEKFS  KGGYQICRRH  KDCEGFFRAT
           ::::::.::   ::::::.:::  : :::::::::  ::::::::::  :::::::::
dl   51    RPGEEPYMSC  GYGTKDDDYG  C VPCPAEKFS  KGGYQICRRH  KDCEGRRRAT

Dl  101    VLTPGDMEND  AECGPCLPGY  YMLENRPRNI  YGMVCYSCLL  APPNTKECVG
           ::::::::::  ::::::::::  ::::::::::  ::::::::::  ::::::::::
dl  101    VLTPGDMEND  AECGPCLPGY  YMLENRPRNI  YGMVCYSCLL  APPNTKECVG

DL  151    ATSGASANFP  GTSGSSTLSP  FQHAHKELSG  QGHLATALII  AMSTIFIMAI
           ::::  ::.   :::  :::::  ::::::::::  ::::::::::  ::::::::::
dl  151    ATSGVSAHSS  STSGGSTLSP  FQHAHKELSG  QGHLATALII  AMSTIFIMAI

DL  201    AIVLIIMFYI  LKTKPSAPAC  CTSHPGKSVE  AQVSKDEEKK  EAPDNVVMFS
           ::::::::::  .:::::::::  :::  ::::   :: :   ::::  ::::::..  :
dl  201    AIVLIIMFYI  MKTKPSAPAC  CSSPPGKSAE  APANTHEEKK  EAPDSVVTFP

DL  251    EKDEFEKLTA  TSAKPTKSEN  DASSENEQLL  SRSVDSDEEP  APDKQGSPEL
           :   ::.:::  :   ::::   ::::::::::  ::::::::::  ::::::::::
dl  251    ENGEFQKLTA  TPTKTPKSEN  DASSENEQLL  SRSVDSDEEP  APDKQGSPEL

DL  301    CLLSLVHLAR  EKSATSNKSA  GIQSRRKKIL  DVYANVCGVV  EGLSPTELPF
           ::::::::::  :::  ::::::  ::::::::::  ::::::::::  ::::::::::
dl  301    CLLSLVHLAR  EKSVTSNKSA  GIQSRRKKIL  DVYANVCGVV  EGLSPTELPF

DL  351    DCLEKTSRML  SSTYNSEKAV  VKTWRHLAES  FGLKRDEIGG  MTDGMQLFDR
           ::::::::::  ::::::::::  ::::::::::  ::::::::::  ::::::::::
dl  351    DCLEKTSRML  SSTYNSEKAV  VKTWRHLAES  FGLKRDEIGG  MTDGMQLFDR

DL  401    ISTAGYSIP E  LLTKLVQIER  LDAVESLCAD  I LEWAGVVPP  ASQPHAAS
           ::::::::::  ::::::::::  ::::::::::  ::::::::  ::  :  ::::
dl  401    ISTAGYSIP E  LLTKLVQIER  LDAVESLCAD  I LEWAGVVPP  ASPPPAAS
```

FIG. 7

SEQUENCE LISTING

<160> NUMBER OF SEQ ID NOS: 123

<210> SEQ ID NO 1
<211> LENGTH: 1574
<212> TYPE: DNA
<213> ORGANISM: Homo sapiens
<220> FEATURE:
<221> NAME/KEY: CDS
<222> LOCATION: (242)..(1417)

<400> SEQUENCE: 1

```
attccctcgg cgggccagcc tccctctct cccgccctc ctcctccctt tcccacccct      60
cggagtagag ctgcacatgc ggctgctccc tgctccgtcc cgcccagcca ctgtcgcgca     120
ggaacgggtc cctgcagccc ccagccgatg gcaggacagt agccgcctgt cagaggtcgt     180
gaacggctga ggcagacgca gcggctcccg ggcctcaaga gagtgggtgt ctccggaggc     240 c atg ggc tac ccg gag gtg gag cgc agg gaa ctc ctg cct gca gca gcg     289
  Met Gly Tyr Pro Glu Val Glu Arg Arg Glu Leu Leu Pro Ala Ala Ala
   1               5                  10                  15 ccg cgg gag cga ggg agc cag ggc tgc ggg tgt ggc ggg gcc cct gcc       337
Pro Arg Glu Arg Gly Ser Gln Gly Cys Gly Cys Gly Gly Ala Pro Ala
                20                  25                  30 cgg gcg ggc gaa ggg aac agc tgc ctg ctc ttc ctg ggt ttc ttt ggc       385
Arg Ala Gly Glu Gly Asn Ser Cys Leu Leu Phe Leu Gly Phe Phe Gly
            35                  40                  45 ctc tcg ctg gcc ctc cac ctg ctg acg ttg tgc tgc tac cta gag ttg       433
Leu Ser Leu Ala Leu His Leu Leu Thr Leu Cys Cys Tyr Leu Glu Leu
        50                  55                  60 cgc tcg gag ttg cgg cgg gaa cgt gga gcc gag tcc cgc ctt ggc ggc       481
Arg Ser Glu Leu Arg Arg Glu Arg Gly Ala Glu Ser Arg Leu Gly Gly
    65                  70                  75                  80 tcg ggc acc cct ggc acc tct ggc acc cta agc agc ctc ggt ggc ctc       529
Ser Gly Thr Pro Gly Thr Ser Gly Thr Leu Ser Ser Leu Gly Gly Leu
                85                  90                  95 gac cct gac agc ccc atc acc agt cac ctt ggg cag ccg tca cct aag       577
Asp Pro Asp Ser Pro Ile Thr Ser His Leu Gly Gln Pro Ser Pro Lys
            100                 105                 110 cag cag cca ttg gaa ccg gga gaa gcc gca ctc cac tct gac tcc cag       625
Gln Gln Pro Leu Glu Pro Gly Glu Ala Ala Leu His Ser Asp Ser Gln
        115                 120                 125 gac ggg cac cag atg gcc cta ttg aat ttc ttc ttc cct gat gaa aag       673
Asp Gly His Gln Met Ala Leu Leu Asn Phe Phe Phe Pro Asp Glu Lys
    130                 135                 140 cca tac tct gaa gaa gaa agt agg cgt gtt cgc cgc aat aaa aga agc       721
Pro Tyr Ser Glu Glu Glu Ser Arg Arg Val Arg Arg Asn Lys Arg Ser
145                 150                 155                 160 aaa agc aat gaa gga gca gat ggc cca gtt aaa aac aag aaa aag gga       769
```

```
                 Lys Ser Asn Glu Gly Ala Asp Gly Pro Val Lys Asn Lys Lys Gly
                             165                 170                 175 aag aaa gca gga cct cct gga ccc aat ggc cct cca gga ccc cca gga             817
Lys Lys Ala Gly Pro Pro Gly Pro Asn Gly Pro Pro Gly Pro Pro Gly
            180                 185                 190 cct cca gga ccc cag gga ccc cca gga att cca ggg att cct gga att             865
Pro Pro Gly Pro Gln Gly Pro Pro Gly Ile Pro Gly Ile Pro Gly Ile
        195                 200                 205 cca gga aca act gtt atg gga cca cct ggt cct cca ggt cct cct ggt             913
Pro Gly Thr Thr Val Met Gly Pro Pro Gly Pro Pro Gly Pro Pro Gly
    210                 215                 220 cct caa gga ccc cct ggc ctc cag gga cct tct ggt gct gct gat aaa             961
Pro Gln Gly Pro Pro Gly Leu Gln Gly Pro Ser Gly Ala Ala Asp Lys
225                 230                 235                 240 gct gga act cga gaa aac cag cca gct gtg gtg cat cta cag ggc caa            1009
Ala Gly Thr Arg Glu Asn Gln Pro Ala Val Val His Leu Gln Gly Gln
                245                 250                 255 ggg tca gca att caa gtc aag aat gat ctt tca ggt gga gtg ctc aat            1057
Gly Ser Ala Ile Gln Val Lys Asn Asp Leu Ser Gly Gly Val Leu Asn
            260                 265                 270 gac tgg tct cgc atc act atg aac ccc aag gtg ttt aag cta cat ccc            1105
Asp Trp Ser Arg Ile Thr Met Asn Pro Lys Val Phe Lys Leu His Pro
        275                 280                 285 cgc agc ggg gag ctg gag gta ctg gtg gac ggc acc tac ttc atc tat            1153
Arg Ser Gly Glu Leu Glu Val Leu Val Asp Gly Thr Tyr Phe Ile Tyr
    290                 295                 300 agt cag gta gaa gta tac tac atc aac ttc act gac ttt gcc agc tat            1201
Ser Gln Val Glu Val Tyr Tyr Ile Asn Phe Thr Asp Phe Ala Ser Tyr
305                 310                 315                 320 gag gtg gtg gtg gat gag aag ccc ttc ctg cag tgc aca cgc agc atc            1249
Glu Val Val Val Asp Glu Lys Pro Phe Leu Gln Cys Thr Arg Ser Ile
                325                 330                 335 gag acg ggc aag acc aac tac aac act tgc tat acc gca ggc gtc tgc            1297
Glu Thr Gly Lys Thr Asn Tyr Asn Thr Cys Tyr Thr Ala Gly Val Cys
            340                 345                 350 ctc ctc aag gcc cgg cag aag atc gcc gtc aag atg gtg cac gct gac            1345
Leu Leu Lys Ala Arg Gln Lys Ile Ala Val Lys Met Val His Ala Asp
        355                 360                 365 atc tcc atc aac atg agc aag cac acc acg ttc ttt ggg gcc atc agg            1393
Ile Ser Ile Asn Met Ser Lys His Thr Thr Phe Phe Gly Ala Ile Arg
    370                 375                 380 ctg ggt gaa gcc cct gca tcc tag attcccccat tttgcctctg tccgtgcccc           1447
Leu Gly Glu Ala Pro Ala Ser
385                 390 ttccctgggt ttgggagcca ggactcccaa aacctctaag tgctgctgtg gagtgaggtg         1507
tattggtgtt gcagccgcag agaaatgccc cattgttatt tattccccag tgactccagg         1567
gtgacaa                                                                    1574

<210> SEQ ID NO 2
<211> LENGTH: 391
<212> TYPE: PRT
<213> ORGANISM: Homo sapiens

<400> SEQUENCE: 2

Met Gly Tyr Pro Glu Val Glu Arg Arg Glu Leu Leu Pro Ala Ala Ala
  1               5                  10                  15

Pro Arg Glu Arg Gly Ser Gln Gly Cys Gly Cys Gly Gly Ala Pro Ala
             20                  25                  30
```

```
Arg Ala Gly Glu Gly Asn Ser Cys Leu Leu Phe Leu Gly Phe Phe Gly
             35                  40                  45

Leu Ser Leu Ala Leu His Leu Leu Thr Leu Cys Cys Tyr Leu Glu Leu
 50                  55                  60

Arg Ser Glu Leu Arg Arg Glu Arg Gly Ala Glu Ser Arg Leu Gly Gly
 65                  70                  75                  80

Ser Gly Thr Pro Gly Thr Ser Gly Thr Leu Ser Ser Leu Gly Gly Leu
                 85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Pro Asp Glu Lys
    130                 135                 140

Pro Tyr Ser Glu Glu Ser Arg Arg Val Arg Arg Asn Lys Arg Ser
145                 150                 155                 160

Lys Ser Asn Glu Gly Ala Asp Gly Pro Val Lys Asn Lys Lys Gly
                165                 170                 175

Lys Lys Ala Gly Pro Pro Gly Pro Asn Gly Pro Gly Pro Pro Gly
                180                 185                 190

Pro Pro Gly Pro Gln Gly Pro Pro Gly Ile Pro Gly Ile Pro Gly Ile
            195                 200                 205

Pro Gly Thr Thr Val Met Gly Pro Pro Gly Pro Pro Gly Pro Pro Gly
            210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
            275                 280                 285

Arg Ser Gly Glu Leu Glu Val Leu Val Asp Gly Thr Tyr Phe Ile Tyr
290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
                340                 345                 350

Leu Leu Lys Ala Arg Gln Lys Ile Ala Val Lys Met Val His Ala Asp
            355                 360                 365

Ile Ser Ile Asn Met Ser Lys His Thr Thr Phe Phe Gly Ala Ile Arg
            370                 375                 380

Leu Gly Glu Ala Pro Ala Ser
385                 390

<210> SEQ ID NO 3
<211> LENGTH: 1661
<212> TYPE: DNA
<213> ORGANISM: Mus musculus
<220> FEATURE:
<221> NAME/KEY: CDS
<222> LOCATION: (142)..(1275)

<400> SEQUENCE: 3
```

-continued

```
tcaggaacgg gtccctgcag cccccagccg atggcaggac agtagtcgcc tgtcagggt        60 cgtgaaggac tgaggcagag gcagaggctc ccggagaggc agaggctccc gggcctcaga      120
tagtggttgt ctctggaggc c atg ggc tac cca gag gta gag cgc agg gaa        171
                         Met Gly Tyr Pro Glu Val Glu Arg Arg Glu
                          1               5                  10 ccc ctg cct gcg gca gcg cca agg gag cgg ggc agc cag ggc tgc ggc        219
Pro Leu Pro Ala Ala Ala Pro Arg Glu Arg Gly Ser Gln Gly Cys Gly
                 15                  20                  25 tgt cgc ggg gcc cct gct cgg gcg ggc gaa ggg aac agc tgc cgg ctc        267
Cys Arg Gly Ala Pro Ala Arg Ala Gly Glu Gly Asn Ser Cys Arg Leu
             30                  35                  40 ttc ctg ggt ttc ttt ggc ctc tcg ctg gcc ctc cac ctg ctg acg ctg        315
Phe Leu Gly Phe Phe Gly Leu Ser Leu Ala Leu His Leu Leu Thr Leu
         45                  50                  55 tgc tgc tac cta gag ttg cgg tcc gaa ttg cgg cgg gaa cgg gga acc        363
Cys Cys Tyr Leu Glu Leu Arg Ser Glu Leu Arg Arg Glu Arg Gly Thr
     60                  65                  70 gag tcc cgc ctc ggt ggc ccg ggt gct cct ggc acc tct ggc acc cta        411
Glu Ser Arg Leu Gly Gly Pro Gly Ala Pro Gly Thr Ser Gly Thr Leu
 75                  80                  85                  90 agc agc cct ggg agc ctc gac ccg gtg ggt ccc atc acc cgc cac ctg        459
Ser Ser Pro Gly Ser Leu Asp Pro Val Gly Pro Ile Thr Arg His Leu
                 95                 100                 105 ggg cag ccg tcc ttt caa cag cag cct ttg gaa ccg gga gaa gat cca        507
Gly Gln Pro Ser Phe Gln Gln Gln Pro Leu Glu Pro Gly Glu Asp Pro
            110                 115                 120 ctc ccc cct gag tcc cag gac cgg cac cag atg gcc ctc ctg aat ttc        555
Leu Pro Pro Glu Ser Gln Asp Arg His Gln Met Ala Leu Leu Asn Phe
        125                 130                 135 ttc ttt cct gat gaa aag gca tat tct gaa gag gaa agt agg cgt gtt        603
Phe Phe Pro Asp Glu Lys Ala Tyr Ser Glu Glu Glu Ser Arg Arg Val
    140                 145                 150 cgc cgc aat aag aga agc aaa agt ggt gaa gga gca gat ggt cct gtt        651
Arg Arg Asn Lys Arg Ser Lys Ser Gly Glu Gly Ala Asp Gly Pro Val
155                 160                 165                 170 aaa aac aag aaa aag gga aag aag gca ggg cca cct ggg ccc aac ggc        699
Lys Asn Lys Lys Lys Gly Lys Lys Ala Gly Pro Pro Gly Pro Asn Gly
                175                 180                 185 ccc cca gga cct cca gga cct ccg gga ccc cag gga cct cca ggg att        747
Pro Pro Gly Pro Pro Gly Pro Pro Gly Pro Gln Gly Pro Pro Gly Ile
            190                 195                 200 cca gga att cct ggg att cca gga aca act gtt atg gga cca cct ggc        795
Pro Gly Ile Pro Gly Ile Pro Gly Thr Thr Val Met Gly Pro Pro Gly
        205                 210                 215 cca cct ggc cct cct ggt cct caa gga ccc cct ggc ctc caa gga cct        843
Pro Pro Gly Pro Pro Gly Pro Gln Gly Pro Pro Gly Leu Gln Gly Pro
    220                 225                 230 tct ggt gct gct gat aaa act gga act cgg gaa aat cag cca gct gtg        891
Ser Gly Ala Ala Asp Lys Thr Gly Thr Arg Glu Asn Gln Pro Ala Val
235                 240                 245                 250 gtg cat ctg cag ggc caa ggg tca gca att caa gtc aaa aat gat ctt        939
Val His Leu Gln Gly Gln Gly Ser Ala Ile Gln Val Lys Asn Asp Leu
                255                 260                 265 tca ggt gga gtg ctc aat gac tgg tct cgc atc act atg aac cct aag        987
Ser Gly Gly Val Leu Asn Asp Trp Ser Arg Ile Thr Met Asn Pro Lys
            270                 275                 280 gtg ttt aaa cta cat ccc cgc agc ggg gag ctg gag gtc tac tac atc       1035
Val Phe Lys Leu His Pro Arg Ser Gly Glu Leu Glu Val Tyr Tyr Ile
```

-continued

```
                 285                    290                      295
aac ttc act gac ttt gcc agc tac gag gtg gtg gtg gat gag aag ccc     1083
Asn Phe Thr Asp Phe Ala Ser Tyr Glu Val Val Val Asp Glu Lys Pro
    300                 305                 310 ttc ctg cag tgc acc cgc agc att gag aca ggg aag acc aac tac aac     1131
Phe Leu Gln Cys Thr Arg Ser Ile Glu Thr Gly Lys Thr Asn Tyr Asn
315                 320                 325                 330 act tgc tat act gca ggc gtg tgc ctc ctc aag gcc agg cag aaa atc     1179
Thr Cys Tyr Thr Ala Gly Val Cys Leu Leu Lys Ala Arg Gln Lys Ile
                335                 340                 345 gcc gtg aag atg gtg cac gct gac atc tct atc aat atg agc aag cac     1227
Ala Val Lys Met Val His Ala Asp Ile Ser Ile Asn Met Ser Lys His
            350                 355                 360 acc acc ttc ttc ggg gcc atc agg ctg ggc gaa gcc cct gca tcc tag     1275
Thr Thr Phe Phe Gly Ala Ile Arg Leu Gly Glu Ala Pro Ala Ser
        365                 370                 375 attctcccat tccatcctgg cccatgcccc tgccccaggt ttgggagcca ggactcccag   1335
aacctctaag tgctgctgtg tgtggaatga ggtatactgg cgttgcagcc acaaagagaa   1395
atgccccatg ctatttattc cccagtgact ccaggatgac aaggcctatg tgacttccca   1455
gaaagacctt gagttgccag gacagttgac ggagccccag ggttgtcaag aagcagaacc   1515
ttcttaggct ccctgctgac tggcttatgg tgactcctca acccttaggt ccctcatcag   1575
atgtatcatt tgttgcacta aaatgaggat ccaagacagt aggccacaaa agaaaaggt    1635 gcactccaga ttctaggggt gatccg                                        1661
```

<210> SEQ ID NO 4
<211> LENGTH: 377
<212> TYPE: PRT
<213> ORGANISM: Mus musculus

<400> SEQUENCE: 4

```
Met Gly Tyr Pro Glu Val Glu Arg Arg Glu Pro Leu Pro Ala Ala Ala
 1               5                  10                  15

Pro Arg Glu Arg Gly Ser Gln Gly Cys Gly Cys Arg Gly Ala Pro Ala
            20                  25                  30

Arg Ala Gly Glu Gly Asn Ser Cys Arg Leu Phe Leu Gly Phe Phe Gly
        35                  40                  45

Leu Ser Leu Ala Leu His Leu Leu Thr Leu Cys Cys Tyr Leu Glu Leu
    50                  55                  60

Arg Ser Glu Leu Arg Arg Glu Arg Gly Thr Glu Ser Arg Leu Gly Gly
65                  70                  75                  80

Pro Gly Ala Pro Gly Thr Ser Gly Thr Leu Ser Ser Pro Gly Ser Leu
                85                  90                  95

Asp Pro Val Gly Pro Ile Thr Arg His Leu Gly Gln Pro Ser Phe Gln
            100                 105                 110

Gln Gln Pro Leu Glu Pro Gly Glu Asp Pro Leu Pro Glu Ser Gln
        115                 120                 125

Asp Arg His Gln Met Ala Leu Leu Asn Phe Phe Pro Asp Glu Lys
    130                 135                 140

Ala Tyr Ser Glu Glu Glu Ser Arg Arg Val Arg Arg Asn Lys Arg Ser
145                 150                 155                 160

Lys Ser Gly Glu Gly Ala Asp Gly Pro Val Lys Asn Lys Lys Gly
                165                 170                 175

Lys Lys Ala Gly Pro Pro Gly Pro Asn Gly Pro Pro Gly Pro Pro Gly
            180                 185                 190
```

```
Pro Pro Gly Pro Gln Gly Pro Gly Ile Pro Ile Pro Gly Ile
        195                 200                 205

Pro Gly Thr Thr Val Met Gly Pro Gly Pro Pro Gly Pro Pro Gly
        210                 215                 220

Pro Gln Gly Pro Pro Gly Leu Gln Gly Pro Ser Gly Ala Ala Asp Lys
225                 230                 235                 240

Thr Gly Thr Arg Glu Asn Gln Pro Ala Val Val His Leu Gln Gly Gln
                245                 250                 255

Gly Ser Ala Ile Gln Val Lys Asn Asp Leu Ser Gly Val Leu Asn
        260                 265                 270

Asp Trp Ser Arg Ile Thr Met Asn Pro Lys Val Phe Lys Leu His Pro
        275                 280                 285

Arg Ser Gly Glu Leu Glu Val Tyr Tyr Ile Asn Phe Thr Asp Phe Ala
        290                 295                 300

Ser Tyr Glu Val Val Asp Gly Lys Pro Phe Leu Gln Cys Thr Arg
305                 310                 315                 320

Ser Ile Glu Thr Gly Lys Thr Asn Tyr Asn Thr Cys Tyr Thr Ala Gly
                325                 330                 335

Val Cys Leu Leu Lys Ala Arg Gln Lys Ile Ala Val Lys Met Val His
        340                 345                 350

Ala Asp Ile Ser Ile Asn Met Ser Lys His Thr Thr Phe Phe Gly Ala
        355                 360                 365

Ile Arg Leu Gly Glu Ala Pro Ala Ser
        370                 375

<210> SEQ ID NO 5
<211> LENGTH: 630
<212> TYPE: DNA
<213> ORGANISM: Homo sapiens
<220> FEATURE:
<221> NAME/KEY: misc_feature
<222> LOCATION: (65)
<223> OTHER INFORMATION: n represents a, c, t, or g

<400> SEQUENCE: 5
acagtggggg ggaagatggg ctcagggttt agacacatca aacttaaggt acaggtagac        60
tgtgntatgg aaagatggtt ttttatgttg gctatgactg agtggggtca acctttgact      120
gatgtacttg taattttttac agatggccct attgaatttc ttcttccctg atgaaaagcc     180
atactctgaa gaagaaagta ggcgtgttcg ccgcaataaa agaagcaaaa gcaatgaagg       240
agcagatggt aagtctactc agttgatcct ttatcacttc tgaattattt gttagtaaaa       300
gtatcctttt aagaactacc ttcttggtag ggcatggtgg ctcacgcctg taatcctagc       360
actttgggag gcccacgcgg gcagatcact tgaggtgagg aattcaaaac cagcctggcc       420
aacatggtga accctgtctc tactaaaaaa tacaaaaaaa attagccggg cctagtccca       480
gctgcttggg agactaaggc aggagaatcg cttgaaactg ggaggtagag gttgcagtga       540
gctgagactg tgccactgca ctccagcctg ggtgacagtg cgagactcca tctcaaaaaa       600
caaaaacaaa caaaaaaaaa cactaccttt                                       630

<210> SEQ ID NO 6
<211> LENGTH: 549
<212> TYPE: DNA
<213> ORGANISM: Homo sapiens

<400> SEQUENCE: 6
```

```
acccattccc tcacccccaaa gactgaagta gagagatttt tctccctagg gaagaatctt     60
ccttgaaact tttgtggcct caggagtcag aagacagaat ggggaggttt gatagttgga    120
tccttgccaa aagcctgacc cttggctgtg agactccctc aaatttgcag tgtcttgggg    180
atccctccta gtgactatct tagaaaataa acattttctg ttcatttcca atgacttaat    240
tatctatttt attttctta taggcccagt taaaaacaag aaaaagggta agttcctgac      300
tttataaaat tgctgtcttg tcatatattt tctaaagtta gaagaaaaaa acaagagtgc    360 gattttttgta ttatattctt tcagcattgt ctgtctgtta ttttattcaa tcatatgtta   420
tcttcttgag tattgtagtt tctgaagaac aagaaatcat tcttcagtga tgattcacct    480
ctttcattct tccttgttct tctccctgcc cttctttttta ttctttttttt tttttttttt  540 tttttttt                                                             549

<210> SEQ ID NO 7
<211> LENGTH: 821
<212> TYPE: DNA
<213> ORGANISM: Homo sapiens

<400> SEQUENCE: 7
aatcccagca ttttgggagg ctgaggcagg cagatcaccc gaagtcagga gtttgagacc     60
aacctggccg acatggtgaa accccgtttt tactaaaaat acaaaaatta gcaggttgcg    120
gtggcaagcg cctgtaatcc cagttaatcc agaggctgag gcaggagaat tgcttgaacc    180
cgggaggtgg aggttgcagt gagccgagat tgtgccactg aactccagcc tgggcaacag    240
agcaggactc cgtctcaaaa aaaaagtaa cactgatcct attttttcagg aaagaaagca    300 ggacctcctg gacccaatgg ccctccagga ccccaggacc ctccaggacc caggggaccc    360
ccaggaattc cagggattcc tggaattcca ggaacaactg ttatgggacc acctggtcct    420
ccaggtcctc ctggtcctca aggaccccct ggcctccagg gaccttctgg tgagttcccc    480
tgtctctcca ccccaccagg tgcctttaaa gtactttagg agagcaggag tgggtgatcc    540
tgagagcagt ttcaaacggt ggagatgggg ttggtgtgca ataagggatg cagatctcct    600
agcccagtgt aaaactagga attggacaag ccagtagggc ctggcctgct ctagcttctt    660
atatctacca aactgtcaag gacaggccac ctgttcttgc cccatctcaa cccttctgtt    720
acaagccctc cctgactctt ggcctccctg tagtggacca gtaaaactca tatgagccag    780
agacagaggc cctggtggtt cacagggagt tccagtgggg a                         821

<210> SEQ ID NO 8
<211> LENGTH: 977
<212> TYPE: DNA
<213> ORGANISM: Homo sapiens

<400> SEQUENCE: 8
ttcacacagg gctcagcagt gttaccatgg ccacaagaga tggagttaga gatttttttt     60
caaccaatca ttccttaaat attgagcact ttctgtatac aaagagatat attgatacat    120
ggtccctttt cttatagagt ttatctccta gaggaagaga gaacaaagaa acaagatatt    180
tacaaatagc agtgggctct atgaagaaaa ttaatagaaa gggagcaaaa cactagagaa    240
gccaatgcca ttgcctcagg gtcacacagt gatgggaatg ctctctcatt gttctccatg    300
ggtgcccggt ggggcttgcc ttgggctaat attggccaga ggcaatactc agaagttttcc   360 ctgctgggtg ctgggcccac tgaagatgaa ggtcaggca ggaaacagaa ggggtgcact     420
ctgactcttc ctccagctct gagccctgga gaataaagct cagacagggc tggctgcagg    480
```

```
gagcatggct caccaccact agctgctcag gtgagggaa aaggaagtca aaagattatg      540
ccctctgatt gtcctatcct attttgcagg tgctgctgat aaagctggaa ctcgagaaaa      600
ccaggttggc tgggattgc tctcttcctg ggtaggaggg aaagccacag gctagagcca      660
cctttaaatt agcttcttat tagatttcct gagctttatt tcatgagaac accccggaga      720
ttctgacggt tttcactcac agcccctcc catctctatg aatagaaaag ctttgcccca      780
gggcatgttt ttagctaagg aaagggtgtc ttgccaggat catttttcct cattccacag      840
gagaccccag gttcaccata gccaggccca gtagtcagct gaaataagct gccagtcaga      900
cctattcacc tgagcctcca actccccaac caccccagac accttgccgg ctctcagacc      960
acctgggatc cggagct                                                    977

<210> SEQ ID NO 9
<211> LENGTH: 1048
<212> TYPE: DNA
<213> ORGANISM: Homo sapiens
<220> FEATURE:
<221> NAME/KEY: misc_feature
<222> LOCATION: (754)
<223> OTHER INFORMATION: n represents a, c, t, or g

<400> SEQUENCE: 9
cggttctcag accacctggg atccggagct gaagagttga agagtatgtc cttgaaaaac       60
agccaaccag ctccaggccc agcctagcct gggcgtctgc cttaatggcc tgaagagctc      120
ctcccagtct ttgagcttcc taatctgtct ctattggcag gttctactgc cttgccttgt      180
ctcatctcag cctcccttgc tacagctgtg tggccacagt gataaatcta cacagctgca      240
cagtgcttga cggcttgcag ggcaatttta tatccatcac ctcatttgat cttcagacat      300
ccctgtgaga gaggccagac attcttataa tccccatttt acagttaggg aaatgaggct      360
cagaggcatt acatttggtt gaggtcacat agctaggaag cggtagagct acaaaatcat      420
attaccctct agtagaaatg tagtcagtaa catcccaaga caggggagag ggatcagaat      480
tggattacaa tagaagacta gaaaccagga tggaaacatg ggactggtgg ctgagcaagc      540
agccattact catagtgact atctctatcc ttctcatcct gccagccagc tgtggtgcat      600
ctacagggcc aagggtcagc aattcaagtc aagaatggta agaatcaaaa taggctctct      660
cccaaagagg agcttctccc ctgcctcctc cccagcctcc aaataatcac ccagcctagt      720
tcctcccagg ccgctgaggt accgttggca tacnaagtca ttctttgctc catcatgccc      780
tctactggct gtcctgagca attgctggca tcaagaccag ttgctacacc caaattgctt      840
tagaatcact gatgacggag ctgaaaggga cttgagacat catctagccc aggcattctc      900
aggggatgga ggttatatca gagccaccat ggagatatgt gtagttagat taatattttc      960
acaatacaaa ttatagaaag taaaactatg taaaattaaa ttttcttgt ctgatctaca     1020 caggtgggca gacaggctgc atctctca                                       1048

<210> SEQ ID NO 10
<211> LENGTH: 831
<212> TYPE: DNA
<213> ORGANISM: Homo sapiens

<400> SEQUENCE: 10
attttgcctg tgcaggcccc ataacaacaa agaaaatagg gcagcatgcc cactctcatc       60
ctccaccggc aaattccagc taggaggtat tggttaaaga cccttccaga tgcaagggtc      120
```

-continued

| | |
|---|---|
| aagaaaggaa ggataaagac agacaggcag agcccaggag ccctgaagca ggcctggcag | 180 |
| ctgctttaca aacagaacag cttctctgct ttcaaatgct cttcttaaag tttggccttc | 240 |
| taggctaccc tggttgcact gggatagggg tggggttgt gaactccttg gtatttattt | 300 |
| tctgttgcct cgattattct gacatgtact gagtgactgc cttctctcat actgagatct | 360 |
| ttcaggtgga gtgctcaatg actggtctcg catcactatg aaccccaagg tgtttaagct | 420 |
| acatccccgc agcggggagc tggaggtact ggtggacggc acctacttca tctatagtca | 480 |
| ggtagaagtg agtacggtct taggcctaac tcttcttata tccagaatgc agatccggtg | 540 |
| caggccacat aggggcactg tggagccagc caagaccatc caatggctaa cttcctgctt | 600 |
| tgggtgaggg ggtgggggga ccgcactggg agggagttga aaggaggaaa gagagagggg | 660 |
| gccagcttct tttgttttgt tttgttttgt ttttccctac ccaaatatta ttgaaaaact | 720 |
| gtgaaaaaga ccctcccaca ccctgccatc tgattccctc ctgcagggcc tcaggcccct | 780 |
| gtttaccctc tgagctgttt ggctgcactg ccaaacttga acttggtctc a | 831 |

<210> SEQ ID NO 11
<211> LENGTH: 743
<212> TYPE: DNA
<213> ORGANISM: Homo sapiens
<220> FEATURE:
<221> NAME/KEY: misc_feature
<222> LOCATION: (302)
<223> OTHER INFORMATION: n represents a, c, t, or g

<400> SEQUENCE: 11

| | |
|---|---|
| gcttcatgtc agggctgggg caggggtggg cggggggaaca ggggcacggt gaagctgcaa | 60 |
| atagggcatg gttcttagcc ttacagagtt tgcgacaagt gtgctgttgt aagaaaagtt | 120 |
| tgctcagcca gctgagcccc atggactagg ggaagaacaa tgcctgtcac ctgtcctttc | 180 |
| ctgttggcca gctagcacgc cttcacatgg cactgcccca tccatgggt atactaacag | 240 |
| ctcatctgag aagattctgt caattcacca cagggagggc ccccaccct ctctttcctc | 300 |
| tnttccccaa tccccttcttg ttgcctctca tcaggtatac tacatcaact tcactgactt | 360 |
| tgccagctat gaggtggtgg tggatgagaa gcccttcctg cagtgcacac gcagcatcga | 420 |
| gacgggcaag accaactaca acacttgcta taccgcaggc gtctgcctcc tcaaggcccg | 480 |
| gcagaagatc gccgtcaaga tggtgcacgc tgacatctcc atcaacatga gcaagcacac | 540 |
| cacgttcttt ggggccatca ggctgggtga agccctgca tcctagattc ccccattttg | 600 |
| cctctgtccg tgccccttcc ctgggtttgg gagccaggac tcccaaaacc tctaagtgct | 660 |
| gctgtggagt gaggtgtatt ggtgttgcag ccgcagagaa atgccccatt gttatttatt | 720 |
| ccccagtgac tccagggtga caa | 743 |

<210> SEQ ID NO 12
<211> LENGTH: 3720
<212> TYPE: DNA
<213> ORGANISM: Mus musculus
<220> FEATURE:
<221> NAME/KEY: CDS
<222> LOCATION: (260)..(1606)
<221> NAME/KEY: misc_feature
<222> LOCATION: (2961)..(3673)
<223> OTHER INFORMATION: n represents a, c, t, or g

<400> SEQUENCE: 12

| | |
|---|---|
| cagtccagac cgggaacagt caagagcgag ttcccgggag cccttcaaaa tagaaagtta | 60 |
| gttgcgctgg cagcagaggt gtgcctggcc gctgtcaccc ggctggcccc aggattgtgg | 120 |

-continued

```
agctctgctt ttgagaggac accgacggac gcctgtgaag cctgcccccc atcccttacc    180
tgctcgcctt ctccgtagac ccatcttctg ctgggaaaag ctaacctcat tcgggtacca    240
ggtgtacttc aagagatc atg gcc cac gtc ggg gac tgc aaa tgg atg tcc     292
                    Met Ala His Val Gly Asp Cys Lys Trp Met Ser
                     1               5                  10 tgg ctc cca gtg ctg gtg gtg tct ctg atg tgc tca gcc aag gcg gag    340
Trp Leu Pro Val Leu Val Val Ser Leu Met Cys Ser Ala Lys Ala Glu
             15                  20                  25 gac tcc aac tgt ggt gag aac gaa tac cac aac cag act acc ggg ctg    388
Asp Ser Asn Cys Gly Glu Asn Glu Tyr His Asn Gln Thr Thr Gly Leu
                 30                  35                  40 tgc cag cag tgt cct cca tgc aga cca ggg gag gag ccc tac atg tcc    436
Cys Gln Gln Cys Pro Pro Cys Arg Pro Gly Glu Glu Pro Tyr Met Ser
         45                  50                  55 tgt gga tac ggc act aaa gac gac gac tat ggc tgt gtg ccc tgc cct    484
Cys Gly Tyr Gly Thr Lys Asp Asp Asp Tyr Gly Cys Val Pro Cys Pro
 60                  65                  70                  75 gca gag aag ttc tcc aaa gga ggt tat cag ata tgc agg cgc cac aaa    532
Ala Glu Lys Phe Ser Lys Gly Gly Tyr Gln Ile Cys Arg Arg His Lys
                 80                  85                  90 gac tgt gag ggc ttc ttc cgg gcc act gtg ctg aca cca gga gac atg    580
Asp Cys Glu Gly Phe Phe Arg Ala Thr Val Leu Thr Pro Gly Asp Met
         95                 100                 105 gaa aac gac gct gag tgt ggc cca tgt ctc cct ggc tac tac atg ctg    628
Glu Asn Asp Ala Glu Cys Gly Pro Cys Leu Pro Gly Tyr Tyr Met Leu
    110                 115                 120 gaa aac aga ccc agg aac atc tat ggc atg gtc tgc tac tcc tgt ctc    676
Glu Asn Arg Pro Arg Asn Ile Tyr Gly Met Val Cys Tyr Ser Cys Leu
125                 130                 135 ttg gca cct ccc aac acc aag gaa tgt gtg gga gcc act tct ggg gtt    724
Leu Ala Pro Pro Asn Thr Lys Glu Cys Val Gly Ala Thr Ser Gly Val
140                 145                 150                 155 tca gca cac tca tcc agc act tcc ggt ggc agc acc ttg tct ccc ttc    772
Ser Ala His Ser Ser Ser Thr Ser Gly Gly Ser Thr Leu Ser Pro Phe
                160                 165                 170 cag cat gct cac aaa gag ctc tca ggc caa gga cac ctg gcc acc gcc    820
Gln His Ala His Lys Glu Leu Ser Gly Gln Gly His Leu Ala Thr Ala
            175                 180                 185 ctg att att gcc atg tct acg atc ttc atc atg gcc att gcc atc gtc    868
Leu Ile Ile Ala Met Ser Thr Ile Phe Ile Met Ala Ile Ala Ile Val
        190                 195                 200 ctc atc atc atg ttc tac atc atg aag act aag ccg tca gct cca gcc    916
Leu Ile Ile Met Phe Tyr Ile Met Lys Thr Lys Pro Ser Ala Pro Ala
    205                 210                 215 tgc tgt agc agt ccc cca gga aag agc gca gaa gcc cca gct aac aca    964
Cys Cys Ser Ser Pro Pro Gly Lys Ser Ala Glu Ala Pro Ala Asn Thr
220                 225                 230                 235 cac gag gag aaa aaa gag gcc cca gac agt gtg gtg acg ttc cct gag   1012
His Glu Glu Lys Lys Glu Ala Pro Asp Ser Val Val Thr Phe Pro Glu
                240                 245                 250 aat ggt gag ttc cag aag ctg aca gca aca ccc aca aag acc ccc aaa   1060
Asn Gly Glu Phe Gln Lys Leu Thr Ala Thr Pro Thr Lys Thr Pro Lys
            255                 260                 265 agt gag aat gat gcc tcc tct gag aac gag cag ttg cta agt cgc agt   1108
Ser Glu Asn Asp Ala Ser Ser Glu Asn Glu Gln Leu Leu Ser Arg Ser
        270                 275                 280 gtg gac agt gat gaa gag cca gcc ccg gac aag cag ggg tcc cca gag   1156
Val Asp Ser Asp Glu Glu Pro Ala Pro Asp Lys Gln Gly Ser Pro Glu
```

```
              285                 290                 295
cta tgt ctg ctg tcg cta gtt cac ctg gcc agg gag aag tct gtg acc       1204
Leu Cys Leu Leu Ser Leu Val His Leu Ala Arg Glu Lys Ser Val Thr
300                 305                 310                 315 agt aac aag tct gct ggg atc cag agc cgg agg aaa aag ata ctg gat       1252
Ser Asn Lys Ser Ala Gly Ile Gln Ser Arg Arg Lys Lys Ile Leu Asp
                320                 325                 330 gtg tat gcc aac gtg tgt ggt gtt gtt gaa ggt ctc agc ccc acc gag       1300
Val Tyr Ala Asn Val Cys Gly Val Val Glu Gly Leu Ser Pro Thr Glu
            335                 340                 345 ttg ccg ttt gac tgc ctt gag aag aca agc cga atg ctc agc tct aca       1348
Leu Pro Phe Asp Cys Leu Glu Lys Thr Ser Arg Met Leu Ser Ser Thr
        350                 355                 360 tac aac tct gag aag gcg gtc gtg aaa aca tgg cgc cac ctt gcc gag       1396
Tyr Asn Ser Glu Lys Ala Val Val Lys Thr Trp Arg His Leu Ala Glu
    365                 370                 375 agc ttt gga ctg aag agg gat gag att ggg ggc atg act gat ggc atg       1444
Ser Phe Gly Leu Lys Arg Asp Glu Ile Gly Gly Met Thr Asp Gly Met
380                 385                 390                 395 cag ctc ttt gac cgc atc agc acc gcg ggc tac agc atc cca gag ctg       1492
Gln Leu Phe Asp Arg Ile Ser Thr Ala Gly Tyr Ser Ile Pro Glu Leu
                400                 405                 410 ctc aca aag ttg gtg cag atc gag cgg ctg gat gct gtg gag tcc ttg       1540
Leu Thr Lys Leu Val Gln Ile Glu Arg Leu Asp Ala Val Glu Ser Leu
            415                 420                 425 tgt gca gac ata ttg gag tgg gct ggg gtt gta cca cct gcc tcc cca       1588
Cys Ala Asp Ile Leu Glu Trp Ala Gly Val Val Pro Pro Ala Ser Pro
        430                 435                 440 ccc cca gct gcg tcc tga agagttgtct tggactgtct tccctgggac              1636
Pro Pro Ala Ala Ser
    445 cagctgggga tccaatgaag tcacgaccga cagctgtgag tgatgctatc agactgccaa     1696 aactcaaggc atttcctggt gggtcactgt attccttagg ctgccctaag tagttcattg     1756 agcactcaaa tgaaccaaac catgtgggaa ggacacaggt gaagaatctg atcctgtctt     1816 ttaaggaggc acttagtgag agatgggagc atggtataga ccgtgttacc aaaacatcac     1876 ctaggcaaat gaagggatgc ttttttaaaa agtagcaaaa gttataaggg tgatagagtc     1936 tcaaggggtt gaaagtggga acatcctaat gaagaaaata acttcaaggt tttagtaaaa     1996 cggttacaaa gtacaggcat cccacatcct tcatggcctc agacagagca tggtttgctg     2056 gcatgcccta tggtttcaga ggtaactcga cctgtgtttg cagtcacaca ccatggtata     2116 agccttgcag tcactagtgg aagaactcac catgtgtcac tgacatacaa ggcgtgtgtc     2176 tgtccagtca caagtgtggg cagatctggc ctccagcacc actcgcagcc acagcagtta    2236 caatgtcagg cttgtcttgc ttcaaaggga cgtgcgtcct atctagaaa ggaaatggtg     2296 acttgctcag agtttgacca tgcctgattc ctgggtgagg ctcgagtgag ttcaggcaca     2356 acatcctgag ccagtgaggg gtggtgcagc ccgagacgca gtacagagct ggggtctgag    2416 gtcctgggca ctgggagagt cattcaaagt gtctgtctcc tccagactta gcttctctta    2476 ggtgagagag gttggtattc acatctgtag tcaggaatgt tgaggctcca gtgagcgaaa    2536 gggtgagtga agaacacgg aggcagaaga gaagaggcca gaggagcctc catggggtaa     2596 atacagtgtg ggtggccaca aaaaatgaga gtcaagggaa acgcagccgc cattctcata    2656 taagggcaac tgtaggactg agcgtttaca gggcttataa acagccattg ctcttggcat    2716 attctcttac tgcacctgta actgccagga aatgggagcc aaggaaactt ccccggcagg    2776
```

```
gggttaatgc caagctggct gctgggctcc ctcccagagc gctgactgca gagaatgctt    2836
cctttcagta aagctctggt ttagaaggcg gttgggtttt tttgttttac aaggcctatg    2896
actgaacaaa ggctttggag agcaatcagt ggtgtgttta aaaccatcaa gccatttccc    2956
accantgaat atagaccata ctgtgagagg accataatta ggtcctgaat ttttaatatg    3016
atcattttcc tgtgtctgtc tgtgcagtgt ttttttttttt tttttttaaag aaggcattta   3076 ctccattttg caagttaaat gtctgcttaa ttgtcctttt aattcctgag accctgcagt    3136
gtcccttacc cctggtcttc cataatgacg ctgcgattcc ccttaattag acttgtaaat    3196
gtcatgcgtg atgagtgagc aggtcgagga cagcaggctc ttctccaact gtcattgtgc    3256
tgaagaatgg gcagctgcag ccagcggtgt gggctgccct ccattcacac taataggttt    3316
caaggcctga ggcagccagc atccttgttg tttcctagac tccctgcttg ctgctttagg    3376
ggagccagtt cccttgtcat ttaattaaca tggcaataaa ttctggnagg gttggttggc    3436
ttcagtgtgc tttgccaacc aacaagacca cagtgacttt tggtgaccaa tggtggaact    3496
ccacgctgcc atgtttgttt ggagactgtt attatttttt cagtaattaa aggtatttag    3556
taaacaccca agctaggttt gagggcctga gccagtgaag ttttaattgt gaatattttta   3616 tataattttg tttatgtaaa ttattatatt tttataagct caataaacat attgataaaa    3676
agggaaaaaa aaaaaaaaaa aaaaaaaaa aaaaaaaaa aaaa                       3720

<210> SEQ ID NO 13
<211> LENGTH: 1347
<212> TYPE: DNA
<213> ORGANISM: Mus musculus
<220> FEATURE:
<221> NAME/KEY: CDS
<222> LOCATION: (1)..(1347)

<400> SEQUENCE: 13 atg gcc cac gtc ggg gac tgc aaa tgg atg tcc tgg ctc cca gtg ctg      48
Met Ala His Val Gly Asp Cys Lys Trp Met Ser Trp Leu Pro Val Leu
 1               5                  10                  15 gtg gtg tct ctg atg tgc tca gcc aag gcg gag gac tcc aac tgt ggt      96
Val Val Ser Leu Met Cys Ser Ala Lys Ala Glu Asp Ser Asn Cys Gly
             20                  25                  30 gag aac gaa tac cac aac cag act acc ggg ctg tgc cag cag tgt cct     144
Glu Asn Glu Tyr His Asn Gln Thr Thr Gly Leu Cys Gln Gln Cys Pro
         35                  40                  45 cca tgc aga cca ggg gag gag ccc tac atg tcc tgt gga tac ggc act     192
Pro Cys Arg Pro Gly Glu Glu Pro Tyr Met Ser Cys Gly Tyr Gly Thr
     50                  55                  60 aaa gac gac gac tat ggc tgt gtg ccc tgc cct gca gag aag ttc tcc     240
Lys Asp Asp Asp Tyr Gly Cys Val Pro Cys Pro Ala Glu Lys Phe Ser
 65                  70                  75                  80 aaa gga ggt tat cag ata tgc agg cgc cac aaa gac tgt gag ggc ttc     288
Lys Gly Gly Tyr Gln Ile Cys Arg Arg His Lys Asp Cys Glu Gly Phe
                 85                  90                  95 ttc cgg gcc act gtg ctg aca cca gga gac atg gaa aac gac gct gag     336
Phe Arg Ala Thr Val Leu Thr Pro Gly Asp Met Glu Asn Asp Ala Glu
            100                 105                 110 tgt ggc cca tgt ctc cct ggc tac tac atg ctg gaa aac aga ccc agg     384
Cys Gly Pro Cys Leu Pro Gly Tyr Tyr Met Leu Glu Asn Arg Pro Arg
        115                 120                 125 aac atc tat ggc atg gtc tgc tac tcc tgt ctc ttg gca cct ccc aac     432
Asn Ile Tyr Gly Met Val Cys Tyr Ser Cys Leu Leu Ala Pro Pro Asn
    130                 135                 140
```

```
acc aag gaa tgt gtg gga gcc act tct ggg gtt tca gca cac tca tcc    480
Thr Lys Glu Cys Val Gly Ala Thr Ser Gly Val Ser Ala His Ser Ser
145                 150                 155                 160 agc act tcc ggt ggc agc acc ttg tct ccc ttc cag cat gct cac aaa    528
Ser Thr Ser Gly Gly Ser Thr Leu Ser Pro Phe Gln His Ala His Lys
                165                 170                 175 gag ctc tca ggc caa gga cac ctg gcc acc gcc ctg att att gcc atg    576
Glu Leu Ser Gly Gln Gly His Leu Ala Thr Ala Leu Ile Ile Ala Met
            180                 185                 190 tct acg atc ttc atc atg gcc att gcc atc gtc ctc atc atc atg ttc    624
Ser Thr Ile Phe Ile Met Ala Ile Ala Ile Val Leu Ile Ile Met Phe
        195                 200                 205 tac atc atg aag act aag ccg tca gct cca gcc tgc tgt agc agt ccc    672
Tyr Ile Met Lys Thr Lys Pro Ser Ala Pro Ala Cys Cys Ser Ser Pro
    210                 215                 220 cca gga aag agc gca gaa gcc cca gct aac aca cac gag gag aaa aaa    720
Pro Gly Lys Ser Ala Glu Ala Pro Ala Asn Thr His Glu Glu Lys Lys
225                 230                 235                 240 gag gcc cca gac agt gtg gtg acg ttc cct gag aat ggt gag ttc cag    768
Glu Ala Pro Asp Ser Val Val Thr Phe Pro Glu Asn Gly Glu Phe Gln
                245                 250                 255 aag ctg aca gca aca ccc aca aag acc ccc aaa agt gag aat gat gcc    816
Lys Leu Thr Ala Thr Pro Thr Lys Thr Pro Lys Ser Glu Asn Asp Ala
            260                 265                 270 tcc tct gag aac gag cag ttg cta agt cgc agt gtg gac agt gat gaa    864
Ser Ser Glu Asn Glu Gln Leu Leu Ser Arg Ser Val Asp Ser Asp Glu
        275                 280                 285 gag cca gcc ccg gac aag cag ggg tcc cca gag cta tgt ctg ctg tcg    912
Glu Pro Ala Pro Asp Lys Gln Gly Ser Pro Glu Leu Cys Leu Leu Ser
    290                 295                 300 cta gtt cac ctg gcc agg gag aag tct gtg acc agt aac aag tct gct    960
Leu Val His Leu Ala Arg Glu Lys Ser Val Thr Ser Asn Lys Ser Ala
305                 310                 315                 320 ggg atc cag agc cgg agg aaa aag ata ctg gat gtg tat gcc aac gtg   1008
Gly Ile Gln Ser Arg Arg Lys Lys Ile Leu Asp Val Tyr Ala Asn Val
                325                 330                 335 tgt ggt gtt gtt gaa ggt ctc agc ccc acc gag ttg ccg ttt gac tgc   1056
Cys Gly Val Val Glu Gly Leu Ser Pro Thr Glu Leu Pro Phe Asp Cys
            340                 345                 350 ctt gag aag aca agc cga atg ctc agc tct aca tac aac tct gag aag   1104
Leu Glu Lys Thr Ser Arg Met Leu Ser Ser Thr Tyr Asn Ser Glu Lys
        355                 360                 365 gcg gtc gtg aaa aca tgg cgc cac ctt gcc gag agc ttt gga ctg aag   1152
Ala Val Val Lys Thr Trp Arg His Leu Ala Glu Ser Phe Gly Leu Lys
    370                 375                 380 agg gat gag att ggg ggc atg act gat ggc atg cag ctc ttt gac cgc   1200
Arg Asp Glu Ile Gly Gly Met Thr Asp Gly Met Gln Leu Phe Asp Arg
385                 390                 395                 400 atc agc acc gcg ggc tac agc atc cca gag ctg ctc aca aag ttg gtg   1248
Ile Ser Thr Ala Gly Tyr Ser Ile Pro Glu Leu Leu Thr Lys Leu Val
                405                 410                 415 cag atc gag cgg ctg gat gct gtg gag tcc ttg tgt gca gac ata ttg   1296
Gln Ile Glu Arg Leu Asp Ala Val Glu Ser Leu Cys Ala Asp Ile Leu
            420                 425                 430 gag tgg gct ggg gtt gta cca cct gcc tcc cca ccc cca gct gcg tcc   1344
Glu Trp Ala Gly Val Val Pro Pro Ala Ser Pro Pro Pro Ala Ala Ser
        435                 440                 445 tga                                                                1347
```

```
<210> SEQ ID NO 14
<211> LENGTH: 1176
<212> TYPE: DNA
<213> ORGANISM: Homo sapiens
<220> FEATURE:
<221> NAME/KEY: CDS
<222> LOCATION: (1)..(1176)

<400> SEQUENCE: 14 atg ggc tac ccg gag gtg gag cgc agg gaa ctc ctg cct gca gca gcg       48
Met Gly Tyr Pro Glu Val Glu Arg Arg Glu Leu Leu Pro Ala Ala Ala
 1               5                  10                  15 ccg cgg gag cga ggg agc cag ggc tgc ggg tgt ggc ggg gcc cct gcc       96
Pro Arg Glu Arg Gly Ser Gln Gly Cys Gly Cys Gly Gly Ala Pro Ala
             20                  25                  30 cgg gcg ggc gaa ggg aac agc tgc ctg ctc ttc ctg ggt ttc ttt ggc      144
Arg Ala Gly Glu Gly Asn Ser Cys Leu Leu Phe Leu Gly Phe Phe Gly
         35                  40                  45 ctc tcg ctg gcc ctc cac ctg ctg acg ttg tgc tgc tac cta gag ttg      192
Leu Ser Leu Ala Leu His Leu Leu Thr Leu Cys Cys Tyr Leu Glu Leu
     50                  55                  60 cgc tcg gag ttg cgg cgg gaa cgt gga gcc gag tcc cgc ctt ggc ggc      240
Arg Ser Glu Leu Arg Arg Glu Arg Gly Ala Glu Ser Arg Leu Gly Gly
 65                  70                  75                  80 tcg ggc acc cct ggc acc tct ggc acc cta agc agc ctc ggt ggc ctc      288
Ser Gly Thr Pro Gly Thr Ser Gly Thr Leu Ser Ser Leu Gly Gly Leu
                 85                  90                  95 gac cct gac agc ccc atc acc agt cac ctt ggg cag ccg tca cct aag      336
Asp Pro Asp Ser Pro Ile Thr Ser His Leu Gly Gln Pro Ser Pro Lys
            100                 105                 110 cag cag cca ttg gaa ccg gga gaa gcc gca ctc cac tct gac tcc cag      384
Gln Gln Pro Leu Glu Pro Gly Glu Ala Ala Leu His Ser Asp Ser Gln
        115                 120                 125 gac ggg cac cag atg gcc cta ttg aat ttc ttc ttc cct gat gaa aag      432
Asp Gly His Gln Met Ala Leu Leu Asn Phe Phe Phe Pro Asp Glu Lys
    130                 135                 140 cca tac tct gaa gaa gaa agt agg cgt gtt cgc cgc aat aaa aga agc      480
Pro Tyr Ser Glu Glu Glu Ser Arg Arg Val Arg Arg Asn Lys Arg Ser
145                 150                 155                 160 aaa agc aat gaa gga gca gat ggc cca gtt aaa aac aag aaa aag gga      528
Lys Ser Asn Glu Gly Ala Asp Gly Pro Val Lys Asn Lys Lys Lys Gly
                165                 170                 175 aag aaa gca gga cct cct gga ccc aat ggc cct cca gga ccc cca gga      576
Lys Lys Ala Gly Pro Pro Gly Pro Asn Gly Pro Pro Gly Pro Pro Gly
            180                 185                 190 cct cca gga ccc cag gga ccc cca gga att cca ggg att cct gga att      624
Pro Pro Gly Pro Gln Gly Pro Pro Gly Ile Pro Gly Ile Pro Gly Ile
        195                 200                 205 cca gga aca act gtt atg gga cca cct ggt cct cca ggt cct cct ggt      672
Pro Gly Thr Thr Val Met Gly Pro Pro Gly Pro Pro Gly Pro Pro Gly
    210                 215                 220 cct caa gga ccc cct ggc ctc cag gga cct tct ggt gct gct gat aaa      720
Pro Gln Gly Pro Pro Gly Leu Gln Gly Pro Ser Gly Ala Ala Asp Lys
225                 230                 235                 240 gct gga act cga gaa aac cag cca gct gtg gtg cat cta cag ggc caa      768
Ala Gly Thr Arg Glu Asn Gln Pro Ala Val Val His Leu Gln Gly Gln
                245                 250                 255 ggg tca gca att caa gtc aag aat gat ctt tca ggt gga gtg ctc aat      816
Gly Ser Ala Ile Gln Val Lys Asn Asp Leu Ser Gly Gly Val Leu Asn
            260                 265                 270
```

```
gac tgg tct cgc atc act atg aac ccc aag gtg ttt aag cta cat ccc    864
Asp Trp Ser Arg Ile Thr Met Asn Pro Lys Val Phe Lys Leu His Pro
        275                 280                 285 cgc agc ggg gag ctg gag gta ctg gtg gac ggc acc tac ttc atc tat    912
Arg Ser Gly Glu Leu Glu Val Leu Val Asp Gly Thr Tyr Phe Ile Tyr
        290                 295                 300 agt cag gta gaa gta tac tac atc aac ttc act gac ttt gcc agc tat    960
Ser Gln Val Glu Val Tyr Tyr Ile Asn Phe Thr Asp Phe Ala Ser Tyr
305                 310                 315                 320 gag gtg gtg gtg gat gag aag ccc ttc ctg cag tgc aca cgc agc atc   1008
Glu Val Val Val Asp Glu Lys Pro Phe Leu Gln Cys Thr Arg Ser Ile
                325                 330                 335 gag acg ggc aag acc aac tac aac act tgc tat acc gca ggc gtc tgc   1056
Glu Thr Gly Lys Thr Asn Tyr Asn Thr Cys Tyr Thr Ala Gly Val Cys
            340                 345                 350 ctc ctc aag gcc cgg cag aag atc gcc gtc aag atg gtg cac gct gac   1104
Leu Leu Lys Ala Arg Gln Lys Ile Ala Val Lys Met Val His Ala Asp
        355                 360                 365 atc tcc atc aac atg agc aag cac acc acg ttc ttt ggg gcc atc agg   1152
Ile Ser Ile Asn Met Ser Lys His Thr Thr Phe Phe Gly Ala Ile Arg
370                 375                 380 ctg ggt gaa gcc cct gca tcc tag                                    1176
Leu Gly Glu Ala Pro Ala Ser
385                 390

<210> SEQ ID NO 15
<211> LENGTH: 1134
<212> TYPE: DNA
<213> ORGANISM: Mus musculus
<220> FEATURE:
<221> NAME/KEY: CDS
<222> LOCATION: (1)..(1134)

<400> SEQUENCE: 15 atg ggc tac cca gag gta gag cgc agg gaa ccc ctg cct gcg gca gcg     48
Met Gly Tyr Pro Glu Val Glu Arg Arg Glu Pro Leu Pro Ala Ala Ala
1               5                   10                  15 cca agg gag cgg ggc agc cag ggc tgc ggc tgt cgc ggg gcc cct gct     96
Pro Arg Glu Arg Gly Ser Gln Gly Cys Gly Cys Arg Gly Ala Pro Ala
                20                  25                  30 cgg gcg ggc gaa ggg aac agc tgc cgg ctc ttc ctg ggt ttc ttt ggc    144
Arg Ala Gly Glu Gly Asn Ser Cys Arg Leu Phe Leu Gly Phe Phe Gly
            35                  40                  45 ctc tcg ctg gcc ctc cac ctg ctg acg ctg tgc tac cta gag ttg        192
Leu Ser Leu Ala Leu His Leu Leu Thr Leu Cys Cys Tyr Leu Glu Leu
        50                  55                  60 cgg tcc gaa ttg cgg cgg gaa cgg gga acc gag tcc cgc ctc ggt ggc    240
Arg Ser Glu Leu Arg Arg Glu Arg Gly Thr Glu Ser Arg Leu Gly Gly
65                  70                  75                  80 ccg ggt gct cct ggc acc tct ggc acc cta agc agc cct ggg agc ctc    288
Pro Gly Ala Pro Gly Thr Ser Gly Thr Leu Ser Ser Pro Gly Ser Leu
                85                  90                  95 gac ccg gtg ggt ccc atc acc cgc cac ctg ggg cag ccg tcc ttt caa    336
Asp Pro Val Gly Pro Ile Thr Arg His Leu Gly Gln Pro Ser Phe Gln
            100                 105                 110 cag cag cct ttg gaa ccg gga gaa gat cca ctc ccc cct gag tcc cag    384
Gln Gln Pro Leu Glu Pro Gly Glu Asp Pro Leu Pro Pro Glu Ser Gln
        115                 120                 125 gac cgg cac cag atg gcc ctc ctg aat ttc ttc ttt cct gat gaa aag    432
Asp Arg His Gln Met Ala Leu Leu Asn Phe Phe Phe Pro Asp Glu Lys
130                 135                 140
```

```
gca tat tct gaa gag gaa agt agg cgt gtt cgc cgc aat aag aga agc      480
Ala Tyr Ser Glu Glu Glu Ser Arg Arg Val Arg Arg Asn Lys Arg Ser
145                 150                 155                 160 aaa agt ggt gaa gga gca gat ggt cct gtt aaa aac aag aaa aag gga      528
Lys Ser Gly Glu Gly Ala Asp Gly Pro Val Lys Asn Lys Lys Lys Gly
                165                 170                 175 aag aag gca ggg cca cct ggg ccc aac ggc ccc cca gga cct cca gga      576
Lys Lys Ala Gly Pro Pro Gly Pro Asn Gly Pro Pro Gly Pro Pro Gly
            180                 185                 190 cct ccg gga ccc cag gga cct cca ggg att cca gga att cct ggg att      624
Pro Pro Gly Pro Gln Gly Pro Pro Gly Ile Pro Gly Ile Pro Gly Ile
        195                 200                 205 cca gga aca act gtt atg gga cca cct ggc cca cct ggc cct cct ggt      672
Pro Gly Thr Thr Val Met Gly Pro Pro Gly Pro Pro Gly Pro Pro Gly
    210                 215                 220 cct caa gga ccc cct ggc ctc caa gga cct tct ggt gct gct gat aaa      720
Pro Gln Gly Pro Pro Gly Leu Gln Gly Pro Ser Gly Ala Ala Asp Lys
225                 230                 235                 240 act gga act cgg gaa aat cag cca gct gtg gtg cat ctg cag ggc caa      768
Thr Gly Thr Arg Glu Asn Gln Pro Ala Val Val His Leu Gln Gly Gln
                245                 250                 255 ggg tca gca att caa gtc aaa aat gat ctt tca ggt gga gtg ctc aat      816
Gly Ser Ala Ile Gln Val Lys Asn Asp Leu Ser Gly Gly Val Leu Asn
            260                 265                 270 gac tgg tct cgc atc act atg aac cct aag gtg ttt aaa cta cat ccc      864
Asp Trp Ser Arg Ile Thr Met Asn Pro Lys Val Phe Lys Leu His Pro
        275                 280                 285 cgc agc ggg gag ctg gag gtc tac tac atc aac ttc act gac ttt gcc      912
Arg Ser Gly Glu Leu Glu Val Tyr Tyr Ile Asn Phe Thr Asp Phe Ala
    290                 295                 300 agc tac gag gtg gtg gtg gat gag aag ccc ttc ctg cag tgc acc cgc      960
Ser Tyr Glu Val Val Val Asp Glu Lys Pro Phe Leu Gln Cys Thr Arg
305                 310                 315                 320 agc att gag aca ggg aag acc aac tac aac act tgc tat act gca ggc     1008
Ser Ile Glu Thr Gly Lys Thr Asn Tyr Asn Thr Cys Tyr Thr Ala Gly
                325                 330                 335 gtg tgc ctc ctc aag gcc agg cag aaa atc gcc gtg aag atg gtg cac     1056
Val Cys Leu Leu Lys Ala Arg Gln Lys Ile Ala Val Lys Met Val His
            340                 345                 350 gct gac atc tct atc aat atg agc aag cac acc acc ttc ttc ggg gcc     1104
Ala Asp Ile Ser Ile Asn Met Ser Lys His Thr Thr Phe Phe Gly Ala
        355                 360                 365 atc agg ctg ggc gaa gcc cct gca tcc tag                             1134
Ile Arg Leu Gly Glu Ala Pro Ala Ser
370                 375

<210> SEQ ID NO 16
<211> LENGTH: 1347
<212> TYPE: DNA
<213> ORGANISM: Homo sapiens
<220> FEATURE:
<221> NAME/KEY: CDS
<222> LOCATION: (1)..(1347)

<400> SEQUENCE: 16 atg gcc cat gtg ggg gac tgc acg cag acg ccc tgg ctc ccc gtc ctg      48
Met Ala His Val Gly Asp Cys Thr Gln Thr Pro Trp Leu Pro Val Leu
1               5                   10                  15 gtg gtg tct ctg atg tgc tca gcc cga gcg gaa tac tca aac tgc ggt      96
Val Val Ser Leu Met Cys Ser Ala Arg Ala Glu Tyr Ser Asn Cys Gly
            20                  25                  30
```

```
gag aac gag tac tac aac cag act acg ggg ctg tgc cag gag tgc ccc        144
Glu Asn Glu Tyr Tyr Asn Gln Thr Thr Gly Leu Cys Gln Glu Cys Pro
        35                  40                  45 ccg tgt ggg ccg gga gag gag ccc tac ctg tcc tgt ggc tac ggc acc        192
Pro Cys Gly Pro Gly Glu Glu Pro Tyr Leu Ser Cys Gly Tyr Gly Thr
 50                  55                  60 aaa gac gag gac tac ggc tgc gtc ccc tgc ccg gcg gag aag ttt tcc        240
Lys Asp Glu Asp Tyr Gly Cys Val Pro Cys Pro Ala Glu Lys Phe Ser
 65                  70                  75                  80 aaa gga ggc tac cag ata tgc agg cgt cac aaa gac tgt gag ggc ttc        288
Lys Gly Gly Tyr Gln Ile Cys Arg Arg His Lys Asp Cys Glu Gly Phe
            85                  90                  95 ttc cgg gcc acc gtg ctg aca cca ggg gac atg gag aat gac gct gag        336
Phe Arg Ala Thr Val Leu Thr Pro Gly Asp Met Glu Asn Asp Ala Glu
                100                 105                 110 tgt ggc cct tgc ctc cct ggc tac tac atg ctg gag aac aga ccg agg        384
Cys Gly Pro Cys Leu Pro Gly Tyr Tyr Met Leu Glu Asn Arg Pro Arg
            115                 120                 125 aac atc tat ggc atg gtc tgc tac tcc tgc ctc ctg gca ccc ccc aac        432
Asn Ile Tyr Gly Met Val Cys Tyr Ser Cys Leu Leu Ala Pro Pro Asn
130                 135                 140 acc aag gaa tgt gtg gga gcc act tca gga gct tct gcc aac ttc cct        480
Thr Lys Glu Cys Val Gly Ala Thr Ser Gly Ala Ser Ala Asn Phe Pro
145                 150                 155                 160 ggc acc tcg ggc agc agc acc ctg tct ccc ttc cag cac gcc cac aaa        528
Gly Thr Ser Gly Ser Ser Thr Leu Ser Pro Phe Gln His Ala His Lys
                165                 170                 175 gaa ctc tca ggc caa gga cac ctg gcc act gcc ctg atc att gca atg        576
Glu Leu Ser Gly Gln Gly His Leu Ala Thr Ala Leu Ile Ile Ala Met
            180                 185                 190 tcc acc atc ttc atc atg gcc atc gcc atc gtc ctc atc atc atg ttc        624
Ser Thr Ile Phe Ile Met Ala Ile Ala Ile Val Leu Ile Ile Met Phe
        195                 200                 205 tac atc ctg aag aca aag ccc tct gcc cca gcc tgt tgc acc agc cac        672
Tyr Ile Leu Lys Thr Lys Pro Ser Ala Pro Ala Cys Cys Thr Ser His
    210                 215                 220 ccg ggg aag agc gtg gag gcc caa gtg agc aag gac gag gag aag aaa        720
Pro Gly Lys Ser Val Glu Ala Gln Val Ser Lys Asp Glu Glu Lys Lys
225                 230                 235                 240 gag gcc cca gac aac gtg gtg atg ttc tcc gag aag gat gaa ttt gag        768
Glu Ala Pro Asp Asn Val Val Met Phe Ser Glu Lys Asp Glu Phe Glu
                245                 250                 255 aag ctg aca gca act cca gca aag ccc acc aag agc gag aac gat gcc        816
Lys Leu Thr Ala Thr Pro Ala Lys Pro Thr Lys Ser Glu Asn Asp Ala
            260                 265                 270 tca tcc gag aat gag cag ctg ctg agc cgg agc gtc gac agt gat gag        864
Ser Ser Glu Asn Glu Gln Leu Leu Ser Arg Ser Val Asp Ser Asp Glu
        275                 280                 285 gag ccc gcc cct gac aag cag ggc tcc ccg gag ctg tgc ctg ctg tcg        912
Glu Pro Ala Pro Asp Lys Gln Gly Ser Pro Glu Leu Cys Leu Leu Ser
    290                 295                 300 ctg gtt cac ctg gcc agg gag aag tct gcc acc agc aac aag tca gcc        960
Leu Val His Leu Ala Arg Glu Lys Ser Ala Thr Ser Asn Lys Ser Ala
305                 310                 315                 320 ggg att caa agc cgg agg aaa aag atc ctc gat gtg tat gcc aac gtg       1008
Gly Ile Gln Ser Arg Arg Lys Lys Ile Leu Asp Val Tyr Ala Asn Val
                325                 330                 335 tgt gga gtc gtg gaa ggt ctt agc ccc acg gag ctg cca ttt gat tgc       1056
Cys Gly Val Val Glu Gly Leu Ser Pro Thr Glu Leu Pro Phe Asp Cys
            340                 345                 350
```

-continued

```
ctc gag aag act agc cga atg ctc agc tcc acg tac aac tct gag aag    1104
Leu Glu Lys Thr Ser Arg Met Leu Ser Ser Thr Tyr Asn Ser Glu Lys
        355                 360                 365 gct gtt gtg aaa acg tgg cgc cac ctc gcc gag agc ttc ggc ctg aag    1152
Ala Val Val Lys Thr Trp Arg His Leu Ala Glu Ser Phe Gly Leu Lys
370                 375                 380 agg gat gag att ggg ggc atg aca gac ggc atg caa ctc ttt gac cgc    1200
Arg Asp Glu Ile Gly Gly Met Thr Asp Gly Met Gln Leu Phe Asp Arg
385                 390                 395                 400 atc agc acg gca ggc tac agc atc cct gag cta ctc aca aaa ctg gtg    1248
Ile Ser Thr Ala Gly Tyr Ser Ile Pro Glu Leu Leu Thr Lys Leu Val
                405                 410                 415 cag att gag cgg ctg gat gct gtg gag tcc ttg tgt gca gac ata ctg    1296
Gln Ile Glu Arg Leu Asp Ala Val Glu Ser Leu Cys Ala Asp Ile Leu
            420                 425                 430 gag tgg gcg ggg gtt gtg cca cct gcc tcc cag cca cat gct gca tcc    1344
Glu Trp Ala Gly Val Val Pro Pro Ala Ser Gln Pro His Ala Ala Ser
        435                 440                 445 tga                                                                 1347
```

<210> SEQ ID NO 17
<211> LENGTH: 448
<212> TYPE: PRT
<213> ORGANISM: Homo sapiens

<400> SEQUENCE: 17

```
Met Ala His Val Gly Asp Cys Thr Gln Thr Pro Trp Leu Pro Val Leu
  1               5                  10                  15

Val Val Ser Leu Met Cys Ser Ala Arg Ala Glu Tyr Ser Asn Cys Gly
                 20                  25                  30

Glu Asn Glu Tyr Tyr Asn Gln Thr Thr Gly Leu Cys Gln Glu Cys Pro
             35                  40                  45

Pro Cys Gly Pro Gly Glu Glu Pro Tyr Leu Ser Cys Gly Tyr Gly Thr
         50                  55                  60

Lys Asp Glu Asp Tyr Gly Cys Val Pro Cys Pro Ala Glu Lys Phe Ser
 65                  70                  75                  80

Lys Gly Gly Tyr Gln Ile Cys Arg Arg His Lys Asp Cys Glu Gly Phe
                 85                  90                  95

Phe Arg Ala Thr Val Leu Thr Pro Gly Asp Met Glu Asn Asp Ala Glu
                100                 105                 110

Cys Gly Pro Cys Leu Pro Gly Tyr Tyr Met Leu Glu Asn Arg Pro Arg
            115                 120                 125

Asn Ile Tyr Gly Met Val Cys Tyr Ser Cys Leu Leu Ala Pro Pro Asn
        130                 135                 140

Thr Lys Glu Cys Val Gly Ala Thr Ser Gly Ala Ser Ala Asn Phe Pro
145                 150                 155                 160

Gly Thr Ser Gly Ser Ser Thr Leu Ser Pro Phe Gln His Ala His Lys
                165                 170                 175

Glu Leu Ser Gly Gln Gly His Leu Ala Thr Ala Leu Ile Ile Ala Met
            180                 185                 190

Ser Thr Ile Phe Ile Met Ala Ile Ala Ile Val Leu Ile Ile Met Phe
        195                 200                 205

Tyr Ile Leu Lys Thr Lys Pro Ser Ala Pro Ala Cys Cys Thr Ser His
    210                 215                 220

Pro Gly Lys Ser Val Glu Ala Gln Val Ser Lys Asp Glu Glu Lys Lys
225                 230                 235                 240
```

```
Glu Ala Pro Asp Asn Val Val Met Phe Ser Lys Asp Glu Phe Glu
            245                 250                 255

Lys Leu Thr Ala Thr Pro Ala Lys Pro Thr Lys Ser Glu Asn Asp Ala
            260                 265                 270

Ser Ser Glu Asn Glu Gln Leu Leu Ser Arg Ser Val Asp Ser Asp Glu
            275                 280                 285

Glu Pro Ala Pro Asp Lys Gln Gly Ser Pro Glu Leu Cys Leu Leu Ser
        290                 295                 300

Leu Val His Leu Ala Arg Glu Lys Ser Ala Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
            340                 345                 350

Leu Glu Lys Thr Ser Arg Met Leu Ser Ser Thr Tyr Asn Ser Glu Lys
            355                 360                 365

Ala Val Val Lys Thr Trp Arg His Leu Ala Glu Ser Phe Gly Leu Lys
        370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415

Gln Ile Glu Arg Leu Asp Ala Val Glu Ser Leu Cys Ala Asp Ile Leu
            420                 425                 430

Glu Trp Ala Gly Val Val Pro Pro Ala Ser Gln Pro His Ala Ala Ser
        435                 440                 445

<210> SEQ ID NO 18
<211> LENGTH: 4235
<212> TYPE: DNA
<213> ORGANISM: Homo sapiens
<220> FEATURE:
<221> NAME/KEY: CDS
<222> LOCATION: (433)..(1779)

<400> SEQUENCE: 18
gggggcagac ggccgaagag ccaggtgtgc cagggaccta tggcagcagg gctgaacgtg     60
cccgctccag cctctccagt gctgggagag acctctagat ggtgcaggtg agtttgcaat    120
gagggaaagc ccctcggcaa ggactgagtt tccaaacttg cagacagggc agggagcggt    180
caaggaagag ttcccgggaa gccctttaaa cggaaaggaa gcggggctag tgtcagagag    240
gtgtgccagg tccaggcag ccctgctgac ccctaaggac atagagtacc tgcttctgag    300
agggctgcca cggtggccac ctgtgaagcc tgtcacccag aactggatgg tacctgactt    360
tcttcataga cccatcttct gctgggactg aagctgacct ccaacagaag ccaggtgagc    420
ccttgggaga gg atg gcc cat gtg ggg gac tgc acg cag acg ccc tgg ctc    471
              Met Ala His Val Gly Asp Cys Thr Gln Thr Pro Trp Leu
                1               5                   10 ccc gtc ctg gtg gtg tct ctg atg tgc tca gcc cga gcg gaa tac tca    519
Pro Val Leu Val Val Ser Leu Met Cys Ser Ala Arg Ala Glu Tyr Ser
        15                  20                  25 aac tgc ggt gag aac gag tac tac aac cag act acg ggg ctg tgc cag    567
Asn Cys Gly Glu Asn Glu Tyr Tyr Asn Gln Thr Thr Gly Leu Cys Gln
 30                  35                  40                  45 gag tgc ccc ccg tgt ggg ccg gga gag gag ccc tac ctg tcc tgt ggc    615
Glu Cys Pro Pro Cys Gly Pro Gly Glu Glu Pro Tyr Leu Ser Cys Gly
```

-continued

```
                      50                          55                          60
tac ggc acc aaa gac gag gac tac ggc tgc gtc ccc tgc ccg gcg gag      663
Tyr Gly Thr Lys Asp Glu Asp Tyr Gly Cys Val Pro Cys Pro Ala Glu
                  65                          70                          75 aag ttt tcc aaa gga ggc tac cag ata tgc agg cgt cac aaa gac tgt      711
Lys Phe Ser Lys Gly Gly Tyr Gln Ile Cys Arg Arg His Lys Asp Cys
             80                          85                          90 gag ggc ttc ttc cgg gcc acc gtg ctg aca cca ggg gac atg gag aat      759
Glu Gly Phe Phe Arg Ala Thr Val Leu Thr Pro Gly Asp Met Glu Asn
         95                         100                         105 gac gct gag tgt ggc cct tgc ctc cct ggc tac tac atg ctg gag aac      807
Asp Ala Glu Cys Gly Pro Cys Leu Pro Gly Tyr Tyr Met Leu Glu Asn
110                         115                         120                     125 aga ccg agg aac atc tat ggc atg gtc tgc tac tcc tgc ctc ctg gca      855
Arg Pro Arg Asn Ile Tyr Gly Met Val Cys Tyr Ser Cys Leu Leu Ala
                    130                         135                         140 ccc ccc aac acc aag gaa tgt gtg gga gcc act tca gga gct tct gcc      903
Pro Pro Asn Thr Lys Glu Cys Val Gly Ala Thr Ser Gly Ala Ser Ala
                145                         150                         155 aac ttc cct ggc acc tcg ggc agc agc acc ctg tct ccc ttc cag cac      951
Asn Phe Pro Gly Thr Ser Gly Ser Ser Thr Leu Ser Pro Phe Gln His
            160                         165                         170 gcc cac aaa gaa ctc tca ggc caa gga cac ctg gcc act gcc ctg atc      999
Ala His Lys Glu Leu Ser Gly Gln Gly His Leu Ala Thr Ala Leu Ile
175                         180                         185 att gca atg tcc acc atc ttc atc atg gcc atc gcc atc gtc ctc atc     1047
Ile Ala Met Ser Thr Ile Phe Ile Met Ala Ile Ala Ile Val Leu Ile
190                         195                         200                     205 atc atg ttc tac atc ctg aag aca aag ccc tct gcc cca gcc tgt tgc     1095
Ile Met Phe Tyr Ile Leu Lys Thr Lys Pro Ser Ala Pro Ala Cys Cys
                    210                         215                         220 acc agc cac ccg ggg aag agc gtg gag gcc caa gtg agc aag gac gag     1143
Thr Ser His Pro Gly Lys Ser Val Glu Ala Gln Val Ser Lys Asp Glu
                225                         230                         235 gag aag aaa gag gcc cca gac aac gtg gtg atg ttc tcc gag aag gat     1191
Glu Lys Lys Glu Ala Pro Asp Asn Val Val Met Phe Ser Glu Lys Asp
            240                         245                         250 gaa ttt gag aag ctg aca gca act cca gca aag ccc acc aag agc gag     1239
Glu Phe Glu Lys Leu Thr Ala Thr Pro Ala Lys Pro Thr Lys Ser Glu
        255                         260                         265 aac gat gcc tca tcc gag aat gag cag ctg ctg agc cgg agc gtc gac     1287
Asn Asp Ala Ser Ser Glu Asn Glu Gln Leu Leu Ser Arg Ser Val Asp
270                         275                         280                     285 agt gat gag gag ccc gcc cct gac aag cag ggc tcc ccg gag ctg tgc     1335
Ser Asp Glu Glu Pro Ala Pro Asp Lys Gln Gly Ser Pro Glu Leu Cys
                    290                         295                         300 ctg ctg tcg ctg gtt cac ctg gcc agg gag aag tct gcc acc agc aac     1383
Leu Leu Ser Leu Val His Leu Ala Arg Glu Lys Ser Ala Thr Ser Asn
                305                         310                         315 aag tca gcc ggg att caa agc cgg agg aaa aag atc ctc gat gtg tat     1431
Lys Ser Ala Gly Ile Gln Ser Arg Arg Lys Lys Ile Leu Asp Val Tyr
            320                         325                         330 gcc aac gtg tgt gga gtc gtg gaa ggt ctt agc ccc acg gag ctg cca     1479
Ala Asn Val Cys Gly Val Val Glu Gly Leu Ser Pro Thr Glu Leu Pro
        335                         340                         345 ttt gat tgc ctc gag aag act agc cga atg ctc agc tcc acg tac aac     1527
Phe Asp Cys Leu Glu Lys Thr Ser Arg Met Leu Ser Ser Thr Tyr Asn
350                         355                         360                     365 tct gag aag gct gtt gtg aaa acg tgg cgc cac ctc gcc gag agc ttc     1575
```

-continued

```
Ser Glu Lys Ala Val Val Lys Thr Trp Arg His Leu Ala Glu Ser Phe
            370                 375                 380 ggc ctg aag agg gat gag att ggg ggc atg aca gac ggc atg caa ctc      1623
Gly Leu Lys Arg Asp Glu Ile Gly Gly Met Thr Asp Gly Met Gln Leu
            385                 390                 395 ttt gac cgc atc agc acg gca ggc tac agc atc cct gag cta ctc aca      1671
Phe Asp Arg Ile Ser Thr Ala Gly Tyr Ser Ile Pro Glu Leu Leu Thr
            400                 405                 410 aaa ctg gtg cag att gag cgg ctg gat gct gtg gag tcc ttg tgt gca      1719
Lys Leu Val Gln Ile Glu Arg Leu Asp Ala Val Glu Ser Leu Cys Ala
        415                 420                 425 gac ata ctg gag tgg gcg ggg gtt gtg cca cct gcc tcc cag cca cat      1767
Asp Ile Leu Glu Trp Ala Gly Val Val Pro Pro Ala Ser Gln Pro His
430                 435                 440                 445 gct gca tcc tga aaagcatgcc tgtgggctgt cctcccagga caagccaagg          1819
Ala Ala Ser atccaacgag ggctctggag ctgtgagtgg tgccaaaaga ctgccaagaa tcaaggcttt    1879
tgtgatatgt caccgtatgc cttaggatgt tcaaggagcc agacgaaata aggcctgtct    1939
tccaatttaa ccaaagataa aggactagag ccgggatact ttcagatgct cgcctgtacc    1999
tcaccaggca gagtaaatat ctactcactc atacagccag cccaccagcc caccattaac    2059
tcactgaaca atgagacaat gttgaggact caaatgaatc aaacccgtg ggaatgacag     2119 aagtgaagaa tctggtccct gtctttaagg agtttgcact ccagtagaag acagaaggaa    2179
cgtatgttta caaccactt cactggaaga cgtcaaacaa gctgaatgaa ggggcgctta     2239
gaaaacgtta atagaagttc taagcgggag atgactccct actgggatga tgaaggatgg    2299
catcctagtg aagaagcagc tcaaacattt tgataaaatg caacaaaat gcagacaccc     2359 tgctccaggt attatttcag gtttagtaca agtctgttaa taccctatgt ggtttcatta    2419
ggataacttt ttacctatcc ttgaggtcat ccatattctt acaggccttc cagtcaataa    2479
tggaagagct cactctatac aaaaccaata tgcaaggcat gtgtttgtcc aagcaattgg    2539
atgtgtgcag tagccaattt catttactgc attactcttt ggcctgggaa ccctgtggtc    2599
tgcactacat gtgaatggcc ttccacttca gtcttaggca gatttgacct tttaggggca    2659
gcaatgctga aggacacagc aatttaaatt ataatgtgtc aggctgtgtt ttcacttcaa    2719
acatgtatga gtagtcagct gtaattagag aaatgatgac ttcctaagag ttcagccacg    2779
cataattcta gatttcaaga gcatctaaga cttgtggatt agcctcatgg catgagagtt    2839
tcagactcag ccttctgagc cagtcaggga aagtggagtt ctgcagcgca aatgagagcc    2899
tgggcttggt gtcgagggag ctggcttcta gttgtgccac cttgggcctt gtcttttcct    2959
ctctctgcct cagtttctcg tctgccaatg agatgttagt tagtgattct ataattgggg    3019
caggtagggt tcaggtgagc aaaaagaaag tggagctata ggaaatgcca ggcctttgag    3079
gtgctctatg gaagtcaaca cagtgtggtt tgtccattta aatgggaata aaaacagaaa    3139
aactcagact tggcattttc acaataactg caatggtttg acataacatt tataggcaga    3199
aagttaataa actggcattg ttcttggcat attattgtac tatccctgta actgccaaga    3259
gctcaggagc caggctagtg atcacaccag gggttagagt tcactgctga actccctgat    3319
ggcaggtctg tgtttattac tacattaaaa caaagtctct gacttataaa gcgaggtcgt    3379
aaaaattaca agttgcatga ctgaaaaaat gctttagggg gaaaatcagt catatcttta    3439
acaccaacaa gcaatttccc accaacgaat gtagtacata ctgtgagagg atcataatga    3499
ggtcctgaat atttaatatc atcatttact gtgtctgttt gctgctgttt ttcgaaccta    3559
```

-continued

```
tttggtttac cctgcaagct aaatactcca cggcagagct taattatcct tttaattcct      3619
ctttgaaatc ctgtggtgcc cccttccccc tgccttgtga tgatgatgag tgagtctccc      3679
cttaattaga ctgcaaatgt cacttgtgat gagtgtgcca ttccaggata acagcttgca      3739
ccctcctcag aatgttttca gcgaaagagt ggggtggctg ttctctgctc ctggtgcttt      3799
ggcctcattt cacactatta gaattctggg gctgtaaggc cagccagtgt cagctcatgt      3859
tccattggct ctccacctgc cattttagg gagctattcc ttatatagtt acaaattccc       3919
ttgtcattta cttatttgga aacatgggat ttactctgac aagctttagc ctatgttatg      3979
ggattcagaa caatgagatc ataataattc tcactgacca agctgggac tccatcctgc       4039 cattttttgtg tggagatatt cataattctg caatacttta aaacatttag aaaacacccc     4099
agggtaggtc tgtggcccct agacagtgaa gtcttaattg tcaatattat ttttgtctaa      4159
ttctgtatat ataaactta ttatattta taatctcaat aaacacatta ataaaaaaaa        4219
aaaaaaaaaa aaaaaa                                                     4235
```

<210> SEQ ID NO 19
<211> LENGTH: 448
<212> TYPE: PRT
<213> ORGANISM: Homo sapiens

<400> SEQUENCE: 19

```
Met Ala His Val Gly Asp Cys Thr Gln Thr Pro Trp Leu Pro Val Leu
  1               5                  10                  15

Val Val Ser Leu Met Cys Ser Ala Arg Ala Glu Tyr Ser Asn Cys Gly
             20                  25                  30

Glu Asn Glu Tyr Tyr Asn Gln Thr Thr Gly Leu Cys Gln Glu Cys Pro
         35                  40                  45

Pro Cys Gly Pro Gly Glu Glu Pro Tyr Leu Ser Cys Gly Tyr Gly Thr
     50                  55                  60

Lys Asp Glu Asp Tyr Gly Cys Val Pro Cys Pro Ala Glu Lys Phe Ser
 65                  70                  75                  80

Lys Gly Gly Tyr Gln Ile Cys Arg Arg His Lys Asp Cys Glu Gly Phe
                 85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125

Asn Ile Tyr Gly Met Val Cys Tyr Ser Cys Leu Leu Ala Pro Pro Asn
    130                 135                 140

Thr Lys Glu Cys Val Gly Ala Thr Ser Gly Ala Ser Ala Asn Phe Pro
145                 150                 155                 160

Gly Thr Ser Gly Ser Ser Thr Leu Ser Pro Phe Gln His Ala His Lys
                165                 170                 175

Glu Leu Ser Gly Gln Gly His Leu Ala Thr Ala Leu Ile Ile Ala Met
            180                 185                 190

Ser Thr Ile Phe Ile Met Ala Ile Ala Ile Val Leu Ile Ile Met Phe
        195                 200                 205

Tyr Ile Leu Lys Thr Lys Pro Ser Ala Pro Ala Cys Cys Thr Ser His
    210                 215                 220

Pro Gly Lys Ser Val Glu Ala Gln Val Ser Lys Asp Glu Glu Lys Lys
225                 230                 235                 240

Glu Ala Pro Asp Asn Val Val Met Phe Ser Glu Lys Asp Glu Phe Glu
```

```
                    245                 250                  255
Lys Leu Thr Ala Thr Pro Ala Lys Pro Thr Lys Ser Glu Asn Asp Ala
                260                 265                 270

Ser Ser Glu Asn Glu Gln Leu Leu Ser Arg Ser Val Asp Ser Asp Glu
            275                 280                 285

Glu Pro Ala Pro Asp Lys Gln Gly Ser Pro Glu Leu Cys Leu Leu Ser
        290                 295                 300

Leu Val His Leu Ala Arg Glu Lys Ser Ala Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
                340                 345                 350

Leu Glu Lys Thr Ser Arg Met Leu Ser Ser Thr Tyr Asn Ser Glu Lys
                355                 360                 365

Ala Val Val Lys Thr Trp Arg His Leu Ala Glu Ser Phe Gly Leu Lys
            370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415

Gln Ile Glu Arg Leu Asp Ala Val Glu Ser Leu Cys Ala Asp Ile Leu
            420                 425                 430

Glu Trp Ala Gly Val Val Pro Pro Ala Ser Gln Pro His Ala Ala Ser
            435                 440                 445
```

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:
     Oligonucleotide primer used to amplify exon 5 of
     EDA1-II.

<400> SEQUENCE: 20
agaaagcagg acctcctgg                                              19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:
     Oligonucleotide primer used to amplify exon 5 of
     EDA1-II.

<400> SEQUENCE: 21
ctctcaggat cacccactc                                              19

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:
     Oligonucleotide primer that can be used to
     diagnose ED.

<400> SEQUENCE: 22
tatgttggct atgactgact gagtgg                                      26

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide primer that can be used to
    diagnose ED.

<400> SEQUENCE: 23
ccctaccaag aaggtagttc                                              20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:
    Oligonucleotide primer that can be used to
    diagnose ED.

<400> SEQUENCE: 24
ctctcaggat cacccactcc tg                                           22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide primer that can be used to
    diagnose ED.

<400> SEQUENCE: 25
tgtcaattca ccacagggag                                              20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence:
    Oligonucleotide primer that can be used to
    diagnose ED.

<400> SEQUENCE: 26
gaatctagga tgcaggggc                                               19

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence:
    Oligonucleotide primer that can be used to
    diagnose ED.

<400> SEQUENCE: 27
tattgcggcg aacacg                                                  16

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence:
    Oligonucleotide primer that can be used to

```
            diagnose ED.

<400> SEQUENCE: 28
tattgcagcg aacacg                                                      16

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primer that can be used to
      diagnose ED.

<400> SEQUENCE: 29
tattgcggca aaacacg                                                     17

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer used to screen a BAC
      library.

<400> SEQUENCE: 30
atcatggctg tgcactctag                                                  20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer used to screen a BAC
      library.

<400> SEQUENCE: 31
acctactgca tgtctgtgga                                                  20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer used to screen a BAC
      library.

<400> SEQUENCE: 32
cacatgctca gtgttgtcca                                                  20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer used to screen a BAC
      library.

<400> SEQUENCE: 33
acacaggctc agtcatgcgg                                                  20

<210> SEQ ID NO 34
<211> LENGTH: 25
```

```
<212> TYPE: DNA
<213> ORGANISM: Artificial Sequence
<220> FEATURE:
<223> OTHER INFORMATION: Description of Artificial Sequence:
      Oligonucleotide primer used to clone a murine dl
      gene.

<400> SEQUENCE: 34
gcggtgaccc gggagatctg aattc                                            25

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence:
      Oligonucleotide primer used to clone a murine dl
      gene.

<400> SEQUENCE: 35
gaattcagat c                                                           11

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer used to clone a murine dl
      gene.

<400> SEQUENCE: 36
ctgagcggaa ttcgtgagac c                                                21

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer used to clone a murine dl
      gene.

<400> SEQUENCE: 37
ggtctcacga attccgctca gtt                                              23

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer used to clone a murine dl
      gene.

<400> SEQUENCE: 38
agtgagaatg atgcctcc                                                    18

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer used to clone a murine dl
      gene.

<400> SEQUENCE: 39
```

-continued gcctttgttc agtcatagg　　　　　　　　　　　　　　　　　　　　　　　　　　19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:
　　　Oligonucleotide primer used to clone a murine dl
　　　gene.

<400> SEQUENCE: 40
cctgagagct ctttgtgag　　　　　　　　　　　　　　　　　　　　　　　　　　19

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence:
　　　Oligonucleotide primer used to clone a murine dl
　　　gene.
<221> NAME/KEY: misc_feature
<222> LOCATION: (29)
<223> OTHER INFORMATION: h represents a or c or t/u

<400> SEQUENCE: 41
cgggatcctc gagggggggg ggggggggh　　　　　　　　　　　　　　　　　　　　29

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:
　　　Oligonucleotide primer used to clone a murine dl
　　　gene.

<400> SEQUENCE: 42
aagcagagct ccacaatc　　　　　　　　　　　　　　　　　　　　　　　　　　18

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence:
　　　Oligonucleotide primer used to clone a murine dl
　　　gene.
<221> NAME/KEY: misc_feature
<222> LOCATION: (38)..(39)
<223> OTHER INFORMATION: n represents a, c, t, or g; v represents a, g,
　　　or c

<400> SEQUENCE: 43
ggccgctctg gacaggatat gttttttttt ttttttvn　　　　　　　　　　　　　　　39

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:
　　　Oligonucleotide primer used to clone a murine dl
　　　gene.

<400> SEQUENCE: 44
ggaacagtca agagcgagtt　　　　　　　　　　　　　　　　　　　　　　　　　20

```
<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer used to clone a murine dl
      gene.

<400> SEQUENCE: 45
gcggatccag gccgctctgg acaggatatg                                     30

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 46
tggtgtctct gatgtgc                                                   17

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 47
acagtggccc ggaagaag                                                  18

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 48
ctgcggtgag aacgagtac                                                 19

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 49
ggcaaggtgg cgccatgt                                                  18

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.
```

```
<400> SEQUENCE: 50
ggcaccaaag acgaggacta                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 51
tcagcgtcat tctccatgtc                                              20

<210> SEQ ID NO 52
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 52
ctagactcga gaattcgcgg ccgcactagt tttttttttt tttttt                 46

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 53
tctggtagcc tcctttggaa                                              20

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 54
ctagactcga gaattcg                                                 17

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 55
tagtcctcgt ctttggtgcc                                              20

<210> SEQ ID NO 56
<211> LENGTH: 18
<212> TYPE: DNA
```

```
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 56
gagaattcgc ggccgcac                                                      18

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 57
agccccgtag tctggttgta                                                    20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 58
gcgtcgacag tgatgagga                                                     19

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 59
cagtcttttg gcaccactca                                                    20

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 60
acgtgtgtgg agtcgtgga                                                     19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 61
ctcgttggat ccttggctt                                                     19
```

```
<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 62
tacatgctgg agaacagacc                                               20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 63
ttccaaagga ggctaccaga                                               20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 64
ttggcagaag ctcctgaagt                                               20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 65
tgctcgagat gtgatgaagg                                               20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 66
aagcagatgg ccacagaact                                               20

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that were used to clone
``` human DL.

<400> SEQUENCE: 67
ggagaggatg gcccatgtg                                                19

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 68
cagaccatgc catagatgtt c                                             21

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 69
acttcaggag cttctgccaa                                               20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 70
tcgtccttgc tcacttggg                                                19

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 71
ggatgaattt gagaagctga c                                             21

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 72
ctgacttgtt cgtggtggc                                                19

<210> SEQ ID NO 73
<211> LENGTH: 19

```
<212> TYPE: DNA
<213> ORGANISM: Artificial Sequence
<220> FEATURE:
<223> OTHER INFORMATION: Description of Artificial Sequence:
      Oligonucleotide primer that were used to clone
      human DL.

<400> SEQUENCE: 73
tccacgactc cacacacgt                                               19

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 74
aaataaaggt agccagaccc                                              20

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 75
gtaaggggct cagaccact                                               19

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 76
catgtgtttc taaggaggta c                                            21

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 77
caacaatgcc acaagcagga                                              20

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 78
```

```
gtccgtatgg tttggctgc                                              19
```

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 79

```
gccagggttt gccaggag                                               18
```

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 80

```
gtccagctca cctgtctct                                              19
```

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 81

```
accggctctt tcctacacc                                              19
```

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 82

```
tggagcttct ctggatcatt t                                           21
```

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 83

```
aactccaggt gatcgatacc                                             20
```

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence:

```
          Oligonucleotide primer that can be used for
          mutation screening of human DL.

<400> SEQUENCE: 84
ctgggtcatt catgccttct                                              20

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 85
atggtgtgtg gaagccctg                                               19

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 86
catgagccaa ttctaactcc t                                            21

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 87
caggacccca gttcagctt                                               19

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 88
cccaggcact gctaatgac                                               19

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 89
ccacatctca cagctcatca                                              20

<210> SEQ ID NO 90
```

```
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 90
tttctactgt tgcccctttc t                                              21

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 91 cccagcccctt catgtcagt                                                19

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 92
tctattgact gtgacttgca                                                20

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used for
      mutation screening of human DL.

<400> SEQUENCE: 93
ctcgttggat ccttggctt                                                 19

<210> SEQ ID NO 94
<211> LENGTH: 425
<212> TYPE: DNA
<213> ORGANISM: Homo sapiens

<400> SEQUENCE: 94
tttttttttt tgggggcaga cggccgaaga gccaggtgtg ccaaggtcat atggcagcag      60
ggctgaacgt gcccgctcca gcctctccag tgctggaaga gacctctaga tggagcaggt     120
gagtttgcaa ttagggaaag cccctcggca aggactgagt ttccaaactt gcagacaggg     180
cagggagcgg tcaaggaaga gttcccggga agcccttttaa acggaaagga agcggggcta    240
gtgtcagaga ggtgtgacag gtcccagtca gccctgctgg cccctaagga catagagtac     300
ctgcttctga gagggctgcc acggtggcca cctgtgaagc ctgtcaccca gaactggatg     360
gtacctgact tcttcatag acccatcttc tgctgggact gaagctgacc tccaacagaa      420
gccag                                                                425
```

<210> SEQ ID NO 95
<211> LENGTH: 434
<212> TYPE: DNA
<213> ORGANISM: Homo sapiens
<220> FEATURE:
<221> NAME/KEY: misc_feature
<222> LOCATION: (1)..(434)
<223> OTHER INFORMATION: n represents a, c, t, or g

<400> SEQUENCE: 95

| | | | | | |
|---|---|---|---|---|---|
| gtaagccctg | gtcctttcct | ctggttttct | aaactcttca | gctgtggccg | agacggaggt | 60 |
| gtcatgggct | gggagagagg | ctgggtgcat | ttttgaaatg | catgtcattt | ttgggttgcg | 120 |
| tttgaaggtt | tcnccaaacc | ctctgagcac | gagaaacaca | atcactancc | tcgggtttaa | 180 |
| ccttgggccc | tccgtgtgct | cctagcctcc | tntcaggctc | cctcccaggc | atggctgcna | 240 |
| ggctgggaag | gccccagagt | cagcccaagt | ggcatgggtn | cagcttcagc | ttcatgtctg | 300 |
| cttttctttt | aggatgtata | gtttcccctc | tgtttgctgg | aaggcacctt | atatccagtg | 360 |
| gggttaaata | aaggtagcca | gaccccggc | tggggtgcta | ccgccagtgc | ccagctaatg | 420 |
| acgcatnnnt | tcag | | | | | 434 |

<210> SEQ ID NO 96
<211> LENGTH: 70
<212> TYPE: DNA
<213> ORGANISM: Homo sapiens

<400> SEQUENCE: 96

| | | | | | |
|---|---|---|---|---|---|
| gtgagcccct | tgggagagga | tggcccatgt | gggggactgc | acgcagacgc | cctggctccc | 60 |
| cgtcctggtg | | | | | | 70 |

<210> SEQ ID NO 97
<211> LENGTH: 722
<212> TYPE: DNA
<213> ORGANISM: Homo sapiens
<220> FEATURE:
<221> NAME/KEY: misc_feature
<222> LOCATION: (1)..(722)
<223> OTHER INFORMATION: n is a, c, t or g

<400> SEQUENCE: 97

| | | | | | |
|---|---|---|---|---|---|
| gtaagtggtc | tgagccccctt | accccacag | caccctcatc | ctcatgatgg | ttggactgtt | 60 |
| tcttggcctc | ttcagctgta | aaatgggaat | gctgatcata | gtccctcctc | cacagggttc | 120 |
| ttctgagggt | gaaatgaaac | caggcctgca | aagcacagaa | ctctgcccca | ggctgaagtt | 180 |
| acattgattt | cgttggtagc | tcccttcata | ggtctcatg | gatataaacg | ttcttgattg | 240 |
| cttgtttgtg | gtgtgataca | cacagccctg | tgtctatgtg | atgagctcat | gcttgggggc | 300 |
| cgcgcagcta | agaaagactt | ggaagactca | gaccctacc | cccatcctcc | tggacacgcc | 360 |
| ggtgttctga | ggagccactg | tattagaggc | tcagtggggg | acagggggcgc | ctcctccatg | 420 |
| accttggcaa | gtgcgttgat | gaggagaact | canagcaggc | cttgatggtg | ggatggggct | 480 |
| tggccagcag | gggtgaaggc | aggtggttc | tagtgggggc | tggccgtgcc | cangtggatc | 540 |
| aaccaggagc | cactggagac | ttaacagcag | tgagcactna | caagcggcac | cttcccagac | 600 |
| cgagccccca | gcagagcccc | caccgcaggg | cacccccttc | ctatgtcaac | cttggggtct | 660 |
| tgcaggagtc | acatgtgttt | ctaaggaggt | acggaggcca | caacacccccc | ctttgttggc | 720 |
| ag | | | | | | 722 |

<210> SEQ ID NO 98

<211> LENGTH: 123
<212> TYPE: DNA
<213> ORGANISM: Homo sapiens

<400> SEQUENCE: 98

```
gtgtctctga tgtgctcagc ccgagcggaa tactcaaact gcggtgagaa cgagtactac    60
aaccagacta cggggctgtg ccaggagtgc cccccgtgtg ggccgggaga ggagccctac   120
ctg                                                                 123
```

<210> SEQ ID NO 99
<211> LENGTH: 740
<212> TYPE: DNA
<213> ORGANISM: Homo sapiens

<400> SEQUENCE: 99

```
gtaaggaccc agccctcctg gagcctggtg cgctctcagg ggaggcctcc tgcttgtggc    60
attgttgccc tgagcctgcc ttgctgtgtg aggggatgcc agggtatatc aaaccagccg   120
gtcacgctcc ctggacgttg agattgatgg caagagctgc cgtgagccca ggaatggcac   180
tcaccagcta agcattcata acagattttt tcaggagttc tgaaatgttt ttaaaggatc   240
actttcccac tctaccctga ttaaatgagc gtcagatcat ctgattggaa gcaggattga   300
aatattctcc agtactagta cattttttcc tgagtgctgc atctccctcc gcctctgggc   360
aagctaagcc tgagtgttct gttcagcact aagggaaacc tccggggttt cagtgtccgg   420
ttcttgtagc aagctgagga aagtcagatg ccaagtgcta cctgcactgc ctgggcattc   480
cagcagctcg ctgaattcat ctcggggagg ctcagaaaag gggcagcatc tggagcctga   540
gagtggcgag gagagggggca agcccagagc atgagctggt tcctgggggg ttttgcagtt   600
aggacaactc aggaaaccaa ggcccggcaa gagtagcttc tggagacagc tggcacgtca   660
ctgcccaagg actgtgggcc gagtccgtat ggtttggctg ctgcactcac ctgtgtcccc   720
tgtcctcttt ccctggacag                                              740
```

<210> SEQ ID NO 100
<211> LENGTH: 182
<212> TYPE: DNA
<213> ORGANISM: Homo sapiens

<400> SEQUENCE: 100

```
tcctgtggct acggcaccaa agacgaggac tacggctgcg tcccctgccc ggcggagaag    60
ttttccaaag gaggctacca gatatgcagg cgtcacaaag actgtgaggg cttcttccgg   120
gccaccgtgc tgacaccagg ggacatggag aatgacgctg agtgtggccc ttgcctccct   180
gg                                                                  182
```

<210> SEQ ID NO 101
<211> LENGTH: 1169
<212> TYPE: DNA
<213> ORGANISM: Homo sapiens
<220> FEATURE:
<221> NAME/KEY: misc_feature
<222> LOCATION: (330)..(1163)
<223> OTHER INFORMATION: n is a, c, t or g

<400> SEQUENCE: 101

```
gtaagcacag gccctcctgg caaaccctgg catgctttct gcagaaaacc ccgaggggct    60
acgggcaagg accttgggaa cagggttcat ggatactgca ggcctcggtg cagccgcaca   120
cctggccttg gtcccatccc acaaggagca gcatccagga cggagagtcc tggcccctcc   180
```

```
ggtggacagg cagcccatca ggctctgcct ctgtgtctcc taagtggcca ttaaccatca    240
taatatcttc tgaccaccaa aaggaaacaa attgcttgaa tacttacagt gcagtagccc    300
atgtgaaaca ctttgggaaa aagaaaactn naatttnatg caaaaagcag tattttnagt    360
attctggnaa cactctggnn aanctactaa taanntanat ntgagaaaag aaatatnant    420
gangagatta tgannncgaa gnnaagnnan gnanaancan annaggntnn agaaaatgag    480
gttgnnaang antnataana tagnacanng ntgatatnca tnggaaagta aacngcntga    540
gnannagtga tttgtgatng ccagggtatt cntngaggga aaacangact attggancag    600
anngtgngga aaggnacaaa cgntgtntna ncataganaa nntagagttg ntgggtgggc    660
attnnaanna gcnggtaaag aatagcttgn aagtngncaa ggggtnccag aggcaannnt    720
aatgcctata natcccataa gnntgcaggc tantggngan ggtgctnaca aagagcatgt    780
tcctcctcca ggaaggtctg gccttngttg gtgtnacccc tggggggcta ancaggcccnt   840 acatgtgggg gcacagggat atttctggtg natgatgtga tggcacacac actaaacaca    900
gccaccagag agaggaacca gaaagggggct gagatcaaaa gaaaggccca cgttggcagc    960
tcaatattgt taaaagaatg ctccatttca agacaggctg aaaccccaag gaaactgagt   1020
ggacagagca ggtgactgag tgggcgtggc ctcatgcccg acttgattgt gggcctgcag   1080
actggccacc gtgctctctg caccagtccc tgcctgtgtg ctgtccagct cacctgtcta   1140
ctgttttgtc cttgtgctct ccnccgtag                                    1169

<210> SEQ ID NO 102
<211> LENGTH: 86
<212> TYPE: DNA
<213> ORGANISM: Homo sapiens

<400> SEQUENCE: 102
ctactacatg ctggagaaca gaccgaggaa catctatggc atggtctgct actcctgcct     60
cctggcaccc cccaacacca aggaat                                          86

<210> SEQ ID NO 103
<211> LENGTH: 484
<212> TYPE: DNA
<213> ORGANISM: Homo sapiens
<220> FEATURE:
<221> NAME/KEY: misc_feature
<222> LOCATION: (300)
<223> OTHER INFORMATION: n is a, c, t or g
<221> NAME/KEY: misc_feature
<222> LOCATION: (307)
<223> OTHER INFORMATION: n is a, c, t or g

<400> SEQUENCE: 103
gtgagtgtct ttgtccttcc accagcacgg tatttgttca ggcacggatc tctttcacta     60
cagagggtgt aggaaagagc cggtcctggc acctggacaa ggtgaatcac agtaacagca    120
ctagtgaaag tgctcctgtg gcctgtccag gcaggtctat gaagggaggg gcgtttgcca    180
catctgagcc ttgagtcaga ggctgaggtt ctagtgcagg ttggccacca gctacctgac    240
aagtcactta acctccatga gcctcggttt tctcatcggt aatatggggg tgaagaaagn    300
acaatancga tgactctttta gggttcatta aacagtctaa gaaatacaaa tatttagctc    360
ccctcagcca tcactgcctc aggcccattc atgatcatga atccagatcc atgagctctg    420
tggcagcgtg ctttgaaggt ggagcttctc tggatcattt gagggactct attttgcctt    480
gcag                                                                 484
```

<210> SEQ ID NO 104
<211> LENGTH: 87
<212> TYPE: DNA
<213> ORGANISM: Homo sapiens

<400> SEQUENCE: 104

```
gtgtgggagc cacttcagga gcttctgcca acttccctgg cacctcgggc agcagcaccc    60
tgtctccctt ccagcacgcc cacaaag                                        87
```

<210> SEQ ID NO 105
<211> LENGTH: 799
<212> TYPE: DNA
<213> ORGANISM: Homo sapiens
<220> FEATURE:
<221> NAME/KEY: misc_feature
<222> LOCATION: (325)..(642)
<223> OTHER INFORMATION: n is a, c, t or g

<400> SEQUENCE: 105

```
gtgaggaggg tgctcaggta tcgatcacct ggagttaggt ggtactcgga tgaaagctca    60
gaagaggaga ggaaatgatc atgagtgatg attatggtgc gcttccccac ctggcctcac   120
ctccctaatg taattgaatg acatgttgcc ccccgtgcag gaagtcatta tatctgcaat   180
cagagttgat ccctctatgg gtgtcctggg accgctggga ggtgctggtg gtgaaggcgg   240
gggcatagcg gcaggtggac agcacaggca gctgcaagcc cggccaggag gagagaccag   300
gcgtcctggg ctttggtttg gccgngagtt aacagcaatt ctatcactgg ttttcatata   360
aacatgctga ccatagcact ttaatattaa cttgcanaan gtncattttc attctncctt   420
aaccagggaa gangggatcg nggaggaccc caangtttan tntgcctctc acanttagnc   480
ccccacntgg cttgncntna aggttgccaa agcagtagna gcgagaagca agctcccctta   540 ggaacaatna ggtancccca gaaaaagtct gganaggcca agtctgaggg cagcgagcag   600
gggttgtggg cagtcctggt ctggcagcca aaaccagcgc gnaggatttg gttctcagtc   660
taagcaagca cctcagattt cagggttccc tgaaagcatc ccaggggcag ggccattgct   720
tccaggggcc ggagtcctgg agggaagacc agcagggatc ctgagctctg ggtcattcat   780
gccttctctc cacccacag                                                799
```

<210> SEQ ID NO 106
<211> LENGTH: 126
<212> TYPE: DNA
<213> ORGANISM: Homo sapiens

<400> SEQUENCE: 106

```
aactctcagg ccaaggacac ctggccactg ccctgatcat tgcaatgtcc accatcttca    60
tcatggccat cgccatcgtc ctcatcatca tgttctacat cctgaagaca aagccctctg   120
ccccag                                                              126
```

<210> SEQ ID NO 107
<211> LENGTH: 96
<212> TYPE: DNA
<213> ORGANISM: Homo sapiens

<400> SEQUENCE: 107

```
gtgacggccc ccatgcgccg gtgccctgcc tcctggactc tccgtcaact cccctgtcg    60 gagagcctgg ctgctcactc cctcctctct ccccag                             96
```

<210> SEQ ID NO 108
<211> LENGTH: 75
<212> TYPE: DNA
<213> ORGANISM: Homo sapiens

<400> SEQUENCE: 108
cctgttgcac cagccacccg gggaagagcg tggaggccca agtgagcaag gacgaggaga    60
agaaagaggc cccag    75

<210> SEQ ID NO 109
<211> LENGTH: 243
<212> TYPE: DNA
<213> ORGANISM: Homo sapiens
<220> FEATURE:
<221> NAME/KEY: misc_feature
<222> LOCATION: (190)
<223> OTHER INFORMATION: n is a, c, t or g

<400> SEQUENCE: 109
gtctgtgaac cagggcttcc acacaccatg tgcacggtgc ccatctctgg gtggagggcg    60
ttcccagaag cagcctcctc gctgcttctg ctctcacatg ctgaaccata ctgtgcttac   120
cgtggggtgg tgccacacag acaccgggca gctctgccca acaggaagag cagggttggg   180
ctgagcgcan agccatgagc caattctaac tcctatctcc caacctccc catttccctg   240 cag   243

<210> SEQ ID NO 110
<211> LENGTH: 73
<212> TYPE: DNA
<213> ORGANISM: Homo sapiens

<400> SEQUENCE: 110
acaacgtggt gatgttctcc gagaaggatg aatttgagaa gctgacagca acttcagcaa    60
agcccaccaa gag    73

<210> SEQ ID NO 111
<211> LENGTH: 1174
<212> TYPE: DNA
<213> ORGANISM: Homo sapiens
<220> FEATURE:
<221> NAME/KEY: misc_feature
<222> LOCATION: (64)..(752)
<223> OTHER INFORMATION: n is a, c, t or g

<400> SEQUENCE: 111
gtatgtggaa gcccccacac caagctgaac tggggtcctg tggatcctga gcagggaggg    60
gttnccaggg tgcagccgag tgaactgaca ggctagcctg ggacactatg gggacgttcg   120
gcgacagaca gtccccacca cctctttgct gactggcagg ggtcaggtgg tgtgaggagc   180
ctgtggaaac agctgcctgc tgctctcggg tcaggcccct gtccctgcat cctgccaaat   240
tccctgggcc ttcctcctta acatccgaat tcctcatgcc ccttctccag actgggaggg   300
cagaacataa agccaaggat gcatgcctgt tgcggccaac acaccagtac cacccgtgcc   360
ggtgccagta ctgctgccac cgtaatgctg gtaacaaccg tggtgatgac ggctaacagc   420
atttggtgcc tactgcccac caagtgctgg gctagggctg tgaacacatc ctnccttcca   480
ccagcccang agcaaggtgc ttggaatcat ccctggttat aggaatacca cactgaggta   540
tggaagttgt cactcgccca aagtcacaca ctagtgaaca canggcttgg ggtccgaagt   600
ccangctccc aangagccac atgggngntaa anaggtnagn cagggtcacc cccctaagtt   660

```
ccaagagggg ggcttttcna ggcacaaagg gttccattna ggttcccttt tcaatgncttt      720 ccagagagcc agcatggatt tcagcgccag cngcatccaa tctgtttgct ttaacatgaa       780
gacaccagtt gaacttgggt gcttactggg attaaataca gagatctagg acatattcaa      840
tgaaccttca cggagcatcc attgtgtgtc aggtagcagg gaaggagagg cccgtggatg      900
cctcccaccc gcagtggcag ccccagcccc ttagacgcct gcaggtcacc caccacggac      960
ttgtttgttt ggaaagaagc aggaagccac cggtgtatgt ctcgtctcat gtccctggt      1020 cccgtgccca caaggtgccc agtaaacacc tgaaaaacaa gtcattgccc cccactgtcc     1080
acagctgggc aatggacaag ttcaccacag agaacttgt cagggctgca gcccccccag      1140
gcactgctaa tgaccatcgc tcttgttttt gcag                                 1174
```

<210> SEQ ID NO 112
<211> LENGTH: 160
<212> TYPE: DNA
<213> ORGANISM: Homo sapiens
<220> FEATURE:
<221> NAME/KEY: misc_feature
<222> LOCATION: (19)
<223> OTHER INFORMATION: n is a, c, t or g

<400> SEQUENCE: 112

```
cgagaacgat gcctcatcng agaatgagca gctgctgagc cggagcgtcg acagtgatga       60
ggagcccgcc cctgacaagc agggctcccc ggagctgtgc ctgctgtcgc tggttcacct      120
ggccagggag aagtctgcca ccagcaacaa gtcagccggg                            160
```

<210> SEQ ID NO 113
<211> LENGTH: 226
<212> TYPE: DNA
<213> ORGANISM: Homo sapiens
<220> FEATURE:
<221> NAME/KEY: misc_feature
<222> LOCATION: (210)..(225)
<223> OTHER INFORMATION: n is a, c, t or g

<400> SEQUENCE: 113

```
gtgaggctcc tgcaggtgcc atgatgagct gtgagatgtg gctccctcac agccgcaagg       60
actaaaactt tcttattgaa tcagctctcc tgcaagacgg ggtgtttctc ccagaagtcc      120
aagataggag acctggacag tgacaagttc acagcaagat agtcaaaagg gaaaaaaacc      180
ctttcgtttt tgagttttgt ttttttttttn ggngatgana gnctng                    226
```

<210> SEQ ID NO 114
<211> LENGTH: 61
<212> TYPE: DNA
<213> ORGANISM: Homo sapiens

<400> SEQUENCE: 114

```
attcaaagcc ggaggaaaaa gatcctcgat gtgtatgcca acgtgtgtgg agtcgtggaa       60
g                                                                      61
```

<210> SEQ ID NO 115
<211> LENGTH: 309
<212> TYPE: DNA
<213> ORGANISM: Homo sapiens
<220> FEATURE:
<221> NAME/KEY: misc_feature
<222> LOCATION: (8)..(204)
<223> OTHER INFORMATION: n is a, c, t or g

<400> SEQUENCE: 115

```
agagtggnng aagagngaag ggaggngaaa aggggngag ngagggaagg aggngggaan      60
nnggagtgag gggggggaagg ggnagagngg gnggnagngn gnggngagng gganagngaa   120
agnagtgaga ngggaaggna nagngagnag gggnnangag aaagngggag ngtaggnggc    180
gatgngnnng gtngaaatat tnanagaaat tttttcaaat aatttttatt tcatttaaat    240
aatttttcag tgttgacctt ctattgactg tgacttgcaa catctaactg tggccattgg    300
tgtctgtag                                                            309
```

<210> SEQ ID NO 116
<211> LENGTH: 2781
<212> TYPE: DNA
<213> ORGANISM: Homo sapiens
<220> FEATURE:
<221> NAME/KEY: misc_feature
<222> LOCATION: (528)..(2756)
<223> OTHER INFORMATION: n is a, c, t or g

<400> SEQUENCE: 116

```
gtcttagccc cacggagctg ccatttgatt gcctcgagaa gactagccga atgctcagct     60
ccacgtacaa ctctgagaag gctgttgtga aaacgtggcg ccacctcgcc gagagcttcg    120
gcctgaagag ggatgagatt gggggcatga cagacgcgcat gcaactcttt gaccgcatca   180
gcacggcagg ctacagcatc cctgagctac tcacaaaact ggtgcagatt gagcggctgg    240
atgctgtgga gtccttgtgt gcagacatac tggagtgggc gggggttgtg ccacctgcct    300
cccagccaca tgctgcatcc tgaaaagcat gcctgtgggc tgtcctccca ggacaagcca    360
aggatccaac gagggctctg gagctgtgag tggtgccaaa agactgccaa gaatcaaggc    420
ttttgtgata tgtcaccgta tgccttagga tgttcaagga gccagacgaa ataaggcctg    480
tcttccaatt taaccaaaga taaggacta gagccgggat acttttcanat gctcgcctgt    540
acctcaccag gcagagtaaa tatctactca ctcatacagc cagcccacca gcccaccatt    600
aactcactga acaatgagac aatgtngagg actcaaatga atcaaacccc gtgggaatga    660
cagantgaag aatctggtcc ctgtctttaa ggagtttgca ctccagtaga agacagaagg    720
aacgtatgtt tacaaaccac ttcactggaa gacgtcaaac aagctgaatg aagggcgct    780
tagaaaacgt taatagaagt tctaagcggg agatgactcc ctactgggat gatgaaggat    840
ggcatcctag tgaagaagca gctcaaacat tttgataaaa tggcaacaaa atgcagacac    900
cctgctccag gtattatttc aggtttagta caagtctgtt aatacctat gtggtttcat     960
taggataact ttttacctat ccttgaggtc atccatattc ttacaggcct tccagtcaat   1020
aatggaagag ctcactctat acaaaaccaa tatgcaaggc atgtgtttgt ccaagcaatt   1080
ggatgtgtgc agtagccaat ttcatttact gcattactct ttggcctggg aaccctgtgg   1140
tctgcactac atgtgaatgg ccttccactt caagtcttag gcagatttga ccttttaggg   1200
gcagcaatgc tgaaggacac agcaatttaa attataatgt gtcaggctgt gttttcactt   1260
caaacatgta tgagtagtca gctgtaatta gagaaatgat gacttcctaa gagttcagcc   1320
acgcataatt ctagatttca agagcatcta agacttgtgg attagcctca tggcatgaga   1380
gtttcagact cagccttctg agccagtcag ggaaagtgga gttctgcagc gcaaatgaga   1440
gcctgggctt ggtgtcgagg gagctggctt ctagttgtgc cacccttgggc cttgtctttt   1500
cctctctctg cctcagtttc tcgtctgcca atgagatgtt agttagtgat tctataattg   1560
gggcaggtag ggttcaggtg agcaaaaaga aagtggagct ataggaaatg ccaggccttt   1620
```

-continued

```
gaggtgctct atggaagtca acacagtgtg gtttgtccat ttaaatggga ataaaaacag    1680
aaaaactcag acttggcatt ttcacaataa ctgcaatggt ttgacataac atttataggc    1740
agaaagttaa taaactggca ttgttcttgg catattattg tactatccct gtaactgcca    1800
agagctcagg agccaggcta gtgatcacac caggggttag agttcactgc tgaactccct    1860
gatggcaggt ctgtgtttat tactacatta aaacaaagtc tctgacttat aaagcgaggt    1920
cgtaaaaatt acaagttgca tgactgaaaa aatgctttag ggggaaaatc agtcatatct    1980
ttaacaccaa caagcaattt cccaccaacg aatgtagtac atactgtgag aggatcataa    2040
tgaggtcctg aatatttaat atcatcattt actgtgtctg tttgctgctg tttttcgaac    2100
ctatttggtt taccctgcaa gctaaatact ccacggcaga ncttaattat ccttttaatt    2160
cctctttgaa atcctgtggt gccccttcc ccctgccttg tgatgatgat gagtgagtct     2220 cccttaatt agactgcaaa tgtcacttgt gatgagtgtg ccattccagg ataacagctt     2280
gcaccctcct cagaatgttt tcagcgaaag agtggggtgg ctgttctctg ctcctggtgc    2340
tttggcctca tttcacacta ttagaattct ggggctgtaa ggccagccag tgtcagctca    2400
tgttccattg gctctccacc tgccattttt agggagctat tccttatata gttacaaatt    2460
cccttgtcat ttacttattt ggaaacatgg gatttactct gacaagcttt agcctatgtt    2520
atgggattca gaacaatgag atcataataa ttctcactga ccaaagctgg gactccatcc    2580
tgccattttt gtgtggagat attcataatt ctgcaatact ttaaaacatt tagaaaacac    2640
cccagggtag gtctgtggcc cttanacagt gaaagtctta attggcaata ttattttgc     2700 taattctgga tatatataac nnattatatt tataaatctc aataaacccc atttantaaa    2760
aaaaaaaaaa aaaaaaaaa a                                               2781
```

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer that can be used to
      diagnosis ED.

<400> SEQUENCE: 117

```
aaaaagtaac actgatccta ttt                                              23
```

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer that can be used to
      diagnosis ED.

<400> SEQUENCE: 118

```
agaaagcagg acctcctgg                                                   19
```

<210> SEQ ID NO 119
<211> LENGTH: 17
<212> TYPE: PRT
<213> ORGANISM: Homo sapiens

<400> SEQUENCE: 119

```
Leu Val Val Pro Ser Glu Gly Leu Tyr Leu Ile Tyr Ser Gln Val Leu
 1               5                  10                  15
```

Phe

<210> SEQ ID NO 120
<211> LENGTH: 17
<212> TYPE: PRT
<213> ORGANISM: Homo sapiens

<400> SEQUENCE: 120

Leu Leu Val Pro Thr Ser Gly Ile Tyr Phe Tyr Ser Gln Val Val
 1               5                  10                  15

Phe

<210> SEQ ID NO 121
<211> LENGTH: 17
<212> TYPE: PRT
<213> ORGANISM: Homo sapiens

<400> SEQUENCE: 121

Leu Ala Leu Pro Gln Asp Gly Leu Tyr Tyr Leu Tyr Cys Leu Val Gly
 1               5                  10                  15

Tyr

<210> SEQ ID NO 122
<211> LENGTH: 17
<212> TYPE: PRT
<213> ORGANISM: Homo sapiens

<400> SEQUENCE: 122

Leu Val Ile Asn Glu Ala Gly Leu Tyr Phe Val Tyr Ser Lys Val Tyr
 1               5                  10                  15

Phe

<210> SEQ ID NO 123
<211> LENGTH: 17
<212> TYPE: PRT
<213> ORGANISM: Homo sapiens

<400> SEQUENCE: 123

Leu Thr Val Lys Arg Gln Gly Leu Tyr Tyr Ile Tyr Ala Gln Val Thr
 1               5                  10                  15

Phe

HYPOHIDROTIC ECTODERMAL DYPLASIA GENES AND PROTEINS

This application claims priority from U.S. Provisional Application No. 60/092,279 filed Jul. 9, 1998 and No. 60/112,366 filed Dec. 15, 1998.

ACKNOWLEDGEMENT OF GOVERNMENT SUPPORT

Some of the work described in this patent application was funded by a grant DE11311 from the National Institute of Dental Research, grants HL-49953 and AR-45316 from the National Institutes of Health and a grant from the National Foundation for Ectodermal Dysplasia. The government may have certain rights in this invention.

FIELD OF THE INVENTION

This invention relates to nucleic acid sequences and proteins involved in hypohidrotic ectodermal dysplasia (HED) and hair follicle induction.

BACKGROUND OF THE INVENTION

Hereditary ectodermal dysplasia is an inherited disorder that affects the development of ectodermally derived structures, such as the hair, teeth and sweat glands. The hidrotic form of the disease is characterized by poorly developed teeth and hair. The anhidrotic or hypohidrotic form of the disease further affects the development of sweat glands, which interferes with the ability to sweat, and the maintenance of thermoregulatory homeostasis. Both X-linked and autosomal dominant and recessive forms of the disease have been described.

X-linked hypohidrotic ectodermal dysplasia (XLHED; McKusick's number 305100), the most common form of the ectodermal dysplasias, results in the abnormal development of teeth, hair and eccrine sweat glands. Identification of the gene that is defective in this disease would help explain the molecular basis of XLHED, as well as the molecular mechanisms involved in normal tooth, hair and eccrine sweat gland development. Identification of the gene would also permit mutation testing for XLHED in potentially affected males and carrier females.

Heterozygote carriers of XLHED may have minor or moderate degrees of hypodontia, hypotrichosis and hypohidrosis, although many show no obvious clinical manifestations. This clinical variation, presumably caused by random X-inactivation (Lyonization), makes accurate diagnosis of carrier females difficult. Although indirect testing for carrier status is possible by linkage analysis in informative families (Zonana 1993), carrier detection by this method is impossible in families with single affected individuals, male or female, whose disorder may be the result of a de novo mutation. Detection of mutations within the EDA1 gene would also be advantageous in families with only a single affected sibship, because a rarer autosomal recessive form of the disorder (ARHED) is clinically indistinguishable from XLHED in affected males (Munoz et al. 1997).

A gene identified as EDA1 has been isolated by positional cloning (Kere et al. 1996). A single 858 bp cDNA, representing a full length transcript composed of 2 exons, was identified from an adult sweat gland cDNA library. In situ analysis showed that the EDA1 gene was expressed in hair follicles and the epidermis of adult skin. The putative gene product is a 135 amino acid protein, which has no clear homology to other proteins (see U.S. Pat. No. 5,700,926). The protein is predicted to contain a single transmembrane domain, and fractionation studies of transfected cell lines showed that the protein product is localized to the plasma membrane (Ezer et al. 1997). Yeast artificial chromosomes (YACs) containing at least a portion of the human EDA1 gene were disclosed in U.S. Pat. No. 5,556,786.

A syndrome similar to HED, with anhidrosis and absence of sweat glands, is known in the mouse, in which the mutant gene is called Tabby (Ta). Consistent with the map position in humans, the Ta gene has been mapped in the syntenically corresponding region in the X chromosome of the mouse (Brockdorff et al. 1991). Other murine forms of the disease include those found in the downless (dl) mutants, in which the disorder is not X-linked.

SUMMARY OF THE INVENTION

The present invention has been made possible by the discovery that there are previously unidentified alternative transcripts of the EDA1 gene. The inventors recognized that while the full length of the EDA1-I cDNA was 858 bp, a predominant 5–6 kb transcript was detected in several human tissues by Northern analysis. Mutation screening of 173 unrelated families with XLHED showed that only 7% of the families had likely mutations within exon 1, and none had variants within exon 2. Moreover, cDNAs from the homologous murine gene, Tabby (Ta), were found to include alternative exons.

The present invention includes an EDA1 cDNA splice-form (Seq. I.D. No. 1) that is homologous to the Ta cDNA (Seq. I.D. No. 3), and codes for a second isoform of the EDA1 protein (isoform II or EDA1-II). Nearly all of the mutations associated with XLHED are located within the exons identified in this new splice-form. These results show that EDA1 isoform II is essential for hair, tooth and eccrine sweat gland morphogenesis. In addition, the identification of the additional exons permits direct molecular diagnostic testing for XLHED by mutation analysis.

Also disclosed is the nucleic acid sequence encoding the human gene EDA1-II sequence (Seq. ID. NOS. 5–11), which is predicted to encode a 391 amino acid protein (Seq. I.D. No. 2). The EDA1-II gene is predicted to encode a protein that is related to the TNF family of proteins, and acts as either a membrane-associated or soluble ligand. The biologically active domains of the EDA1-II protein are within approximately the C-terminal 240 amino acids (and particularly residues 133–391, and especially residues 239–391 of EDA1-II) and includes a Furin recognition sequence, a Gly-X-Y repeat, and a region of structural homology to TNF proteins. This predicted active region is unique to this isoform, with none of the amino acids included within the previously described EDA1 sequence. The DNA sequence that codes for this isoform (Seq. I.D. No. 1) is also unique.

The EDA1-II protein is an essential component of a signaling pathway that is required for the normal development of hair follicles, teeth, sweat glands and mammary glands. A form of the protein is present in humans, mice, cow and dog, and is likely to serve the same or nearly identical roles in each of these organisms. The invention includes the use of the human EDA1-II gene sequence, as it applies to the use of commercial and clinical diagnostic testing for ectodermal dysplasia (ED). The invention also includes use of an EDA1-II gene sequence for the production of EDA1-II protein, as a therapeutic substance stimulating the growth of hair, teeth, skin, and sweat glands.

Potential medical or cosmetic benefits of EDA1-II include the stimulation of hair growth, including cases of alopecia (balding) or skin grafts. As such, EDA1-II may be applied as a purified protein or nucleic acid (DNA or RNA), delivered as topical substance, or injected into the skin, alone or in combination with a pharmaceutical carrier.

The EDA1-II isoform (or active subsequences thereof, particularly the C terminal 240 amino acid residues, or residues 133–391, particularly 239–391), may also be used as a stimulant for tooth growth, either in cases of tooth loss or of natural absence of teeth. The protein may be used to stimulate tooth growth in humans directly, or alternatively in tissue culture (artificial) conditions, with subsequent introduction of teeth into humans or other organisms. The EDA1-II protein or EDA1-II gene may also be useful for the stimulation of eccrine sweat gland development, for example in individuals for whom the normal sweating mechanism is compromised by disease or surgery.

The protein may also be used to stimulate the growth of mammary epithelial tissue, either for reconstructive or cosmetic purposes. Alternatively, methods that block the production of the protein, for example antisense or antibody approaches, may be useful for inhibiting breast epithelial cell proliferation. Blocking EDA1-II activity may provide an effective therapeutic approach to slow or to inhibit the spread of breast cancer malignancies. The EDA1-II gene and gene product itself may also be useful in promoting or maintaining differentiation of breast epithelium.

The present invention also provides an isolated human nucleic acid molecule which may be able to correct the cellular defect characteristic of HED, including XLHED. It is shown that XLHED patients carry mutations in the genomic copies of this nucleic acid molecule. Orthologs of the disclosed nucleic acid molecule from other species are also provided, which may be able to correct the effects of the mutation. Such homologous proteins may have 95% or 98% identity to the EDA1-II isoform. Also included are DNA sequences that code for EDA1-II, including probes and primers for these DNA molecules.

More specifically, the invention provides an isolated human cDNA, herein referred to as the human ectodermal dysplasia gene, isoform II sequence (EDA1-II) cDNA for correcting or improving abnormal biochemical activities of cells in which it is expressed, for example in human cells derived from XLHED patients. Also provided by this invention is the amino acid sequence of the protein ligand encoded by this cDNA, and DNA and amino acid sequences of receptors (referred to as murine downless, dl, and human DL) for the ligands to bind as agonists. Murine and human cDNA and amino acid sequences for the dl (murine) and DL (human) receptors are provided in Seq. I.D. NOS. 12, 19, 18 and 17.

The invention also provides an isolated human nucleic acid molecule which may be able to correct the cellular defect characteristic of HED, including non-X-linked, autosomal forms of the disease. More specifically, the invention provides an isolated cDNA, referred to as the DL gene, for correcting or improving biochemical activities in human cells derived from ectodermal dysplasia patients in which it is expressed. Also provided are the amino acid sequences of the proteins encoded by these cDNAs.

Having provided the nucleotide sequence of the human EDA1-II cDNA and the dl and DL receptors, correspondingly provided are the complementary DNA strands of these cDNA molecules and DNA molecules which hybridize under stringent conditions to these cDNA molecules, or their complementary strands. Such hybridizing molecules include DNA molecules differing only by minor sequence changes, including nucleotide substitutions, deletions and additions. Guidance about making such mutations, while maintaining biological activity of the proteins, is provided by the illustration of mutations that interfere with biological function. Further guidance is provided by comparison of the sequences from different species, which illustrate highly conserved sequences. Moreover, the disclosure of the dl and DL receptors permits the construction of a particularly convenient assay for determining whether a variant ligand binds to the receptor, and would be a candidate agonist or antagonist.

Through the manipulation of the disclosed nucleotide and amino acid sequences by standard molecular biology techniques, variants of the EDA1-II agonist, and the dl and DL receptors, may be made which differ in precise amino acid sequence from the disclosed proteins, yet which maintain the basic functional characteristics of the disclosed proteins, or which are selected to differ in some characteristics from these proteins. Variants can also be made which interfere with receptor action, and therefore act as antagonists.

Also comprehended by this invention are isolated oligonucleotides comprising at least a segment of the disclosed cDNA molecules or the complementary strands of these molecules, such as oligonucleotides which may be employed as DNA hybridization probes or DNA primers useful in the polymerase chain reaction. Hybridizing DNA molecules and variants of the EDA1-II cDNA and the dl and DL cDNAs may readily be created by standard molecular biology techniques. Such oligonucleotides may be used for detecting an enhanced susceptibility of an individual to ectodermal dysplasia. Specifically, the oligonucleotides of the present invention may be used for molecular diagnostic testing for XLHED and HED by mutation analysis.

Having provided the isolated human EDA1-II ligand sequence, and the mammalian dl and DL receptor sequences, this invention also includes genomic sequences from which these cDNAs are derived. The exon sequences of EDA1-II are shown in Seq. I.D. NOS. 5–11, and the exon/intron sequences of DL are shown in Table 5 (Seq. I.D. NOS. 94–116). Also provided by the present invention are recombinant DNA vectors comprising the disclosed DNA molecules, and transgenic host cells containing such recombinant vectors.

The present invention also provides methods for using the disclosed cDNAs, the corresponding genomic sequence, and derivatives thereof, and of the expressed protein, and derivatives thereof, in aspects of diagnosis of ectodermal dysplasia, and detection of carriers. One particular embodiment of the present invention is a method for screening a subject to determine if the individual carries a mutant EDA1-II gene or a mutant dl or DL gene. The method includes detecting the presence of nucleotide differences between the sequence of the individual's EDA1-II, dl or DL gene ORF compared to the EDA1-II, dl or DL cDNA or genomic sequence disclosed herein, or the presence of nucleotide differences between the individual's dl or DL gene ORF compared to the dl or DL cDNA sequence disclosed herein, and determining whether any such sequence differences will result in the expression of an aberrant gene product in the individual. The step of detecting nucleic acid sequence differences may be performed using several techniques including: hybridization with oligonucleotides (including, for example, the use of high-density oligonucleotide arrays); PCR amplification of the gene or a part thereof using oligonucleotide primers; RT-PCR amplification of the EDA1-II, dl or DL RNA, or a part thereof using oligonucleotide primers, and direct sequencing of the EDA1-II, dl or DL gene of the individual's genome using oligonucleotide primers.

In a specific embodiment, the oligonucleotides used for detecting a mutation in the EDA1-II or DL gene of an individual are selected from the group consisting of SEQ. I.D. NOS 20–29, SEQ. I.D. NOS 74–93 and SEQ. I.D. NOS 117–118. XLHED. In another embodiment, methods for detecting a mutation in an individual suffering from XLHED or an autosomal form of ectodermal dysplasia, are provided. Such methods involve incubating at least one of the oligonucleotides listed above with a nucleic acid preparation of the individual under conditions such that the oligonucleotide primer specifically hybridizes to an EDA1-II gene or a DL gene present in the nucleic acid preparation to form an oligonucleotide:EDA1-II gene or DL gene complex. This complex is then used to amplify the nucleic acid of the EDA1-II or DL gene defined by the oligonucleotide primer used. After this amplification, the presence or absence of mutations within the EDA1-II or DL gene complex are detected using any method known to those skilled in the art, such as SSCP, ASO, direct sequencing or dideoxyfingerprinting analysis. The presence of a mutation(s) indicates an enhanced susceptibility of the individual to ectodermal dysplasia.

The disclosed sequences have also been useful in the creation and study of mutations in the EDA1-II, dl or DL locus that affect biochemical activity of the protein, which in turn has yielded valuable information about the biochemical pathways underlying the disease, as well as information about epithelial mesenchymal signaling.

A further aspect to the present invention is a preparation comprising specific binding agents, such as antibodies, that specifically detect the EDA1-II, dl or DL proteins. Such specific binding agents may be used in methods for screening a subject to assay for the presence of a mutant EDA1-II, or DL gene. One exemplary method comprises providing a biological sample of the subject which sample contains cellular proteins, and providing an immunoassay for quantitating the level of EDA1-II, dl or DL protein in the biological sample.

The foregoing and other objects, features, and advantages of the invention will become more apparent from the following detailed description of several embodiments which proceeds with reference to the accompanying figures.

BRIEF DESCRIPTION OF THE FIGURES

FIG. 1 is a sequence comparison of an EDA1-II (EDA) (SEQ ID NO: 2) and Tabby (Ta) (SEQ ID NO: 4) proteins. Amino acid identities are indicated by an asterisk (*). The transmembrane domain is boxed. A vertical line designates the start of the protein sequence unique to isoform II. The Gly-X-Y domain is indicated by boldface type, with the 2-amino acid interruption indicated by shadowed lettering. A blackened circle is shown above two potential N-linked glycosylation sites, and three C-terminal cysteines are indicated by underlining and boldface type.

FIG. 4 is a comparison of the sequences of the central β-sheet of EDA1-II (amino acids 293–309 of SEQ ID NO: 2) compared with human tumor necrosis factor (Hu TNF) (SEQ ID NO: 119), lymphotoxin α (LTα) (SEQ ID NO: 120), lymphotoxin β (LTβ) (SEQ ID NO: 121), FAS (SEQ ID NO: 122), and CD40-L (ligand) (SEQ ID NO: 123) which are all members of the TNF family of proteins. One dot over a column indicates conservation across all sequences. Two dots over a column indicates the G(x)Y (glycine and tyrosine residues) identified in all the TNF related proteins.

FIG. 7 is a comparison of the sequences of the mouse dl (Seq. I.D. No. 19) and human DL (Seq. I.D. No. 17) amino acid sequences for the receptor protein. (:) denotes identical residues; (.) identifies conserved residues. The cysteine-rich region (residues 30–71) is boxed and shaded with cysteines in bold; the potential transmembrane domain (residues 190–211) is underlined. The open box (residues 410–431) identifies the potential death domain region.

SEQUENCE LISTING

Figure 2:
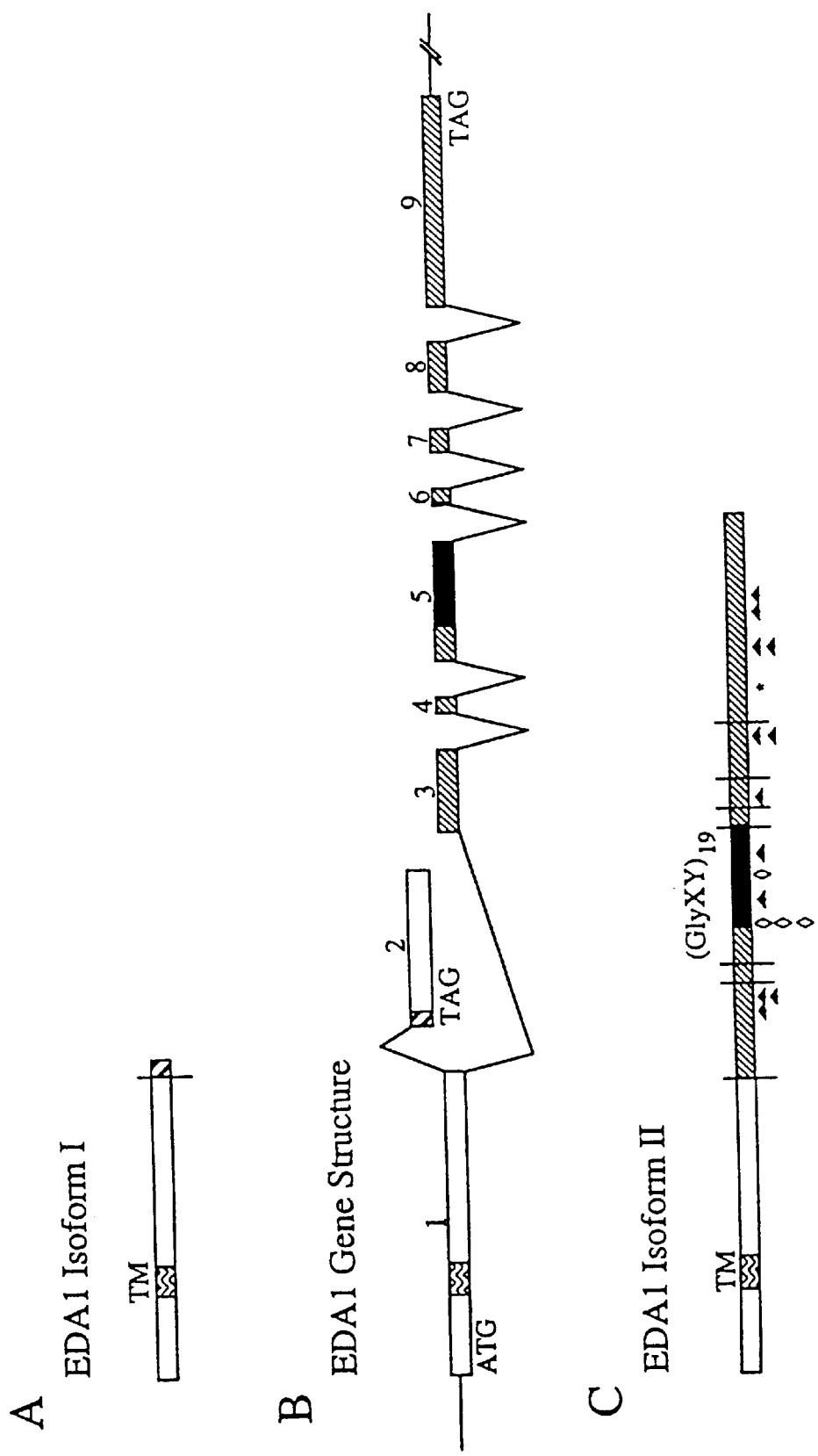
FIGS. 2A, 2B, and 2C show schematic diagram of the gene structure and predicted protein products of the EDAL isoforms I and II. The protein products of the two splice forms are depicted in panels A and C. The vertical lines separate protein regions encoded by different exons. Transmembrane ("TM") and collagen-like (Gly-X-Y) domains are shown. The relative positions of the mutations identified in the specification are depicted in panel C, with missense mutations indicated by blackened triangles, deletions indicated by unblackened diamonds, and a nonsense mutation indicated by an asterisk (*). Mutations in exon 1 are not included in this figure. The EDA1 gene structure is depicted in panel B, with the numbered boxes representing exons and the connecting lines representing intronic regions. The start and stop codons are indicated by ATG and TAG, respectively.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

Seq. I.D. No. 1 shows the cDNA sequence of the human EDA1-II, including portions of the 3' and 5' noncoding regions (GenBank Accession No. AF060999).

Seq. I.D. No. 2 shows the amino acid sequence of the human EDA1-II protein, which is an agonist ligand (GenBank Accession No. AAC36302).

Seq. I.D. No. 3 shows the cDNA sequence of Tabby (Ta), including portions of the 3' and 5' noncoding regions (GenBank Accession No. AF004435).

Seq. I.D. No. 4 shows the amino acid sequence of the murine Ta protein, which is an agonist ligand (GenBank Accession No. AAB88122).

Seq. I.D. NOS. 5–11 are the sequences of EDA1-II exons 3 (GenBank Accession No. AF060992), 4 (GenBank Accession No. AF060993), 5 (GenBank Accession No. AF060994), 6 (GenBank Accession No. AF060995), 7 (GenBank Accession No. AF060996), 8 (GenBank Accession No. AF060997) and 9 (GenBank Accession No. AF060998), respectively, with 3' and 5' flanking intronic sequences.

Seq. I.D. No. 12 shows the cDNA sequence of the mouse dl gene (GenBank Accession No. AF160502).

Seq. I.D. No. 13 shows the open reading frame of the mouse dl gene.

Seq. I.D. No. 14 shows the open reading frame of Seq. I.D. No. 1 (EDA1-II).

Seq. I.D. No. 15 shows the open reading frame of Seq. I.D. No. 2 (Ta).

Seq. ID. No. 16 shows the open reading frame of the human DL cDNA (GenBank Accession No. AF130988).

Seq. ID. No. 17 shows the amino acid sequence of the human DL receptor protein.

Seq. I.D. No. 18 shows the cDNA sequence of human DL, including the 5' and 3' UTR.

Seq. I.D. No. 19 shows the amino acid sequence of the murine dl receptor protein.

Seq. I.D. NOS. 20–21 show PCR primers used to amplify exon 5 of EDA1-II.

Seq. I.D. NOS. 22–29 show oligonucleotide primers that can be used for diagnosis of ectodermal dysplasia.

Seq. I.D. NOS. 30–33 show PCR primers used to screen a BAC library.

Seq. I.D. NOS. 34–45 show PCR primers used to clone the murine dl gene.

Seq. I.D. NOS. 46–73 show PCR primers used to clone the human DL gene.

Seq. I.D. NOS. 74–93 show primers used for mutation screening of the human DL gene using SSCP analysis.

Seq. I.D. NOS. 94–116 show the human DL exons 1–12 with partial flanking genomic sequences (GenBank Accession NOS. AF130989–AF130996).

Seq. I.D. NOS. 117 and 118 show oligonucleotide primers that can be used for diagnosis of ectodermal dysplasia.

SEQ ID NO: 119 is a partial amino acid sequence of human tumor necrosis factor (Hu TNF).

SEQ ID NO: 120 is a partial amino acid sequence of lymphotoxin α (LTα).

SEQ ID NO: 121 is a partial amino acid sequence of lymphotoxin β (LTβ).

SEQ ID NO: 122 is a partial amino acid sequence of FAS.

SEQ ID NO: 123 is a partial amino acid sequence of CD40-L (ligand).

DETAILED DESCRIPTION OF SEVERAL EMBODIMENTS

DEFINITIONS

In order to facilitate review of the various embodiments of the invention, the following definitions of terms and explanations of abbreviations are provided:

cDNA (Complementary DNA)

A piece of DNA lacking internal, non-coding segments (introns) and regulatory sequences which determine transcription. cDNA may be synthesized in the laboratory by reverse transcription from messenger RNA extracted from cells.

XLHED

X-linked hypohydrotic ectodermal dysplasia HED: Hypohidrotic ectodermal dysplasia, which can include both X-linked and autosomal forms of the disease.

EDA1-II Gene

A gene which codes for the EDA1-II protein, the mutant forms of which are associated with HED, particularly X-linked forms of the disease. The definition of an EDA1-II gene includes the various sequence polymorphisms and allelic variants that exist in the species in question.

EDA1-II cDNA

The EDA1-II cDNA is functionally defined as a cDNA molecule which, when transfected into a cell from an individual with XLHED, is able to restore the normal phenotype. The EDA1-II cDNA may be derived by reverse transcription from the mRNA encoded by the EDA1-II.

EDA1-II Protein

The protein encoded by an EDA1-II gene or cDNA, and which is believed to bind as an agonist to the DL receptor and activate signal transduction that promotes the development of hair follicles, sweat glands and/or teeth.

EDA1-II Biological Activity

The biological activity of the proposed secreted peptide (153–391) could be assessed by the intradermal injection or topical application of the protein to the skin or tails of newborn tabby mice. Functional protein activity would be detected by the induction of hair growth. Alternatively, the produced protein could be applied to or injected into the footpads of newborn tabby mice, with subsequent monitoring of sweat gland development. Another functional assay would be to apply or express the truncated protein in an in vitro tooth organ culture system, and then to determine whether developmental changes occur (which would not be expected in the absence of a functional variant of the protein). Any of these assays could be modified by using in vivo expression of the EDA1-II gene, and variants thereof, instead of applying/injecting purified proteins.

Mutant EDA1-II Gene

A form of the EDA1-II gene that does not encode a functional EDA1-II protein.

dl and DL Genes

A gene which codes for a dl or DL protein, respectively, which is believed to be a receptor for the Ta and EDA1-II protein, respectively. Mutant forms of the dl gene are associated with murine downless mutations. Mutant forms of the human DL gene are associated with HED, particularly autosomal forms of the disease. The definition of a dl or DL gene includes the various sequence polymorphisms and allelic variants that exist within and between species. The human DL gene is abbreviated DL, and the murine gene is abbreviated dl.

dl and DL cDNA

The dl and DL cDNA are functionally defined as cDNA molecules which, if transfected into and expressed in cells from some individuals (or patients) with autosomal recessive HED, restores the normal phenotype, or which are activated by binding to a Ta or EDA1-II ligand to promote development of hair follicles and sweat glands. The dl and DL cDNA may be derived by reverse transcription from the mRNA encoded by the dl and DL genes, respectively.

dl and DL Protein

A receptor protein which has a biological activity of the protein shown in Seq. I.D. NOS. 19 and 17. This definition includes natural allelic variants in the disclosed sequence, as well as the protein of any species, and variant peptides which retain the ability to promote growth of hair follicles and sweat glands, in species such as mouse, rat, chicken, rabbit, cat, and human, but in some particular examples the nucleic acid provided by the invention encodes dl and DL receptors of mammalian origin.

Isolated

An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Mammal

This term includes both human and non-human mammals. Similarly, the terms "patient" and "individual" includes both human and veterinary subjects.

Oligonucleotide

A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably Linked

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (Open Reading Frame)

A series of nucleotide triplets (codons) coding for amino acids without any termination codons. These sequences are usually translatable into a peptide.

Ortholog

Two nucleotide sequences are orthologs of each other if they share a common ancestral sequence, and diverged when a species carrying that ancestral sequence split into two species. Orthologous sequences are also homologous sequences.

Probes and Primers

Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 21 consecutive nucleotides of the human EDA1-II or DL cDNA or gene will anneal to a target sequence such as an EDA1-II or DL gene homolog (such as the Ta gene or a murine dl gene) contained within a genomic DNA library with a higher specificity than a corresponding primer of only 15 nucleotides. Thus, in order to obtain greater specificity, probes and primers may be selected that comprise 21, 25, 30, 35, 40, 50 or more consecutive nucleotides of the EDA1-II cDNA or gene sequences.

The invention thus includes isolated nucleic acid molecules that comprise specified lengths of the disclosed EDA1-II, dl or DL cDNA or gene sequences. Such molecules may comprise at least 20, 21, 25, 30, 35, 40 or 50 consecutive nucleotides of these sequences and may be obtained from any region of the disclosed sequences. By way of example, the cDNA and gene sequences may be apportioned into halves or quarters based on sequence length, and the isolated nucleic acid molecules may be derived from the first or second halves of the molecules, or any of the four quarters. In particular, the DNA sequences may code for a unique portion of the EDA1-II isoform (amino acid residues 133–391, as numbered in FIG. 1), or a ligand binding region of dl or DL.

Purified

The term purified does not require absolute purity; rather, it is intended as a relative term. Thus, for example, a purified EDA1-II protein preparation is one in which the protein is more pure than the protein in its natural environment within a cell. Preferably, a preparation of an EDA1-II protein is purified such that the protein represents at least 50% of the total protein content of the preparation.

Recombinant

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence Identity

The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences will be.

Methods of alignment of sequences for comparison are well-known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NBCI, Bethesda, Md.) and on the Internet, for use in connection with the sequence analysis programs blastp, blastn, blastx, tblastn and tblastx. It can be accessed at http://www.ncbi.nlm.nih.gov/BLAST/. A description of how to determine sequence identity using this program is available at http://www.ncbi.nlm.nih.gov/BLAST/blast_help.html.

Homologs of the disclosed EDA1-II protein are typically characterized by possession of at least 95%, or at least 98% sequence identity counted over the full length alignment with the disclosed amino acid sequence using the NCBI Basic Blast 2.0, gapped blastp with databases such as the nr or swissprot database. Alternatively, one may manually align the sequences and count the number of identical amino acids. This number divided by the total number of amino acids in your sequence multiplied by 100 results in the percent identity.

Homologs of the disclosed dl and DL proteins are typically characterized by possession of at least 70% sequence identity counted over the full length alignment with the disclosed amino acid sequences using the NCBI Blast 2.0, or using the manual alignment as described above. Proteins with even greater similarity to the dl and DL sequences will show increasing percentage identities when assessed by this method, such as at least 75%, at least 80%, at least 90% or at least 95% or even 98% sequence identity. When less than the entire sequence is being compared for sequence identity, homologs will typically possess at least 75% sequence identity over short windows of 10–20 amino acids, and may possess sequence identities of at least 85% or at least 90% or 95% or even 98% depending on their similarity to the reference sequence. Methods for determining sequence identity over such short windows are described at http://www.ncbi.nlm.nih.gov/BLAST/blast_FAQs.html. One of skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

One indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993), and are discussed in more detail below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that all encode substantially the same protein.

Specific Binding Agent

An agent that binds substantially only to a defined target. Thus an EDA1-II, dl or DL protein specific binding agent binds substantially only the EDA1-II, dl or DL protein, respectively.

The term "anti-EDA1-II protein antibodies" encompasses monoclonal and polyclonal antibodies that are specific for the EDA1-II protein, i.e., which bind substantially only to the EDA1-II protein when assessed using the methods described below, as well as immunologically effective portions ("fragments") thereof. The term "anti-dl or DL protein antibodies" encompasses monoclonal and polyclonal antibodies that are specific for the dl and DL proteins, respectively, i.e., which bind substantially only to the dl or DL protein when assessed using the methods described below, as well as immunologically effective portions ("fragments") thereof. The antibodies used in the present invention may be monoclonal antibodies (or immunologically effective portions thereof) and may also be humanized monoclonal antibodies (or immunologically effective portions thereof). Immunologically effective portions of monoclonal antibodies include Fab, Fab', F(ab')$_2$ Fabc and Fv portions (for a review, see Better and Horowitz, 1989). Antibodies may also be produced using standard procedures described in a number of texts, including Harlow and Lane (1988).

The determination that a particular agent binds substantially only to the EDA1-II, dl or DL protein may readily be made by using or adapting routine procedures. One suitable in vitro assay makes use of the Western blotting procedure (described in many standard texts, including Harlow and Lane, 1988). Western blotting may be used to determine that a given protein binding agent, such as a monoclonal antibody, binds substantially only to the protein.

Subject

Living multicellular vertebrate organisms, a category which includes, both human and veterinary subjects for example, mammals and birds.

Transformed

A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector

A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art.

Allele Specific Oligonucleotide (ASO) Analysis

A method which can be used to determine if a mutation is present in a gene. In this method, probes or primers are designed to hybridize selectively to either the normal or mutant allele. These probes are used, with two other probes, to amplify the sequences across the mutation site, for example using PCR. The amplified DNA is applied to nitrocellulose, for example using slot-blotting. The nitrocellulose filter is then hybridized with the normal or mutant probe. The probe can be radiolabeled or labeled with a chemiluminescent compound.

The resulting autoradiographs are subsequently read to determine if the patient's amplified DNA is normal, deleted, or if both sequences are present. If only the normal sequence is present, then the individual does not have that specific mutation. If only the mutant sequence is detected, the individual is homozygous or hemizygous for the mutation which causes ED. If both sequences are present, the individual is heterozygous for the mutation which causes ED, and is therefore a carrier.

Single-Stranded Conformation Polymorphism (SSCP) Analysis

Another method which can be used to determine if a mutation is present in a gene. In this method, mutations are detected by analyzing the conformational change in the DNA due to the mutation. Briefly, genomic DNA is isolated from an individual and the region containing the mutation is amplified, for example using PCR. The primers used in the PCR reaction can be radiolabeled to label of the DNA fragments, or the DNA can be directly visulaized by silver staining. The resulting fragments are electrophoresed on a polyacrylamide gel. The bands from the normal sample will have a different electrophoretic mobility than the mutant or carrier samples. The samples are analyzed as described above for ASO analysis.

Dideoxy Fingerprinting (ddF)

Another method which can be used to determine if a mutation is present in a gene. This method is a hybrid between dideoxy sequencing and SSCP that can detect the presence of single base and other sequence changes in PCR-amplified segments. ddF involves a Sanger sequencing reaction with one dideoxynucleotide, followed by nondenaturing gel electrophoresis. The approximate locations of the sequence changes could be determined from the ddF pattern. Genomic DNA is amplified as in SSCP with the same primer sets. Analysis can be either manually with radioactive labelling or by fluorescent techniques on an automated sequencer.

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

DETAILED DESCRIPTION OF THE INVENTION

EXAMPLE 1

Cloning and Characterization of Human EDA1 Isoform II

One aspect of the invention is the isolation of an EDA1 cDNA splice-form that is homologous to the murine Ta cDNA and codes for a putative, second isoform of the EDA1 protein (isoform II). The cloning and sequencing of the Ta gene were previously disclosed (Ferguson et al., 1997, Hum. Molec. Genet. 6:1589–1594, hereby incorporated by reference in its entirety). Nearly all of the mutations associated with XLHED are located within the exons identified in this new splice-form. These results provide evidence that EDA1 isoform II is essential for hair, tooth and eccrine sweat gland morphogenesis. In addition, the identification of the additional exons permits direct molecular diagnostic testing for XLHED by mutation analysis.

Also disclosed in the Examples below is the isolation of the murine and human proteins that are believed to function as a receptor for the Ta and EDA1-II proteins, respectively, as well as the DNA sequences encoding the receptors.

EDA1-II Isolation and Analysis

Materials and Methods

Isolation and Analysis of EDA1 cDNAs

A human cDNA library constructed with mRNA isolated from 20–22 week fetal liver tissue was obtained from Clontech, Inc. DNA primers used for PCR amplifications are published (see Table 1 in the erratum Monreal et al., 1998, Am. J. Hum. Genet. 63:1253–55, which corresponds to the publication Monreal et al., 1998, Am. J. Hum. Genet. 63:380–9, both hereby incorporated by reference in their entirety). PCR reactions for cDNA amplifications included 16.6 mM $(NH_4)SO_4$, 67 mM Tris (pH 8.8), 6.7 mM $MgCl_2$, 170 µg/ml BSA, 6.7 µM EDTA and 10 mM BME, 10 ng of cDNA, 12.5 pM of each primer, 25 nM of dNTPs and 0.75 units of AmpliTaq polymerase (Perkin-Elmer, Inc.). Reactions were cycled at: 92° C. for 30 seconds, 58° C. for 30 seconds, and 72° C. for 1 minute, for 32 cycles. PCR products were electrophoresed on agarose gel, purified using GeneClean (Bio101, Inc.) and sequenced using Taq DyeDeoxy Terminators (Applied Biosystems). Sequencing reactions were run on a Model 373A DNA sequencer (Applied Biosystems). Alignments of nucleotide and protein sequences were performed using FASTA (Pearson 1994). Nucleic acid sequence similarity searches were performed using the BLAST program against the non-redundant sequence and EST databases of the National Center for Biotechnology Information (Altschul et al. 1990).

Analysis of EDA1 Gene Structure

With the exception of exons 1–3, PCR amplification between all exons was achieved using 1 unit of $rT^{th}$ DNA Polymerase, XL (Perkin-Elhmer, Inc.) in a reaction mixture with 1× Buffer 2, 1 mM $Mg(OAc)_2$ and 800 µM dNTPs, 30 pM of each primer and 10 ng of the human YAC DNA template, yWXD1341. Intron sizes were estimated by agarose gel electrophoresis of the PCR products. DNA primer sequences are previously described (see Table 1 in the erratum Monreal et al., 1998, Am. J. Hum. Genet. 63:1253–55). The reactions were heated to 94° C. for 1 minute and 60° C. for 5 minutes for a total of 30 cycles followed by a 10 minute incubation at 72° C. Vectorette PCR was used to obtain intron sequence flanking exon 3 (Arnold and Hodgson 1991). PCR products containing the intron/exon boundaries were sequenced as described above. Exons 2, 3 and 9 were physically mapped using human YACs yWXD1851, yWXD 3583 and yWXD1341, obtained from American Type Culture Collection (Manassas, Va.). Amplification of the exons from these YACs was performed using the Taq PCR conditions described above.

Northern Blot Analysis

Human Multi-Tissue Northern blots I and IV (Clontech, Inc.) were hybridized with a $^{32}P$ labeled PCR product that included exon 1 to exon 9 (PCR primers shown in Table 1 of the erratum Monreal et al., 1998, Am. J. Hum. Genet. 63:1253–55). The filters were hybridized and washed according to the manufacturer's recommendations. The signals were visualized using Kodak X-Omat film with an exposure time of 3 days.

Patients Studied

Affected males from 18 unrelated families with presumed X-linked hypohidrotic ectodermal dysplasia were selected for mutation analysis of the EDA1 gene. Their genomic DNAs had been previously extracted and analyzed for mutations within exons 1 and 2 of the EDA1 gene, but none were found (Ferguson et al. 1998). All affected males had the classic phenotype of XLHED including tooth, hair and sweat gland abnormalities. Ten of the families showed vertical transmission of the trait with two or more affected generations. Eight families had a single affected generation, with two affected brothers in three of the families, and a single affected male in five. None of the families was consanguineous or had severely affected females. Where applicable, DNA samples from other family members were studied to determine if the variants detected represented de novo mutations.

Mutation Analysis

Exons were amplified from genomic DNA using primers previously described (see Table 1 in the erratum Monreal et al., 1998, Am. J. Hum. Genet. 63:1253–55) and the reactions conditions described above with AmpliTaq Polymerase. Amplicons were designed to include at least 28 base pairs (bp) of 3' and 5' flanking intronic regions. PCR products were treated with Shrimp Alkaline Phosphatase and Exonuclease I (Amersham, Inc.) to remove primers and excess nucleotides, and DNAs were sequenced using RediVu Thermosequenase Kit (Amersham, Inc.). Sequencing reactions were visualized by electrophoretic separation on an 8% polyacrylamide gel, and subsequent exposure on Kodak X-Omat film for 1–3 days. DNA sequence variants were verified by automated sequencing using an ABI Model 373A sequencer (Applied Biosystems, Inc.). Allele specific oligonucleotide (ASO) analysis was performed to detect polymorphisms in an unaffected population and to identify de novo mutations in a subset of families as described in previous studies (Ferguson et al. 1998, herein incorporated by reference). One exception, the G1136A mutation (see Table 1), was analyzed by restriction digestion of PCR amplified exon 8 DNAs using BanI (New England Biolabs, Inc.). In all cases, genomic DNA samples from 40 control individuals, representing 60 X chromosomes were analyzed. The de novo status of Del 794–829 in families ED1050 and ED1204 was established by PCR amplifying exon 5 sequences, using primers 5' AGAAAGCAGGACCTC-CTGG 3' (Seq. I.D. No. 20) and 5' CTCTCAGGATCAC-CCACTC 3' (Seq. I.D. No. 21), and separating the products on a 3% agarose gel (SeaKem, Inc.).

Results

Identification of a New EDA1 Splice-form

A novel EDA1 cDNA was PCR amplified from a human fetal liver library using primers derived from the sequence of the homologous murine gene, Tabby (GenBank Accession No. AF004435). The 1.5 kb human cDNA included 610 bp of sequence that was identical to the first exon of a previously identified 0.8 kb EDA1 cDNA (Kere et al. 1996), followed by 930 bp of unique DNA sequence. This cDNA included a 1173 bp open reading frame, followed by 160 bp of 3' UTR. No polyadenylation signal sequence was identified. The cDNA is predicted to encode a 391 residue protein, 256 amino acids of which are encoded by new exons. The predicted protein is 94% identical to the Tabby protein (Seq. I.D. No. 4), and includes a collagen-like domain with 19 repeats of a Gly-X-Y motif, interrupted by two amino acids between repeats 11 and 12 (FIG. 1).

Gene Structure

The exon boundaries and flanking sequences of all introns were established using either interexon or vectorette PCR amplification, followed by direct sequencing of the intron/exon junctions (see Table 2 in the erratum Monreal et al., 1998, Am. J. Hum. Genet. 63:1253–55 and GenBank accession NOS. AF060992 and AF060998). In total, 7 new exons were identified in the EDA1 gene (FIG. 2). These new exons (4–9) are within relatively close proximity to one another, with introns ranging in size from 1 kb to 5 kb in length. The intron between exon 1 and exon 3 is estimated to be at least 300 kb, as deduced by the analysis of YACs that were previously mapped to the EDA1 region (YACs yWXD1850, yWXD3583 and yWXD1341 map from centromere to telomere and 5' to 3' of EDA1.) (Srivastava et al. 1996). By both Southern (Ferguson et al. 1997) and PCR analysis, exons 3–9 localize to yWXD1341, but not to yWXD1850 or yWXD3583. The previously identified exon 2 (Kere et al. 1996), not present in this splice-form, is present on all three YAC clones. Taken together, these data suggest that the newly identified exons are 3' and telomeric to exon 2 and map at least 300 kb from exon 1. The exon boundaries of the EDA1 and Tabby genes are completely conserved.

Expression Studies

Northern blot analysis of RNA isolated from several human tissues (brain, heart, placenta, lung, liver, muscle, kidney, pancreas, spleen, thymus, prostate, testis, uterus, small intestine, colon, and leukocytes), hybridized with exons 1–9 of the cDNA, detected a 5–6 kb transcript. No additional hybridization was observed with longer exposures. The most abundant signal was detected in RNA isolated from adult heart, pancreas, prostate and uterus. Weaker signal was seen in RNA isolated from muscle, spleen, thymus, testis and small intestine.

To identify any rare, alternative EDA1 splice products in the fetal liver library, the cDNA was amplified with DNA primers between exon 1 and exons 3, 5, 7 or 9. All PCR products analyzed had identical sequences, with no differences in exon usage. To identify splice products that contain exon 1 but not the novel exons, the library was PCR amplified using primers from either exon 1 or exon 3, directed in the 3' direction, in combination with library vector primers. All of the PCR products generated with the exon 1 primer had corresponding products that were produced with the exon 3 primer, suggesting that all cDNAs with exon 1 sequences also have exon 3 sequences. Similarly, all cDNAs with exon 3 appear to contain exon 1 sequences, since 5' directed primers from exon 1 or exon 3, in combination with vector primers, generated corresponding PCR products.

Finally, since the Tabby cDNA had been isolated in two forms, which varied by the presence or absence of nucleotides 958–1000 (Ferguson et al. 1997; Srivastava et al. 1997), it was determined whether the human cDNA might also have a 42 bp variant. Primers closely flanking the 42 bp region were used to amplify the human cDNA library. Only a single 190 bp cDNA product, which included the 42 bp variable region, was identified. Analysis of the intron/exon boundaries shows that these 42 bp are contiguous with exon 8 in genomic DNA and thus do not represent a separate exon, but rather result from the use of an alternate splice donor site.

Mutations Identified

Mutation analysis was conducted on genomic DNAs isolated from 18 families with XLHED. The families were selected to include some with vertical transmission of the disease and others with sporadic cases. Every exon, including flanking splice recognition sequences, was PCR amplified and sequenced. Sequence variants were confirmed by sequencing the opposing strand of DNA. DNA changes were confirmed in 17 individuals (Table 1). Four individuals were found to have genomic deletions, two of which also produced frameshift mutations. Twelve individuals had a single base pair change that was predicted to generate a missense mutation, and one person had a base pair substitution that created a premature termination codon.

TABLE 1

EDA1 Mutations in XLHED Patients

| Family | Sequence Change | Exon | Predicted Effect[a] |
|---|---|---|---|
| ED1081 | C704T | 3 | R155C |
| ED1095[b] | C707T | 3 | R156C |
| ED1039 | G708A | 3 | R156H |

TABLE 1-continued

EDA1 Mutations in XLHED Patients

| Family | Sequence Change | Exon | Predicted Effect[a] |
|---|---|---|---|
| ED1011 | C867T | 5 | P209L |
| ED1019 | G912C | 5 | G224A |
| ED1050 | Del 794-829 | 5 | Del 185-196 |
| ED1204[b] | Del 794-829 | 5 | Del 185-196 |
| ED1018[b] | Del 803-830 | 5 | Del 188-197, FS 198, Ter 280 |
| ED1097[b] | Del 904-938 | 5 | Del 221-233, FS 234, Ter 240 |
| ED1197 | A996T | 7 | H252L |
| ED1007 | G1136A | 8 | G299S |
| ED1002 | G1136A | 8 | G299S |
| ED1001 | G1202T | 9 | E321Ter |
| ED1021 | G1285A | 9 | A349T |
| ED1126[b] | G1285A | 9 | A349T |
| ED1073 | C1308A | 9 | A356D |
| ED1022 | G1311C | 9 | R357P |

[a]FS = frameshift; Ter = termination.
[b]De novo mutation.

Figure 3:
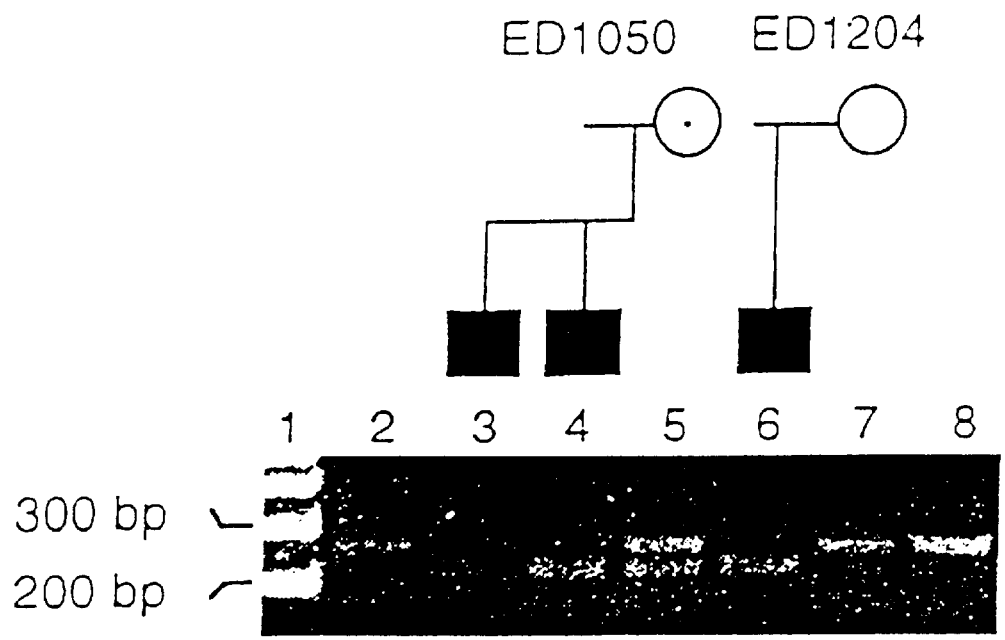
FIG. 3 is a digital image of an agarose-gel analysis of EDA1-II Del794–829. Circles represent females, with a dot indicating XLHED carrier status. Blackened boxes represent affected males. Molecular size markers are shown in lane 1, and control DNAs from unrelated, unaffected males are shown in lanes 2 and 8.

To determine whether any of the putative missense mutations identified were present in an unaffected population, and thus likely to be a non-pathogenic polymorphism, allele specific oligonucleotide (ASO) hybridization was used to survey 60 X chromosomes. None of the variants was found to be present in the control population. Three presumed mutations (Del 794-829, G1136A and G1285A) were each identified twice among the 18 affected individuals. In two of these cases (Del 794-829 and G1285A), a de novo mutation was found in one of the families (ED1204 and ED1126), arguing against inheritance from a common ancestor (FIG. 3). Additional sequence variants were identified within intronic regions. Because these changes did not appear to affect the splice recognition sites and were also present in unaffected individuals, they were classified as non-pathogenic polymorphisms.

Novel EDA1 Splice-form

The novel EDA1 cDNA containing a complete open reading frame (Seq. I.D. No. 14) encodes a novel isoform of the EDA1 protein (isoform II). Isoform II is highly homologous to the Tabby protein (Seq. I.D. No. 4). The full length transcript is likely to include a longer 3' UTR, because no polyadenylation signal sequence was identified, and Northern analysis indicates the transcript to be 5–6 kb in length. The Tabby transcript is also 5–6 kb in length (Ferguson et al. 1997) and has a 3'UTR of approximately 3.5 kb (Srivastava et al. 1997).

It is anticipated that this novel cDNA represents the major EDA1 transcript, since only a single hybridization band was detected by Northern blot analysis. The transcript is expressed in a variety of organs, which are not clinically associated with HED, indicating that the EDA1-II protein may serve a redundant finction in some tissues. No other EDA1 splice products were identified, including the original 0.8 kb full-length transcript encoding EDA1 isoform I. The possibility that other splice forms exist in other tissues can not be excluded.

In the mouse, only the 5 kb homologous cDNA, and variants thereof, have been identified. One variant appears to result from the use of a cryptic splice donor site at the 3' end of exon 7 (Ferguson et al. 1997), while two others include portions of intron 1 or intron 2 and are missing all downstream exons (Srivastava et al. 1997). The fact that 95% of XLHED mutations were detected within the newly identified exons indicates that isoform II is of importance in the biological activity of the protein, and supports the notion that there are likely no additional exons in the EDA1 gene that are critical for normal development.

Predicted Protein Structure

The EDA/Ta proteins (FIG. 1) can be divided into 5 domains as listed from N-terminus to C-terminus: a cytoplasmic domain (residues 1–41), transmembrane domain (42–60), extracellular domain with furin cleavage site (61–179, with potential furin cleavage site at residues 153–156-RVRR), collagen-like domain (180–238) and TNF domain (239–391).

The predicted EDA1 isoform II protein includes a single transmembrane domain and, like EDA1 isoform I, is believed to be a cell surface protein with a type II orientation (the C-terminus projecting extracellularly) (Ezer et al. 1997). A predicted collagen domain $(Gly-X-Y)_{19}$ may form a triple helix with either itself or the collagen domain of other proteins, resulting in the formation of either homo-trimeric or hetero-trimeric complexes. Three cysteine residues present in the C-terminal domains of both the mouse and human proteins may serve to stabilize such trimeric complexes. It is anticipated that the EDA1-II protein plays a role in intercellular signaling, either as a membrane-bound or soluble ligand. In addition, it may serve a function in cell adhesion or cell migration through interactions with the extracellular matrix. Other membrane associated proteins with collagen domains include collagen XIII and XVII, macrophage scavenger receptor, and a bacteria binding macrophage receptor (MARCO) (Acton et al. 1993; Gatalica et al. 1997; Peltonen et al. 1997; Rohrer et al. 1990).

An overall high degree of sequence conservation (94% identity) was found between the predicted EDA1-isoform II and Tabby proteins. This conservation is particularly striking in the C-terminal 211 amino acids, which begin with the Gly-X-Y domain, and in which only a single, conservative substitution at position 241 is present. The extreme conservation in the C-terminus suggests that it is of biological importance in protein function and that it may interact with other proteins that are also highly conserved. There is less conservation between residues 1–180, particularly 1–163, and at residues 11, 28, 41, 74, 81, 83, 93, 95, 99, 100, 104, 111, 112, 121, 122, 124, 125, 126, 130, 145 and 163. Hence the region from residues 74–126, and particularly 81–126, 93–126 and 93–112 are particularly novel in comparison to Tabby.

It is anticipated that the minimal domain with possible functional activity would be the TNF-like domain (239–391), the domain likely to bind to and activate the receptor protein (see Examples 2 and 3). A more conservative choice of functional peptide would begin at the furin recognition sequence and continue through the C-terminus (153–391), which is believed to be the native, secreted form of the protein. Sequence variations of the potential furin cleavage site (RVRR, 153–156) appear to cause a loss of protein flnction, supporting the notion that secretion of the protein is essential, at least for biological activity of the protein as it is produced by the body (but which may not be true for exogenous forms of the protein, for example, that are produced by recombinant methods and applied exogenously, for example topically).

The structural conservation of the collagen-like domain (180–238) appears important, because changes that alter the Gly-Xxx-Yyy repeated sequence appear to lose function, as do changes that shorten the domain by 12 amino acids. Sequence conservation between the mouse and human sequences highlight the importance of the TNF domain. Changes that are likely to disrupt the folding of the protein, in particular by changes in the proposed central beta-sheet (291–309), are likely to cause loss of function. FIG. 4 illustrates the sequence of the central β-sheet in several members of the TNF family. A comparison of these sequences provides information about possible substitutions that can be made in the EDA1-II sequence without changing the structure of the central β-sheet. The amino acids that are conserved across the TNF family (indicated by dots above the column) are likely more critical in the structure and function of the molecule, and would not be the first candidates for mutation when it is desired to preserve biological activity.

The aligned sequences of EDA1-II and the other members of the TNF family, however, illustrate that the second amino acid residue (E) may possibly be substituted with V, L, A or T (as in the aligned positions within the central β-sheet of the other members of the TNF family), while still retaining biological activity. Substitutions for other residues of the central β sheet could also be proposed based on the variation of the residues in the aligned positions of the other members of the TNF family.

Once mutations in the EDA1-II sequence have been made, convenient assays are available to determine whether the mutant peptide has retained the EDA1-II biological activity. The biological activity of the proposed secreted peptide (153–391) could be assessed by the intradermal injection or topical application of the protein to the skin or tails of newborn tabby mice. Functional protein activity would be detected by the induction of hair growth. Alternatively, the produced protein could be applied to or injected into the footpads of newborn tabby mice, with subsequent monitoring of sweat gland development. Another functional assay would be to apply or express the truncated protein in an in vitro tooth organ culture system, and then to determine whether developmental changes occur (which would not be expected in the absence of a functional variant of the protein). Any of these assays could be modified by using in vivo expression of the EDA1-II gene, and variants thereof, instead of applying/injecting purified proteins.

Antagonists of EDA1-II protein function (for example in the treatment of hirsutism or breast cancer) could be generated by producing antibodies that bind to the TNF-like domain. Additionally, the EDA1-II protein could be modified to generate homodimers that bind to its receptor (DL, or its murine homolog dl) without activating them. Multimerization (e.g. trimerization) of the receptor, via multimerization (e.g. trimerization) of the ligand, it thought to activate the downstream pathway.

Functional Implications of Identified Mutations

Some identified EDA1-II mutations are shown in Table 1. Mutations were identified within exons 3–9 of EDA1-II in 94.4% of the families studied (17/18). Coupled with the previous mutation analysis of exon 1, which found mutations in approximately 7–8% of XLHED families (Ferguson et al. 1998), it is estimated that 95% of mutations in XLHED patients are located within the 1173 bp coding region of this splice form. Additional mutations may be located in the remaining 3' UTR sequence, in regulatory elements, in unsequenced intronic regions, or may include large genomic rearrangements that would have been undetectable with the techniques used in these examples.

Although the identified mutations are heterogeneous, more than half of the individuals (11/18) were found to have changes within the coding regions of exons 5 and 9. These two exons account for about 40% of the ORF. Six mutations were detected in exon 5, including 4 deletions 28 bp to 36 bp long. Exon 5 encodes the Gly-X-Y domain, and deletions within it may be enriched because of the high frequency of repeated sequences. Indeed, one deletion identified in two unrelated families (Del 794–829), is flanked by a 17 bp repeated sequence containing just 2 nucleotide differences. This deletion is predicted to truncate the collagen domain of the protein, but otherwise leaves the protein intact. If the resulting mutant protein is stable, it would point to the collagen domain being required for normal protein function.

Two missense mutations may also perturb the collagen domain. In one case, the glycine of a Gly-X-Y triplet is substituted by an alanine. In another variant, a 3rd position proline (Gly-X-Pro) is substituted by a leucine. The 3rd position proline plays an important role in stabilizing the collagen helix (Brodsky and Shah 1995). The coding region of exon 9 also contains a disproportionate share of mutations (all missense). Three changes cluster within an 8 amino acid region, highlighting the importance of this domain for either protein stability or function. Also of note, this region overlaps with the C-terminal cysteine domain, which may stabilize intermolecular associations.

Finally, a mutation identified twice in exon 8, G1136A, is located within the 42 bp region previously found to be deleted in one of the Tabby splice-forms (Ferguson et al. 1997). This indicates that the 14 amino acid region encoded by the sequence is important in at least some, if not all, tissues.

Diagnostic Applications

Linkage-based molecular diagnostic testing for XLHED has been available for approximately 10 years and can significantly improve carrier risk estimates (Zonana et al. 1988; Zonana et al. 1992; Zonana et al. 1989). However, linkage analysis is limited to families with two or more affected individuals, and multiple family members must be available and cooperative. However, using the gene sequence information of the present invention, and direct mutation screening, approximately 95% of mutations can be detected in individuals with presumed XLHED.

The finding that approximately half of all identifiable mutations are within exon 5 and the coding region of exon 9 indicates that initial analysis of these two exons would provide the most efficient approach in a mutation detection protocol. Since these two coding regions are relatively small (181 bp and 252 bp), they are amenable to direct sequencing, screening by SSCP (Sheffield et al. 1993), dideoxyfmgerprinting (ddF) (Liu et al. 1996), or by other mutation detection methods (Grompe 1993). Amplification of exon 5 may reveal deletions large enough to be detectable by agarose gel analysis, as seen in four families in FIG. 3. If no mutations are present in exons 5 and 9, screening or sequencing exons 1, 3, 7 and 8 can be done and may yield an additional 40% of mutations. No mutations were detected in exons 4 and 6; however, they represent only about 5% of the coding sequence, and analysis of a larger set of patients may reveal mutations in these exons as well. In families where mutations are not detected, linkage analysis can still be used when the family is informative.

Primers have been designed that can be used for diagnosis of XLHED. These include primers for amplification and sequencing of the intron regions of exon 3, 5, and 9. These primers are as follows: Exon 3: 5' tatgttggctatgactgactgagtgg 3' (Seq. I.D. No. 22) and 5' ccctaccaagaaggtagttc 3' (Seq. I.D. No. 23); Exon 5: 5' aaaaagtaacactgatcctattt 3' (Seq. I.D. No. 117) or 5' agaaagcaggacctcctgg 3' (Seq. I.D. No. 118) as a forward primer with 5' ctctcaggatcacccactcctg 3' (Seq. I.D. No. 24) as the reverse primer; Exon 9: 5' tgtcaattcaccacagggag 3' (Seq. I.D. No. 25) and 5' gaatctaggatgcaggggc 3' (Seq. I.D. No. 26). There are also primers which can be used to directly distinguish common mutations in Exon 3: normal sequence 5' tattgcggcgaacacg 3' (Seq. I.D. No. 27); altered sequence 5' tattgcagcgaacacg 3' (Seq. I.D. No. 28); and altered sequence 5' tattgcggcaaaacacg 3' (Seq. I.D. No. 29).

Five families had a negative family history and an unaffected mother, and thus were potentially informative as to whether the mutation was de novo. In all 5 families the mutations (3 deletions and 2 missense) were found to be de novo, thus arising either during oogenesis or postzygotically. There appears to be an equal rate of mutation during oogenesis and spermatogenesis. The autosomal recessive form of the disorder is infrequent compared to the X-linked form. Review of clinical features showed no obvious phenotype/genotype correlation between individuals with missense mutations, and those with deletions truncating the collagen domain, nor those with frameshift mutations that may yield either an abnormal truncated protein or no protein at all. This is similar to the previous analysis of mutations within exon 1, which showed no difference in phenotype between patients with missense mutations and those with exon deletions or frameshifts (Ferguson et al. 1998; Kere et al. 1996).

The availability of direct testing for XLHED mutations is a significant advance in diagnostic capabilities. It allows carrier detection in families with only a single affected male, and helps differentiate the X-linked disorder from the rarer, autosomal recessive form of the disorder. It is also helpful in distinguishing sporadic carriers of XLHED from females with an autosomal dominant form of isolated hypodontia (Arte et al. 1996). Finally, testing should also be useful in the diagnosis of XLHED in affected male infants, especially in sporadic cases, before abnormal tooth and hair involvement is apparent. Early diagnosis can avert the significant morbidity and mortality associated with the disorder due to uncontrolled hyperthermia (Clarke et al. 1987).

Therapeutic Applications

To promote hair growth, a full length EDA1-II protein would be produced, or a truncated version for example residues 133–391, 153–391 or 239–391, or variants thereof that retain the hair growth promoting activity of EDA1-II. The purified protein, applied at concentrations ranging from 1 ng/ml to 1 g/ml, would be administered to the tails and bellies of newborn tabby mice, wildtype mice and nude mice over a period of 6 weeks. Various methods available for the appropriate delivery of the protein to hair follicles in human skin could be attempted, as described by Hoffman, 1998; Lieb et al., 1997; Laurer et al., 1995; Illel, 1997. An example is topical daily application to a bald area of the human scalp. Alternatively, gene therapy methods to express the EDA1-II gene or portions thereof, could be investigated using the techniques of Hoffman, 1998 or Li and Hoffman, 1995. Hair growth would be monitored following therapies.

Using these same assays, the EDA1-II protein or EDA1-II gene may also be useful for the development of an antagonist of the dl or DL receptor (see Examples 2 and 3), to reduce hair growth. Such an antagonist could be a non-functional form of the EDA1-II ligand.

The full-length or truncated forms (as noted above) of the EDA1-II protein may also be used as a stimulant for tooth growth, in cases either of tooth loss or of natural absence of teeth. EDA1-II protein may be used to stimulate tooth growth in humans directly, or alternatively in tissue culture (artificial) conditions, with subsequent introduction of teeth into humans or other organisms.

In addition, the EDA1-II protein or EDA1-II gene may also be useful for the stimulation of eccrine sweat gland development, for example in individuals for whom the normal sweating mechanism is compromised by disease, trauma, burns or surgery.

EXAMPLE 2

Cloning and Analysis of Murine dl

Downless mutant mice fail to induce development of epidermal derivatives such as hair follicles and sweat glands. The murine downless gene (dl, Seq. ID. No. 12) encodes a novel tumor necrosis factor receptor homologue, which is mutated in known families of spontaneous mutants which have previously been known as downless mice. As shown in the following examples, the dl gene, and its human homolog DL, are receptors that are upregulated in cells committed to a hair follicle fate. Downless mutant mice do not show upregulation of transcript levels, indicating that this process requires a functional receptor. The ligand for the receptor is thought to be the product of the Tabby gene in mice, and the EDA1-II gene in humans, which encode proteins similar to the TNF ligand family. The Tabby mutant phenotype is identical to that of the downless mutant mice. This receptor provides a therapeutic target that may be used in standard screening assays to identify drug agonists and antagonists with potential applications, including stimulation of hair growth in adult skin (treatment of baldness), stimulation of skin (particularly epidermal) healing, inhibition of hair growth in adult skin (treatment of hirsutism), treatment of ectodermal dysplasias, as well as treatment of tooth disorders and disorders of glands such as sweat and sebaceous glands.

Materials and Methods

BAC Library Screening and DNA Preparation

Two sets of oligonucleotides were designed based on known YAC D9 sequence. The sequences of these oligo sets were: Oligo 27209 ATCATGGCTGTGCACTCTAG (Seq. I.D. No. 30) and Oligo 27210 ACCTACTGCATGTCT-GTGGA (Seq. I.D. No. 31); Oligo 27213 CACATGCT-CAGTGTTGTCCA (Seq. I.D. No. 32) and Oligo 27214 ACACAGGCTCAGTCATGCGG (Seq. I.D. No. 33).

Both primer pairs were used for primary screening of pooled BAC clones by PCR (Human and Molecular Genetics Department, Baylor College of Medicine). Positive clones were ultimately identified by filter hybridization to [$\alpha$-$^{32}$P]-dCTP labeled PCR product of the oligos used in the primary screen. BACs were grown in a chloramphenicol containing medium and BAC DNA was isolated using QIAGEN plasmid DNA purification columns. The elution buffer was heated to 65° C. and multiple elutions performed. DNA was precipitated using isopropanol, washed with 70% ethanol, and dissolved in 10 mM Tris buffer (pH 8).

cDNA Selection

The cDNA selection protocol used was a modification of that described by Segre et al. (1995). DNA was purified using QIAGEN PCR purification columns after each of the enzymatic steps listed below. BAC 508K21 was digested using Alu I, Hae III, and Rsa I restriction enzymes in separate reactions. The pre-annealed oligonucleotide linkers: 5'biotin-GCGGTGACCCGGGAGATCTGAATTC 3' (Seq. I.D. No. 34) and 5'phosphate-GAATTCAGATC 3' (Seq. I.D. No. 35), were ligated onto the BAC digestion fragments at approximately 50 fold molar excess to generate PCR amplifiable DNA fragments with inverted repeats at their termini. The biotinylated oligonucleotide, Seq. I.D. No. 34, was used to prime the PCR amplification of the DNA pool. The thermal cycling conditions used were: 65° C. for 5 minutes (1 cycle); 94° C. for 45 seconds, 72° C. for 2.5 minutes (20 cycles).

The resulting biotinylated PCR product DNA was used as driver in the hybridizations. To prepare the cDNA tester for hybridization polyA$^+$RNA was isolated from a pool of E13, 17, and P0 skin. Double stranded cDNA was synthesized (cDNA synthesis kit, Gibco) and digested with Alu I, Hae III, and Rsa I. Non-biotinylated linkers of different sequence to those ligated to the driver population were added to the fragments: CTGAGCGGAATTCGTGAGACC (Seq. I.D. No. 36) and phosphate-GGTCTCACGAATTCCGCTCAGTT (Seq. I.D. No. 37). The cDNA pool was amplified by PCR (using cDNA-1) under the same cycle conditions as described for the BAC DNA amplification. Prior to selection 1 µg driver DNA was denatured by boiling and blocked by overnight prehybridization to 2 µg Cot1 DNA plus 8 µg shorn OVE 1B/1B genomic DNA in the following buffer conditions: 0.75 M NaCl, 20 mM sodium phosphate pH 7.2, 5 mM EDTA, 5× Denhardt's solution and 0.1% SDS at 65° C. For the first round of enrichment 1 µg amplified BAC DNA was denatured by boiling, added to the prehybridized cDNA, and allowed hybridize at 65° C. for 3 days in a total volume of 20 µl. Biotinylated driver and annealed cDNAs were immobilized on streptavidin coated magnetic beads (Dynal) and unannealed cDNA was removed by washing with 0.1× SSC, 0.1% SDS at 65° C. After washing, the annealed, selected cDNAs were eluted from the biotinylated driver using 50 mM NaOH, neutralized with 1M Tris pH7.5, and PCR amplified using Seq. I.D. No. 36 under the following cycle conditions: 94° C. for 45 seconds, 64° C. for 45 seconds, 72° C. for 1.25 minutes (30 cycles).

This amplified, selected cDNA was subjected to a second round of enrichment by driver hybridization, washing, and amplification as above. The amplified cDNA from this second enrichment was ligated into pT-Adv (Clontech) and transformed into $E.\ coli$. Bacteria were grown on gridded plates prior to further analysis. One of the clones, cDS 446, was used for further analyses.

cDNA Library Construction and Screening

Poly A$^+$RNA was isolated from E17.5 fetal skin of OVE 951 mice and used as template to prepare the cDNA library. Using the lambda ZAP-cDNA synthesis kit (Stratagene) the library was plated and screened using [α-$^{32}$P]-dCTP labeled cDS446, following kit manufacturer's instructions.

RT-PCR and RACE cDNA was prepared from newborn skin RNA using the SuperScript II kit according to manufacturer's instructions (Gibco BRL). The oligos used to amplify the downless$^{Jackson}$ mutated region from mutant cDNA were: Oligo 28756 AGTGAGAATGATGCCTCC (Seq. I.D. No. 38) and Oligo 28762 GCCTTTGTTCAGTCATAGG (Seq. I.D. No. 39). The thermal cycling conditions used were: 94° C. for 2 minutes (1 cycle); 94° C. for 30 seconds, 58° C. for 45 seconds, 72° C. for 1.5 minutes (34 cycles); and 72° C. for 15 minutes (1 cycle). Seq. I.D. No. 38 was used to directly sequence the RT-PCR product.

Rapid amplification of cDNA ends (RACE) was performed by synthesizing YAC D9 cured E17.5 skin cDNA using random primers (SuperScript II kit, Gibco BRL), and then 3' dC tailing the first strand cDNA using terminal transferase (Gibco BRL). PCR amplification was performed using the following oligonucleotides: Oligo 10S CCT-GAGAGCTCTTTGTGAG (Seq. I.D. No. 40) and Anchored oligo dG CGGGATCCTC-GAGGGGGGGGGGGGGGGH (Seq. I.D. No. 41). The thermal cycling conditions used were: 94° C. for 2 minutes (1 cycle); 94° C. for 30 seconds, 58° C. for 45 seconds, 72° C. for 2 minutes (40 cycles); 72° C. 10 minutes (1 cycle). The PCR product was sequenced using antisense Oligo 28753 AAGCAGAGCTCCACAATC (Seq. I.D. No. 42).

Dl$^{Sleek}$ cDNA was prepared for 3' RACE by generating first strand cDNA using oligodTVN: GGCCGCTCTGGA-CAGGATATGTTTTTTTTTTTTTTTTVN (Seq. I.D. No. 43) primer (SuperScript II kit, Gibco). PCR was performed on the first strand reaction product using the oligos: 5' GGAACAGTCAAGAGCGAGTT (Seq. I.D. No. 44) and Oligo dT nested GCGGATCCAGGCCGCTCTGGACAG-GATATG (Seq. I.D. No. 45) under the following conditions: 94° C. for 2 minutes (1 cycle); 94° C. for 30 seconds, 58° C. for 45 seconds, 72° C. for 1.75 minutes (36 cycles); 72° C. 15 minutes (1 cycle). The PCR product was directly sequenced using Seq. I.D. No. 38.

All DNA sequencing was performed using the standard automated method at either the Human and Molecular Genetics sequencing core laboratory, or the Cell Biology sequencing core laboratory. All PCR products were purified prior to sequencing using the QIAGEN PCR purification or QIAEX II gel purification kits according to manufacturer's instructions.

Using similar techniques, allelic variations of the dl DNA, which encodes the dl receptor that is absent in downless mice, could also be detected in humans, mice, or other species of mammals. The invention therefore includes DNA sequences that include allelic variations in the sequence.

Nucleic Acid Preparation and Hybridizations

For Northern analysis RNA was prepared from E17.5 skin of the various genotypes using the phenol/guanidium thiocyanate method (RNA STAT 60, Tel-Test). 300 µg of each total RNA sample was polyA enriched (Messagemaker Kit, Gibco BRL) and precipitated with ethanol. All of the recovered RNA was separated on a formaldehyde containing agarose gel, transferred to a nylon membrane (Zeta Probe, Bio-Rad), and probed with [α-$^{32}$P]-dCTP labeled dl 5' untranslated region and open reading frame in 0.5M sodium phosphate, 7% SDS at 65° C. overnight. Four post-hybridization washes were performed in 0.1× SSC, 0.1% SDS at 65° C. for 20 minutes each.

Genomic DNA for Southern analysis was isolated from proteaseK digested mouse tails, followed by phenol extraction and thanol precipitation. The isolated DNA was EcoRi digested, separated on a 1% agarose gel, and transferred to nylon membrane (Zeta Probe, Bio-Rad). Hybridization to the entire [α-$^{32}$P]-dCTP labeled dl cDNA and subsequent washing was performed under the conditions described above for Northern blotting.

In situ Hybridization

Tissue was fixed in 10% formalin for two days, then stored in 70% ethanol. Paraffin sections of mouse embryos were deparaffinized in xylene, rehydrated, treated with 20 mg/ml protease K, and refixed in 4% paraformaldehyde before prehybridization. Hybridization was carried out overnight at 50° C. Slides were washed in FSM (50% formalin, 2× SSC, 1 mM EDTA, 2-mercaptoethanol) for 1 hour, treated with 20 µg/ml RNAse A for 30 minutes, and washed in FSM for 2 hours before coating with silver emulsion (Kodak) and exposing for 2–4 weeks. The entire dl cDNA sequence was used to prepare [$^{35}$S]-UTP labeled antisense riboprobe using T7 RNA polymerase. Samples of dl$^{OVE1B}$ tissue were used as negative controls.

Whole mount in situ hybridization was performed using digoxigenin labeled riboprobe transcribed from a genomic DNA clone corresponding to the cDNA selected clone cDS446. The riboprobe was synthesized using the DIG RNA labeling kit (Boehringer Mannheim) according to manufacturer's instructions. Embryos were fixed in 4% paraformaldehyde, bleached, and stored in methanol. For hybridization the samples were rehydrated, treated with proteaseK, and hybridized at 65° C. overnight. Embryos were then washed in 5+ SSC, 1% SDS, 50% formamide at 65° C. for 30 minutes, treated with 100 μg/ml RNase A for 30 minutes, and washed in 2× SSC, 0.1% Tween 20, 50% formamide for 30 minutes. Hybridized riboprobe was detected using the DIG Nucleic Acid Detection kit (Boehringer Mannheim) according to manufacturer's instructions.

Results

Two original families of mouse mutants, called downless-$^{Jackson}$ (recessive inheritance) and Downlesss$^{Sleek}$ (dominant inheritance) due to their poor hair growth, arose spontaneously during the 1960's and 1970's (Soafer, 1973; Crocker and Cattanach 1979). The routine process of introduction of foreign DNA (transgene) into a fertilized embryo resulted in deletion of the gene responsible for the downless phenotype by the transgene. The family of mice carrying this deletion are called OVE 1B, and they have the full range of anhidrotic ectodermal dysplasia symptoms (Shawlott et al., 1989). The presence of the transgene in the OVE 1B mice allowed mapping of the gene region responsible for the mutation, followed by identification of some large fragments of mouse DNA (YACs) that are deleted in the OVE 1B family. Each of the three YACs identified were introduced back into the downless mutant mice to see if any contained a normal version of the mutated gene. One of them, YAC D9 (Majumder et al. 1998, incorporated by reference), was found to completely cure the mutants; the other two did not. The sequence from YAC D9 was used to identify similar large fragments of mouse DNA, called BACs, that overlap YAC D9 and might therefore contain the gene. The BAC that was most similar to YAC D9 was used to identify specific cDNAs from developing skin, each of these being a candidate for the gene.

One of the cDNA fragments identified in this way was found to be deleted in the OVE 1B mutants, and to be expressed by the cells at the base of the hair follicle which surrounds the dermal papilla, which is believed to be the follicle's growth regulation center. The region of the follicle in which it is expressed is called the hair matrix, that is the part of the mature follicle that contains proliferating cells. The lack of hair follicle development and the slow rate of hair growth in both mouse mutants and human ED patients indicates a role for this receptor in promoting hair follicle development and hair growth throughout life. The ability to block or enhance the activity of this receptor should, therefore, allow control over these processes, and be of major clinical and cosmetic relevance. Knowledge of the dl cDNA, and its human homolog DL (see Example 3) and protein sequences, as given in this disclosure, allows screening for, or design of, molecules that modulate DL or dl receptor activity by enhancing or inhibiting its function.

Analysis of the dl Gene

The ORF of the cDNA sequence of the dl gene in mice is shown in Seq. I.D. No. 13, and the corresponding amino acid sequence is shown in Seq. I.D. No. 19. The dl cDNA of Seq. I.D. No. 12 is 3720 nucleotides in length, encodes a protein (Seq. I.D. No. 19) that is 448 amino acids in length, and is maintained in the pBK-CMV plasmid.

Expression Patterns and Deletions in Murine dl

The murine downless gene (dl) is completely deleted in OVE 1B mice, at least partially present in YAC D9, is expressed in developing skin and adult hair follicles, as determined by in situ hybridization, and is mutated in both downless$^{Jackson}$ and Downless$^{Sleek}$ mice, confirming that it is the gene responsible for these phenotypes. The expression pattern of the gene is consistent with it specifying which cells are to become hair follicles, and in adult skin it is expressed by the cells at the very base of the hair follicle which surround the dermal papillae (growth regulation center). The lack of hair follicle development and the slow rate of hair growth in both mouse mutants and human ED patients indicates a role for this receptor in promoting hair follicle development and hair growth throughout life. The ability to block or enhance the activity of this receptor should, therefore, allow control over these processes. Knowledge of the dl cDNA and protein sequence, as given in this disclosure, allows screening for and designing molecules that modulate dl receptor activity by enhancing or inhibiting its function.

The dl mRNA in fetal mouse sldn was detected by Northern blotting. The dl gene is active in normal (wild type) and YAC D9 cured mutants at this stage, and the receptor is made by the downless$^{Jackson}$ mice. The Downlesss$^{Sleek}$ mice have an altered form of the transcript that is smaller than the wild type version, while the OVE 1B mice do not have the transcript.

Analysis of the dl gene in the genome by Southern hybridization demonstrated that the dl gene is absent from the OVE 1B genome and altered in Downless$^{Sleek}$ mice. The YAC D9 cured mutants received many copies of the gene. The murine dl mutation in downless$^{Jackson}$ mice is due to a single nucleotide difference between the wild type and mutant cDNAs at nucleotide 1135 (Seq. I.D. No. 13). This mutation results in glutamate 379 (Seq. I.D. No. 19) of the wild type protein being changed to lysine in the mutant. The position of the dl mutation in downlesss$^{Sleek}$ mice is more severe. Up to nucleotide 964 (Seq. I.D. No. 13) the wild type and mutant sequences are the same. After this nucleotide, the Downless$^{Sleek}$ mRNA is completely different from the wild type cDNA.

dl Expression Analysis

In situ hybridization was used to identify the locations of dl expression in the skin. At embryonic day 15, the dl transcript is detected in the basal layer of the epidermis of a fetal mouse, and at elevated levels in the developing hair follicle buds in sectioned skin.

Analysis of dl expression over the whole mouse fetus at embryonic day 15 demonstrated that dl is made in the developing hair follicles at a high level, and at a lower level in the rest of the skin. The expression of dl was also observed in other tissues such as the lung and kidney. Expression of dl in the growing hair follicles of an adult mouse was also examined. The transcript is present in the cells at the base follicle that surround the dermal papillae (growth signaling center). Some expression is also detected in the sebaceous glands. Expression analysis can also be performed in other species, using the same techniques, to confirm a similar distribution of expression in those species.

EXAMPLE 3

Cloning and Analysis of Human DL

This example describes assays used to clone, sequence and analyze human DL, the murine dl homolog.

Materials and Methods cDNA Cloning and Sequencing of DL

RNA isolated from human fetal skin of 11 week estimated gestational age (EGA) was reverse transcribed (RT) using 25U of MMuLV reverse transcriptase (New England Biolabs) and random hexamer primers (Pharmacia) to provide first strand cDNA used for both 3' RACE experiments, and inter-exon amplification. To obtain the initial human homologous sequence, total human genomic DNA was amplified and sequenced using primers designed from mouse dl cDNA sequence: 5'-TGGTGTCTCTGATGTGC-3' (Seq. I.D. No. 46), and 5'-ACAGTGGCCCGGAAGAAG-3'(Seq. I.D. No. 47). Primers derived from human sequence and primers from additional mouse cDNA sequences, each in a hemi-nested PCR reaction (5'-CTGCGGTGAGAACGAGTAC-3' (Seq. I.D. No. 48), 5'-GGCAAGGTGGCGCCATGT-3' (Seq. I.D. No. 49), then 5'-GGCACCAAAGACGAGGACTA- 3' (Seq. I.D. No. 50), 5'-GGCAAGGTGGCGCCATGT-3' (Seq. I.D. No. 49)), were used to amplify exons 3–12 from human cDNA.

The 5' end of the gene was determined by 5'RACE. An RT reaction on total RNA from human fetal (11 wk EGA) skin was carried out using a human gene specific primer: 5'-TCAGCGTCATTCTCCATGTC-3' (Seq. I.D. No. 51). The product was dA-tailed using terminal transferase (Gibco) and the cDNA was amplified, first using primers 5'-CTAGACTCGAGAATTCGCGGCCGCACTAGT$_{(17)}$ 3' (Seq. I.D. No. 52) and 5'-TCTGGTAGCCTCCTTTGGAA-3' (Seq. I.D. No. 53). The resulting product was then amplified twice, first with primers 5'-CTAGACTCGAGAATTCG-3' (Seq. I.D. No. 54) and 5'-TAGTCCTCGTCTTTGGTGCC-3' (Seq. I.D. No. 55), and subsequently with primers 5'-GAGAATTCGCGGCCGCAC-3' (Seq. 1.D. No. 56) and 5'-AGCCCCGTAGTCTGGTTGTA-3' (Seq. I.D. No. 57). For cycle sequencing, all PCR products were recovered from a 2% agarose gel, purified using GeneClean (Bio101), and sequenced on a Perkin Elmer ABI 373 stretch sequencer using the BigDyeTM terminator kit. In addition, a human fetal heart cDNA library of 20–25 weeks gestation (Clontech, Inc.), containing 2–4×10$^5$ plaques, was screened using a radioactively labeled murine dl cDNA probe.

DNA primers that were used to amplify the various exons of human DL are shown in Table 2.

TABLE 2

DNA Primers Used for cDNA Amplification of human DL

| Exon | Forward Primer | Reverse Primer |
|---|---|---|
| 1–3 | GAGAATTCGCGGCCGCAC (56) | AGCCCCGTAGTCTGGTTGTA (57) |
| 3–4 | CTGCGGTGAGAACGAGTAC (48) | TCTGGTAGCCTCCTTTGGAA (53) |
| 4–12 | CTGCGGTGAGAACGAGTAC (48) | GGCAAGGTGGCGCCATGT* (49) |
| | GGCACCAAAGACGAGGACTA (50) | GGCAAGGTGGCGCCATGT* (49) |

All primers shown in the 5'–3' orientation. Seq. I.D. NOS. shown in parenthesis.
*mouse downless sequence Expression Analysis A Northern blot (Clontech, Inc.) containing RNA from selected human fetal tissues (1 7–24 week EGA) was hybridized with a radiolabeled probe containing exons 5–11.

Nested primers from DL exons 11 and 12 (394 bp amplicon) were used to amplify by PCR a human craniofacial library made from embryos of 42 to 53 day gestation (5'-GCGTCGACAGTGATGAGGA-3' (Seq. I.D. No. 58), 5'-CAGTCTTTTGGCACCACTCA-3' (Seq. I.D. No. 59), then 5'-ACGTGTGTGGAGTCGTGGA-3' (Seq. I.D. No. 60), 5'-CTCGTTGGATCCTTGGCTT-3' (Seq. I.D. No. 61)).

RNA isolated from human fibroblast, keratinocyte (Clonetics) and lymphoblast cell lines, as well as from fetal skin (15 week EGA), was reverse transcribed and subsequently amplified in nested PCR reactions with primers from exons 4 and 6, yielding a 238 bp PCR product (5'-GGCACCAAAGACGAGGACTA-3' (Seq. I.D. No. 50), 5'-TACATGCTGGAGAACAGACC-3' (Seq. I.D. No. 62) and 5'-TTCCAAAGGAGGCTACCAGA-3' (Seq. I.D. No. 63), 5'-TTGGCAGAAGCTCCTGAAGT-3'(Seq. I.D. No. 64)). Control PCR reactions were conducted using primers derived from HPRT cDNA sequence (5'-TGCTCGAGATGTGATGAAGG-3' (Seq. I.D. No. 65), 5'-AAGCAGATGGCCACAGAACT-3' (Seq. I.D. No. 66)).

Physical Mapping and Isolation of Genomic Clones

The Genebridge hybrid panel (Research Genetics) was used for radiation hybrid (RH) mapping, screening with an STS designed from IVS-3 sequence (primers: 5'-CTGCGGTGAGAACGAGTAC-3' (Seq. I.D. No. 48); 5'-TCTGGTAGCCTCCTTTGGAA-3' (Seq. I.D. No. 53)). The results of the screening were analyzed on the Whitehead/MIT Genome Center web site (http://www.genome.wi.mit.edu/cgi-bin/contig/rhmapper.pl). DNAs isolated from YACs (Research Genetics) previously localized to the region (Konrad et al., 1995, Genomics 30:514–20) were screened for the DL gene by amplification with the IVS-3 STS. An arrayed human BAC library (Research Genetics) was screened by PCR using the same STS.

Genomic Organization

When possible, the intronlexon boundaries were determined from genomic DNA by inter-exon PCR amplification. Primer sequences are shown in Table 3. The remaining boundaries were defined by either vectorette PCR or by direct cycle sequencing of the BACs.

TABLE 3

Primers Used for Inter-Exon Amplification for Genomic Structure

| Exon | Forward Primer (5'–3') | Reverse Primer (5'–3') |
|---|---|---|
| 1–2 | Vectorette PCR | |
| 2–3 | GGAGAGGATGGCCCATGTG (67) | AGCCCCGTAGTCTGGTTGTA (57) |
| 3–4 | CTGCGGTGAGAACGAGTAC (48) | TCTGGTAGCCTCCTTTGGAA (53) |
| 4–5 | TTCCAAAGGAGGCTACCAGA (63) | CAGACCATGCCATAGATGTTC (68) |
| 5–6 | Vectorette PCR | |
| 6–8 | ACTTCAGGAGCTTCTGCCAA (69) | TCGTCCTTGCTCACTTGGG (70) |
| 8–9 | Vectorette PCR | |
| 9–10 | GGATGAATTTGAGAAGCTGAC (71) | CTGACTTGTTCGTGGTGGC (72) |
| 10–11 | GCGTCGACAGTGATGAGGA (47) | TCCACGACTCCACACACGT (73) |
| 11–12 | Vectorette PCR | |

All primers shown in the 5'–3' orientation. Seq. I.D. NOS. shown in parenthesis.

Kindreds

Clinical information for each family, with specific attention to dentition, sweating, scalp and body hair, as well as informed consent for blood sampling and DNA analyses, was obtained. Twelve families were included as having possible autosomal recessive inheritance based on affected sibships with unaffected parents and/or the presence of a fully manifesting affected female. Five of 12 families were consanguineous. Two kindreds had apparent dominant inheritance based on vertical transmission of the trait with males and females affected to a similar degree.

Linkage Analysis

Primer pairs were used for microsatellite ($CA_n$) markers (Research Genetics) to amplify genomic DNA utilizing recommended conditions. The amplicons were subsequently electrophoresed on a 7.5% polyacrylamide gel and blotted as described previously (Zonana et al., 1992, Am. J. Hum. Genet. 51:1036–46, herein incorporated by reference). The membrane was then hybridized with a digoxygenin 3'-end labeled CA$_{(15)}$ oligonucleotide, and subsequently developed using the Genius™ System Nonradioactive Nucleic Acid Detection Kit (Boehringer Mannheim).

Mutation Analysis

Primers from intronic sequences flanking exons 2–11 and from the coding region of exon 12, were designed to amplify genomic DNA from one affected individual in each family. Ten amplicons containing the entire coding region and the intron/exon boundaries were analyzed. Each exon was amplified in a 25 µl PCR reaction containing 5–10 ng DNA, 2.5 µl of 10× buffer, 6.5 pmol each primer, 0.5 mM–1.5 mM MgCl$_2$, 0.2 mM dNTPs, and 0.02 U Taq DNA polymerase (Qiagen). The exons were amplified using the following PCR conditions: 95° C. for 30 seconds, 30 seconds at the annealing temperature (Exons 2, 5, 10: 58° C.; Exon 3, 53° C.; Exon 4, 7&8, 60° C.; Exons 6, 9, 11 and 12, 57° C.), and 1 minute at 72° C., for 30–33 cycles.

After confirmation of amplification on a 2% agarose gel, products larger than 200 bp were restriction digested to obtain products between 70 bp and 205 bp (Exon3-BsrBI, Exon4-BanI, Exons7/18-HindII, Exon10-SalI, Exon12-XhoI,BsrBI). Amplicons or their restriction digest products were analyzed by SSCP analysis.

DNA from relevant family members, plus 50 control individuals (100 chromosomes), were tested for the presence of the variants by the appropriate method; electrophoresis on agarose gel, SSCP (see Table 4 for primers used) or ASO analysis. Putative mutations co-segregated with the disorder in each family and were absent in the control population.

TABLE 4

Primers used for Exon Amplification for Mutation Screening By SSCP

| Exon | Forward Primer (5'–3') | Reverse Primer (5'–3') |
|---|---|---|
| 2 | AAATAAAGGTAGCCAGACCC (74) | GTAAGGGGCTCAGACCACT (75) |
| 3 | CATGTGTTTCTAAGGAGGTAC (76) | CAACAATGCCACAAGCAGGA (77) |
| 4 | GTCCGTATGGTTTGGCTGC (78) | GCCAGGGTTTGCCAGGAG (79) |
| 5 | GTCCAGCTCACCTGTCTCT (80) | ACCGGCTCTTTCCTACACC (81) |
| 6 | TGGAGCTTCTCTGGATCATTT (82) | AACTCCAGGTGATCGATACC (83) |
| 7–8a | CTGGGTCATTCATGCCTTCT (84) | ATGGTGTGTGGAAGCCCTG (85) |
| 9 | CATGAGCCAATTCTAACTCCT (86) | CAGGACCCCAGTTCAGCTT (87) |
| 10 | CCCAGGCACTGCTAATGAC (88) | CCACATCTCACAGCTCATCA (89) |
| 11 | TTTCTACTGTTGCCCCTTTCT (90) | CCCAGCCCTTCATGTCAGT (91) |
| 12 | TCTATTGACTGTGACTTGCA (92) | CTCGTTGGATCCTTGGCTT (93) | a Includes IVS 7.

Results

Figure 5:
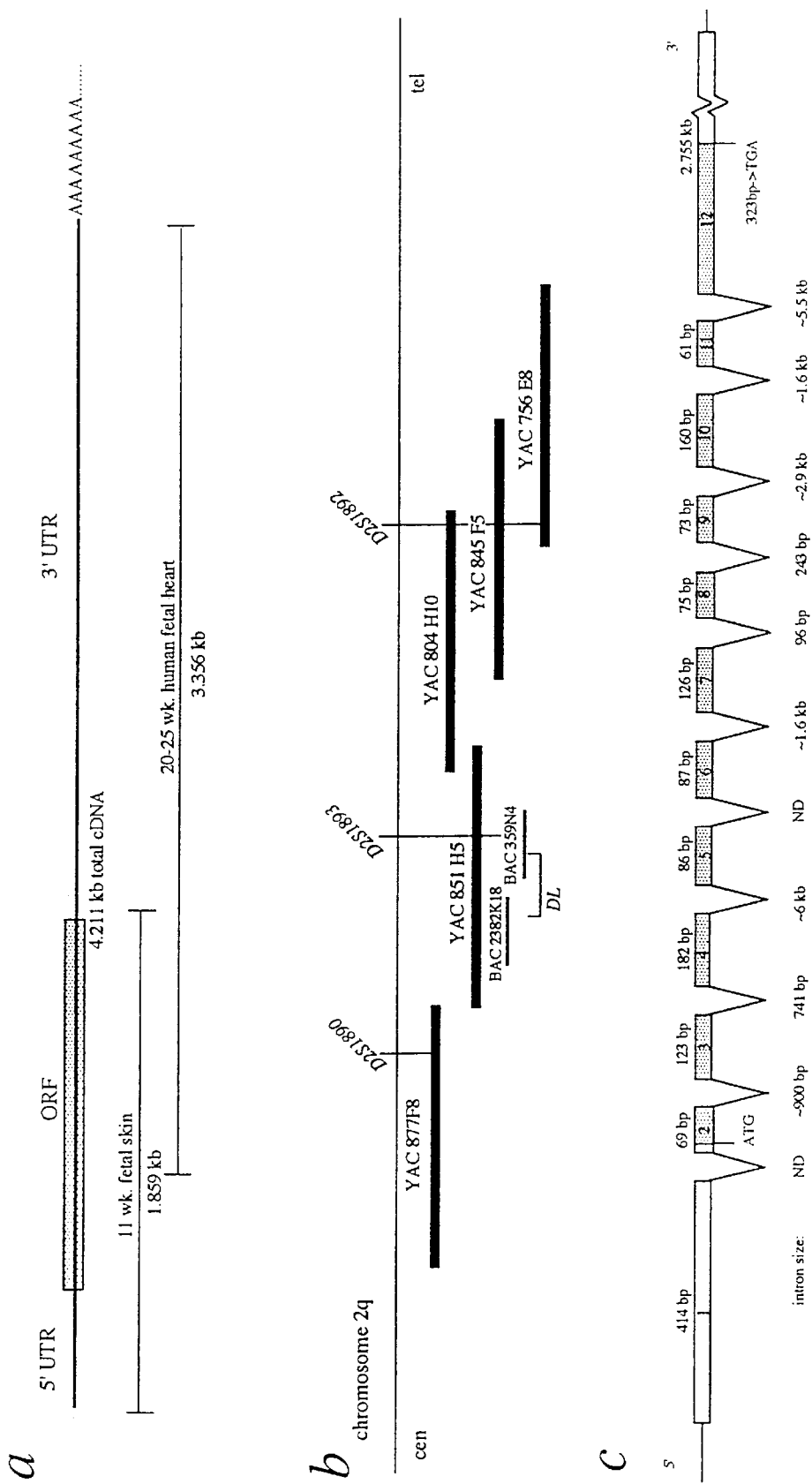
FIGS. 5A, 5B, and 5C show a schematic diagram illustrating the DL gene transcript, physical map and genomic organization. (a) cDNA from which the consensus sequence was constructed. (b) Physical map of the region with relevant genomic clones. BAC359N4, identified by a library screen, contains exons 2–12 and the 3' UTR. BAC2382K18, ascertained through data base searches, includes exon 1 plus the 5'UTR. The centromeric to telomeric orientation of the BACs and the candidate gene are unknown. Marker D2S1893 is either intragenic or 3' to the candidate gene. (c) Genomic structure with open reading frame shaded. The sizes of two introns were not determined (ND).

Using a cDNA from the murine downless gene (dl) (Example 2), a single cDNA from a human fetal heart library was identified. Additional sequence information was obtained by RT-PCR using total RNA isolated from human fetal skin. The consensus sequence of the human gene (DL) contained an open reading frame (ORF) of 1,347 bp (Seq. I.D. No. 16), preceded by a 432 bp 5'-untranslated region (UTR), and followed by a 2.3 kb 3'-UTR (FIG. 5). Northern analysis revealed only a single 4.4 kb transcript in fetal kidney and lung. The DL gene is expressed in embryonic and fetal tissues during periods of hair follicle, eccrine sweat gland, and tooth bud formation, as shown by its expression in fetal skin at 11 and 15 weeks EGA, and from a 42 to 53 day human craniofacial cDNA library. This is consistent with in situ hybridization studies in mouse embryos demonstrating expression of the dl gene during follicular morphogenesis (Example 2). DL is not expressed in either human lymphoblast or fibroblast cell lines, but is expressed in cultured neonatal epidermal keratinocytes.

Figure 6:
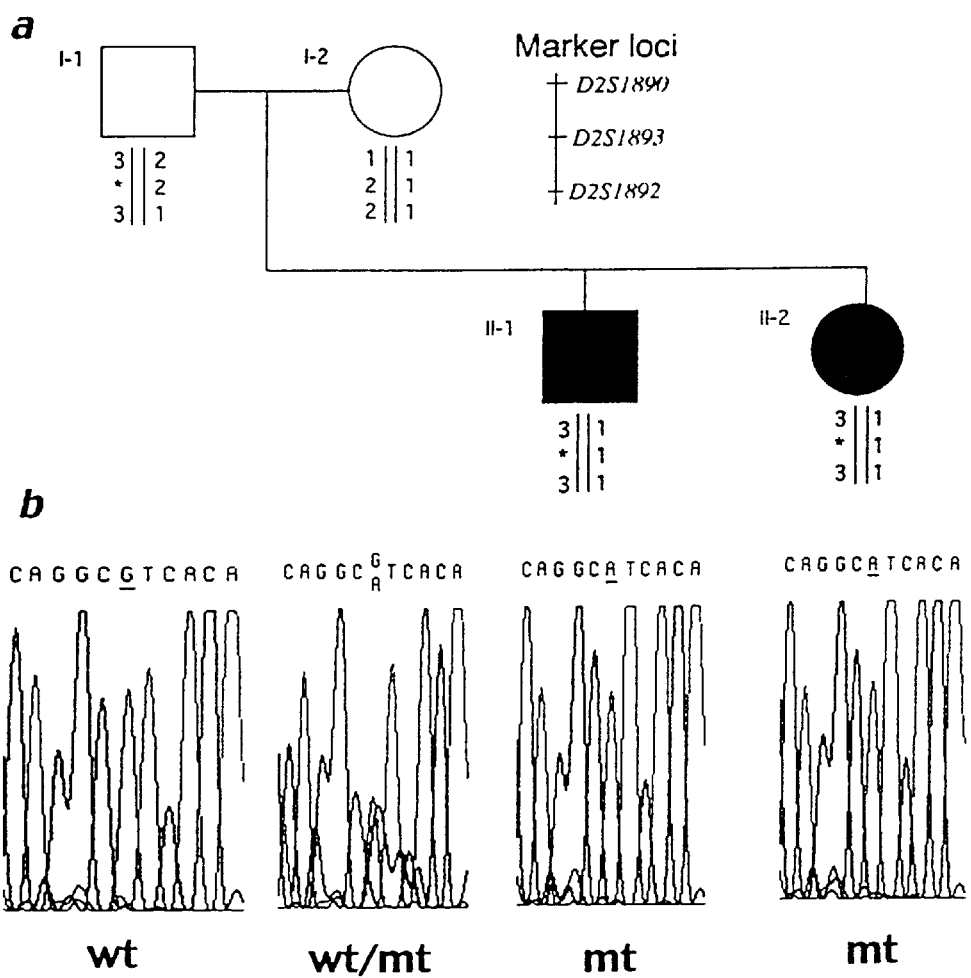
FIGS. 6a and 6b are schematic drawings representing the mutations observed in Family ED1237. (a) Pedigree with haplotypes showing lack of transmission of a D2S1893 allele from father to either affected child. (b) Partial sequence showing hemizygous wild type (wt) sequence in father (I-1), a heterozygous mother (I-2), and homozygous mutant (mt) sequence (266G→A) in children (II-1 & II-2).

The ORF of human DL encodes a 448 amino acid protein (Seq. I.D. No. 17), 91% identical to the putative protein product of the dl gene (FIG. 6). The program TMpred (http://www.ch.embnet.org/software/TMPRED_form.html) predicts a single transmembrane domain with a type 1 membrane topology (N-terminus extracellular). Computer analysis using PSORTII (http://psort.nibb.ac.jp:8800) predicts a possible N-terminal signal peptide for the murine dl protein, but no signal sequence is predicted for the human DL homolog, due to differences in non-conserved amino acids. As with the murine dl gene (Example 2), a similarity search using protein-modeling programs pfscan (http://www.isrec.isb-sib.ch/software/PFSCAN_form.html) and Pfam (http://pfam.wustl.edu) reveals a partial match (pfscan N=6.9) with the TNFR cysteine-rich region (Prosite-PS50050), in the ligand-binding region of these receptors. In addition, some similarity to a death domain (PS50017) was identified (Pfam E=5). Similar to members of the TNFR family, this potential domain resides in the carboxyterminal end of the protein, and may trimerize and interact with down-stream signal transducing proteins. Although individually the matches for each identified domain are not statistically significant, the occurrence and location of these two different domains within this predicted type 1 transmembrane protein suggest that it may function as a receptor and be related to the TNF-receptor family.

The human DL gene was localized to a position 10.1 cR from marker AFMA037YB9 (likelihood P>3.0) by radiation hybrid mapping, consistent with the independent localization of an homologous EST sequence (W73914) to reference interval D2S293-D2S121 (122.4–127.9 cM). Single families with autosomal dominant and recessive inheritance have been mapped to the 2q11-q13 region, which contains this interval. Genomic clones containing the gene were identified by screening both a human genomic BAC library and YACs from the region (FIG. 5b).

The DL genomic structure indicated the presence of twelve exons with flanking intronic sequences (FIG. 5c). The full coding sequence of the human DL gene is shown in Table 5, with exons 1–12 identified, and separated from the intervening sequences.

TABLE 5

Human DL Exon/Intron Sequence

Exon 1 (5' UTR underlined) (Seq. I.D. No. 94)
TTTTTTTTTTGGGGGCAGACGGCCGAAGAGCCAGGTGTGCCAAGGTCATATGGCAGCAGGGCTGAACGTGC

CCGCTCCAGCCTCTCCAGTGCTGGAAGAGACCTCTAGATGGAGCAGGTGAGTTTGCAATTAGGGAAAGCCCC

TABLE 5-continued

Human DL Exon/Intron Sequence

<u>TCGGCAAGGACTGAGTTTCCAAACTTGCAGACAGGGCAGGGAGCGGTCAAGGAAGAGTTCCCGGGAAGCCCT</u>

<u>TTAAACGGAAAGGAAGCGGGGCTAGTGTCAGAGAGGTGTGACAGGTCCCAGTCAGCCCTGCTGGCCCCTAAG</u>

<u>GACATAGAGTACCTGCTTCTGAGAGGGCTGCCACGGTGGCCACCTGTGAAGCCTGTCACCCAGAACTGGATG</u>

<u>GTACCTGACTTTCTTCATAGACCCATCTTCTGCTGGGACTGAAGCTGACCTCCAACAGAAGCCAG</u>

Intervening Sequence (IVS) 1 (Seq. I.D. No. 95)
GTAAGCCCTGGTCCTTTCCTCTGGTTTTCTAAACTCTTCAGCTGTGGCCGAGACGGAGGTGTCATGGGCTGGG

AGAGAGGCTGGGTGCATTTTTGAAATGCATGTCATTTTTGGGTTGCGTTTGAA...GGTTTCNCCAAACCCTCTG

AGCACGAGAAACACAATCACTANCCTCGGGTTTAACCTTGGGCCCTCCGTGTGCTCCTAGCCTCCTNTCAGGC

TCCCTCCCAGGCATGGCTGCNAGGCTGGGAAGGCCCCAGAGTCAGCCCAAGTGGCATGGGTNCAGCTTCAGC

TTCATGTCTGCTTTTCTTTTAGGATGTATAGTTTCCCCTCTGTTTGCTGGAAGGCACCTTATATCCAGTGGGGT

TAAATAAAGGTAGCCAGACCCCCGGCTGGGGTGCTACCGCCAGTGCCCAGCTAATGACGCATNNNTTCAG

Exon 2 (5' UTR underlined - remaining is coding) (Seq. I.D. No. 96)
<u>GTGAGCCCCTTGGGAGAGG</u>ATGGCCCATGTGGGGACTGCACGCAGACGCCCTGGCTCCCCGTCCTGGTG IVS 2 (SINE-MIR repeat - 112 bp - italicized) (Seq. I.D. No. 97)
GTAAGTGGTCTGAGCCCCTTACCCCCACAGCACCCTCATCCTCATGATGGTTGGA*CTGTTTCTTGGCCTCTTCAG*

*CTGTAAAATGGGAATGCTGATCATAGTCCCTCCTCCACAGGGTTCTTCTGAGGGTGAAATGAAACCAGGCCTGCAAAG*

*CACAGAACTCTGCCC*CAGGCTGAAGTTACATTGATTTCGTTGGTAGCTCCCTTCATAGGGTCTCATGGATATAA

ACGTTCTTGATTGCTTGTTTGTGGTGTGATACACACAGCCCTGTGTCTATGTGATGAGCTCATGCTTGGGGGC

CGCGCAGCTAAGAAAGACTTGGAAGACTCAGACCCCTACCCCCATCCTCCTGGACACGCCGGTGTTCTGAGG

AGCCACTGTATTAGAGGCTCAGTGGGGGACAGGGGCGCCTCCTCCATGACCTTGGCAAGTGCGTTGATGAGG

AGAACTCANAGCAGGCCTTGATGGTGGGATGGGGCTTGGCCAGCAGGGGTGAAGGCAGGGTGGTTCTAGTGG

GGGCTGGCCGTGCCCANGTGGATCAACCAGGAGCCACTGGAGACTTAACAGCAGTGAGCACTNACAAGCGG

CACCTTCCCAGACCGAGCCCCCAGCAGAGCCCCCACCGCAGGGCACCCCCTTCCTATGTCAACCTTGGGGTCT

TGCAGGAGTCACATGTGTTTCTAAGGAGGTACGGAGGCCACAACACCCCCCTTTGTTGGCAG

Exon 3 (Seq. I.D. No. 98)
GTGTCTCTGATGTGCTCAGCCCGAGCGGAATACTCAAACTGCGGTGAGAACGAGTACTACAACcAGACTACG

GGGCTGTGCCAGGAGTGCCCCCCGTGTGGGCCGGGAGAGGAGCCCTACCTG

IVS 4 (Seq. I.D. No. 99)
GTAAGGACCCAGCCCTCCTGGAGCCTGGTGCGCTCTCAGGGGAGGCCTCCTGCTTGTGGCATTGTTGCCCTGA

GCCTGCCTTGCTGTGTGAGGGGATGCCAGGGTATATCAAACCAGCCGGTCACGCTCCCTGGACGTTGAGATT

GATGGCAAGAGCTGCCGTGAGCCCAGGAATGGCACTCACCAGCTAAGCATTCATAAACAGATTTTTCAGGAG

TTCTGAAATGTTTTTAAAGGATCACTTTCCCACTCTACCCTGATTAAATGAGCGTCAGATCATCTGATTGGAA

GCAGGATTGAAATATTCTCCAGTACTAGTACATTTTTTCCTGAGTGCTGCATCTCCCTCCGCCTCTGGGCAAG

CTAAGCCTGAGTGTTCTGTTCAGCACTAAGGGAAACCTCCGGGGTTTCAGTGTCCGGTTCTTGTAGCAAGCTG

AGGAAAGTCAGATGCCAAGTGCTACCTGCACTGCCTGGGCATTCCAGCAGCTCGCTGAATTCATCTCGGGGA

GGCTCAGAAAAGGGGCAGCATCTGGAGCCTGAGAGTGGCGAGGAGAGGGGCAAGCCCAGAGCATGAGCTGG

TTCCTGGGGGGTTTTGCAGTTAGGACAACTCAGGAAACCAAGGCCCGGCAAGAGTAGCTTCTGGAGACAGCT

GGCACGTCACTGCCCAAGGACTGTGGGCCGAGTCCGTATGGTTTGGCTGCTGCACTCACCTGTGTCCCCTGTC

CTCTTTCCCTGGACAG

Exon 4 (Seq. I.D. No. 100)
TCCTGTGGCTACGGCACCAAAGACGAGGACTACGGCTGCGTCCCCTGCCCGGCGGAGAAGTTTTCCAAAGGA TABLE 5-continued Human DL Exon/Intron Sequence

GGCTACCAGATATGCAGGCGTCACAAAGACTGTGAGGGCTTCTTCCGGGCCACCGTGCTGACACCAGGGGAC

ATGGAGAATGACGCTGAGTGTGGCCCTTGCCTCCCTGG

IVS 5 (Seq. I.D. No. 101)
GTAAGCACAGGCCCTCCTGGCAAACCCTGGCATGCTTTCTGCAGAAAACCCCGAGGGGCTACGGGCAAGGAC

CTTGGGAACAGGGGTCATGGATACTGCAGGCCTCGGTGCAGCCGCACACCTGGCCTTGGTCCCATCCCACAA

GGAGCAGCATCCAGGACGGAGAGTCCTGGCCCCTCCGGTGGACAGGCAGCCCATCAGGCTCTGCCTCTGTGT

CTCCTAAGTGGCCATTAACCATCATAATATCTTCTGACCACCAAAAGGAAACAAATTGCTTGAATACTTACAG

TGCAGTAGCCCATGTGAAACACTTTGGGAAAAAGAAAACTNNAATTTNATGCAAAAAGCAGTATTTTNAGTA

TTCTGGNAACACTCTGGNNAANCTACTAATAANNTANATNTG...AGAAAAGAAATATNANTGANGAGATTAT

GANNNCGAAGNNAAGNNANGNANAANCANANNAGGNTNNAGAAAATGAGGTTGNNAANGANTNATAANAT

AGNACANNGNTGATATNCATNGGAAAGTAAACNGCNTGAGNANNAGTGATTTGTGATNGCCAGGGTATTCN

TNGAGGGAAAACANGACTATTGGANCAGANNGTGNGGAAAGGNACAAACGNTGTNTNANCATAGANAANN

TAGAGTTGNTGGGTGGGCATTNNAANNAGCNGGTAAAGAATAGCTTGNAAGTNGNCAAGGGGTNCCAGAGG

CAANNNTAATGCCTATANATCCCATAAGNNTGCAGGCTANTGGNGANGGTGCTNACAAAGAGCATGTTCCTC

CTCCAGGAAGGTCTGGCCTTNGTTGGTGTNACCCCTGGGGGGCTAANCAGGCCNTACATGTGGGGGCACAGG

GATATTTCTGGTGNATGATGTGATGGCACACACACTAAACACAGCCACCAGAGAGAGGAACCAGAAAGGGG

CTGAGATCAAAAGAAAGGCCCACGTTGGCAGCTCAATATTGTTAAAAGAATGCTCCATTTCAAGACAGGCTG

AAACCCCAAGGAAACTGAGTGGACAGAGCAGGTGACTGAGTGGGCGTGGCCTCATGCCCGACTTGATTGTGG

GCCTGCAGACTGGCCACCGTGCTCTCTGCACCAGTCCCTGCCTGTGTGCTGTCCAGCTCACCTGTCTACTGTT

TTGTCCTTGTGCTCTCCNCCGTAG

Exon 5 (Seq. I.D. No. 102)
CTACTACATGCTGGAGAACAGACCGAGGAACATCTATGGCATGGTCTGCTACTCCTGCCTCCTGGCACCCCCC

AACACCAAGGAAT

IVS 6 (SINE-MIR repeat - 104 bp - italicized) (Seq. I.D. No. 103)
GTGAGTGTCTTTGTCCTTCCACCAGCACGGTATTTGTTCAGGCACGGATCTCTTTCACTACAGAGGGTGTAGG

AAAGAGCCGGTCCTGGCACCTGGACAAGGTGAATCACAGTAACAGCACTAGTGAAAGTGCTCCTGTGGCCTG

TCCAGGCAGGTCTATGAAGGGAGGGGCGTTTGCCACATCTGAGC*CTTGAGTCAGAGGCTGAGGTTCTAGTGCAG*

*GTTGGCCACCAGCTACCTGACAAGTCACTTMCCTCCATGAGCCTCGGTTTTCTCATCGGTAATATGGGGGTGA*...AGA

AAGNACAATANCGATGACTCTTTAGGGTTCATTAAACAGTCTAAGAAATACAAATATTTAGCTCCCCTCAGC

CATCACTGCCTCAGGCCCATTCATGATCATGAATCCAGATCCATGAGCTCTGTGGCAGCGTGCTTTGAAGGTG

GAGCTTCTCTGGATCATTTGAGGGACTCTATTTTGCCTTGCAG

Exon 6 (Seq. I.D. No. 104)
GTGTGGGAGCCACTTCAGGAGCTTCTGCCAACTTCCCTGGCACCTCGGGCAGCAGCACCCTGTCTCCCTTCCA

GCACGCCCACAAAG

IVS 7 (Seq. I.D. No. 105)
GTGAGGAGGGTGCTCAGGTATCGATCACCTGGAGTTAGGTGGTACTCGGATGAAAGCTCAGAAGAGGAGAG

GAAATGATCATGAGTGATGATTATGGTGCGCTTCCCCACCTGGCCTCACCTCCCTAATGTAATTGAATGACAT

GTTGCCCCCCGTGCAGGAAGTCATTATATCTGCAATCAGAGTTGATCCCTCTATGGGTGTCCTGGGACCGCTG

GGAGGTGCTGGTGGTGAAGGCGGGGGCATAGCGGCAGGTGGACAGCACAGGCAGCTGCAAGCCCGGCCAGG

AGGAGAGACCAGGCGTCCTGGGCTTTGGTTTGGCCGNGAGTTAACAGCAATTCTATCACTGGTTTTCATATAA

ACATGCTGACCATAGCACTTTAATATTAACTTGCANAANGTNCATTTTCATTCTNCCTTAACCAGGGAAGANG

TABLE 5-continued

Human DL Exon/Intron Sequence

GGATCGNGGAGGACCCCAANGTTTANTNTGCCTCTCACANTTAGNCCCCCACNTGGCTT...GNCNTNAAGGTT

GCCAAAGCAGTAGNAGCGAGAAGCAAGCTCCCTTAGGAACAATNAGGTANCCCCAGAAAAAGTCTGGANAG

GCCAAGTCTGAGGGCAGCGAGCAGGGGTTGTGGGCAGTCCTGGTCTGGCAGCCAAAACCAGCGCGNAGGATT

TGGTTCTCAGTCTAAGCAAGCACCTCAGATTTCAGGGTTCCCTGAAAGCATCCCAGGGGCAGGGCCATTGCTT

CCAGGGGCCGGAGTCCTGGAGGGAAGACCAGCAGGGATCCTGAGCTCTGGGTCATTCATGCCTTCTCTCCAC

CCACAG

Exon 7 (Seq. I.D. No. 106)
AACTCTCAGGCCAAGGACACCTGGCCACTGCCCTGATCATTGCAATGTCCACCATCTTCATCATGGCCATCGC

CATCGTCCTCATCATCATGTTCTACATCCTGAAGACAAAGCCCTCTGCCCCAG

IVS 8 (Seq. I.D. No. 107)
GTGACGGCCCCCATGCGCCGGTGCCCTGCCTCCTGGACTCTCCGTCAACTCCCCCTGTCGGAGAGCCTGGCTG

CTCACTCCCTCCTCTCTCCCCAG

Exon 8 (Seq. I.D. No. 108)
CCTGTTGCACCAGCCACCCGGGGAAGAGCGTGGAGGCCCAAGTGAGCAAGGACGAGGAGAAGAAAGAGGCC

CCAG

IVS 9 (Seq. I.D. No. 109)
GTCTGTGAACCAGGGCTTCCACACACCATGTGCACGGTGCCCATCTCTGGGTGGAGGGCGTTCCCAGAAGCA

GCCTCCTCGCTGCTTCTGCTCTCACATGCTGAACCATACTGTGCTTACCGTGGGGTGGTGCCACACAGACACC

GGGCAGCTCTGCCCAACAGGAAGAGCAGGGTTGGGCTGAGCGCANAGCCATGAGCCAATTCTAACTCCTATC

TCCCCAACCTCCCCATTTCCCTGCAG

Exon 9 (Seq. I.D. No. 110)
ACAACGTGGTGATGTTCTCCGAGAAGGATGAATTTGAGAAGCTGACAGCAACTTCAGCAAAGCCCACCAAGA

G

IVS 10 (Seq. I.D. No. 111)
GTATGTGGAAGCCCCCACACCAAGCTGAACTGGGGTCCTGTGGATCCTGAGCAGGGAGGGGTTNCCAGGGTG

CAGCCGAGTGAACTGACAGGCTAGCCTGGGACACTATGGGGACGTTCGGCGACAGACAGTCCCCACCACCTC

TTTGCTGACTGGCAGGGGTCAGGTGGTGTGAGGAGCCTGTGGAAACAGCTGCCTGCTGCTCTCGGGTCAGGC

CCCTGTCCCTGCATCCTGCCAAATTCCCTGGGCCTTCCTCCTTAACATCCGAATTCCTCATGCCCCTTCTCCAG

ACTGGGAGGGCAGAACATAAAGCCAAGGATGCATGCCTGTTGCGGCCAACACACCAGTACCACCCGTGCCGG

TGCCAGTACTGCTGCCACCGTAATGCTGGTAACAACCGTGGTGATGACGGCTAACAGCATTTGGTGCCTACTG

CCCACCAAGTGCTGGGCTAGGGCTGTGAACACATCCTNCCTTCCACCAGCCCANGAGCAAGGTGCTTGGAAT

CATCCCTGGTTATAGGAATACCACACTGAGGTATGGAAGTTGTCACTCGCCCAAAGTCACACACTAGTGAAC

ACANGGCTTGGGGTCCGAAGTCCANGCTCCCAANGAGCCACATGGNGNTAAANA...GGTNAGNCAGGGTCAC

CCCCCTAAGTTCCAAGAGGGGGCTTTTCNAGGCACAAAGGGTTCCATTNAGGTTCCCTTTTCAATGNCTTCC

AGAGAGCCAGCATGGATTTCAGCGCCAGCNGCATCCAATCTGTTTGCTTTAACATGAAGACACCAGTTGAAC

TTGGGTGCTTACTGGGATTAAATACAGAGATCTAGGACATATTCAATGAACCTTCACGGAGCATCCATTGTGT

GTCAGGTAGCAGGGAAGGAGAGGCCCGTGGATGCCTCCCACCCGCAGTGGCAGCCCCAGCCCCTTAGACGCC

TGCAGGTCACCCACCACGGACTTGTTTGTTTGGAAAGAAGCAGGAAGCCACCGGTGTATGTCTCGTCTCATGT

CCCCTGGTCCCGTGCCCACAAGGTGCCCAGTAAACACCTGAAAAACAAGTCATTGCCCCCCACTGTCCACAG

CTGGGCAATGGACAAGTTCACCACAGGAGAACTTGTCAGGGCTGCAGCCCCCCAGGCACTGCTAATGACCA

TCGCTCTTGTTTTTGCAG

Exon 10 (Seq. I.D. No. 112)

TABLE 5-continued

Human DL Exon/Intron Sequence

CGAGAACGATGCCTCATCNGAGAATGAGCAGCTGCTGAGCCGGAGCGTCGACAGTGATGAGGAGCCCGCCCC

TGACAAGCAGGGCTCCCCGGAGCTGTGCCTGCTGTCGCTGGTTCACCTGGCCAGGGAGAAGTCTGCCACCAG

CAACAAGTCAGCCGGG

IVS 11 (Alu repeat - italicized) (Seq. I.D. No. 113)
GTGAGGCTCCTGCAGGTGCCATGATGAGCTGTGAGATGTGGCTCCCTCACAGCCGCAAGGACTAAAACTTTC

TTATTGAATCAGCTCTCCTGCAAGACGGGGTGTTTCTCCCAGAAGTCCAAGATAGGAGACCTGGACAGTGAC

AAGTTCACAGCAAGATAGTCAAAAGGGAAAAAAACCCTTTCGTTTTTGAG*TTTTGTTTTTTTTTNGGNGATGAN
AGNCTNG...*

Exon 11 (Seq. I.D. No. 114)
ATTCAAAGCCGGAGGAAAAAGATCCTCGATGTGTATGCCAACGTGTGTGGAGTCGTGGAAG IVS 12 (Seq. I.D. No. 115)
...AGAGTGGNNGAAGAGNGAAGGGAGGNGAAAAGGGGGNGAGNGAGGGAAGGAGGNGGGAANNNGGAGTG

AGGGGGGGAAGGGGNAGAGNGGGNGGNAGNGNGNGGNGAGNGGGANAGNGAAAAGNAGTGAGANGGGAAG

GNANAGNGAGNAGGGGNNANGAGAAAGNGGGAGNGTAGGNGGCGATGNGNNNGGTNGAAATATTNANAGA

AATTTTTTCAAATAATTTTTATTTCATTTAAATAATTTTTCAGTGTTGACCTTCTATTGACTGTGACTTGCAAC

ATCTAACTGTGGCCATTGGTGTCTGTAG

Exon 12 (3' UTR underlined) (Seq. I.D. No. 116)
GTCTTAGCCCCACGGAGCTGCCATTTGATTGCCTCGAGAAGACTAGCCGAATGCTCAGCTCCACGTACAACTC TGAGAAGGCTGTTGTGaAAACGTGGCGCcACCTCGCCGAGAGCTTCGGCCTGAAGAGGGATGAGATTGGGGG

CATGACAGACGGCATGCAACTCTTTGACCGCATCAGCACGGCAGGCTACAGCATCCCTGAGCTACTCACAAA

ACTGGTGCAGATTGAGCGGCTGGATGCTGTGGAGTCCTTGTGTGCAGACATACTGGAGTGGGCGGGGGTTGT

GCCACCTGCCTCCCAGCCACATGCTGCATCCTGA

<u>AAAGCATGCCTGTGGGCTGTCCTCCCAgGACAAGCCAAGGATCCAACGAGGGCTCTGGAGCTGTGAGTGGTG</u>

<u>CCAAAAGACTGCCAAGAATCaAGGCTTTTGTGATATGTCACCGTATGCCTTAGGATGTTCAAGGAGCCAGACG</u>

<u>AAATAAGGCCTGTCTTCCAATTTAACCAAAGATAAAGGACTAGAGCCGGGATACTTTCANATGCTCGCCTGT</u>

<u>ACCTCACCAGGCAGAGTAAATATCTACTCACTCATACAGCCAGCCCACCAGCCCACCATTAACTCACTGAAC</u>

<u>AATGAGACAATGTNGAGGACTCAAATGAATCAAACCCCGTGGGAATGACAGANTGAAGAATCTGGTCCCTGT</u>

<u>CTTTAAGGAGTTTGCACTCCAGTAGAAGACAGAAGGAACGTATGTTTACAAACCACTTCACTGGAAGACGTC</u>

<u>AAACAAGCTGAATGAAGGGGCGCTTAGAAAACTTAATAGAAGTTCTAAGCGGGAGATGACTCCCTACTGGG</u>

<u>ATGATGAAGGATGGCATCCTAGTGAAGAAGCAGCTCAAACATTTTGATAAAATGGCAACAAAATGCAGACAC</u>

<u>CCTGCTCCAGGTATTATTTCAGGTTTAGTACAAGTCTGTTAATACCCTATGTGGTTTCATTAGGATAACTTTTT</u>

<u>ACCTATCCTTGAGGTCATCCATATTCTTACAGGCCTTCCAGTCAATAATGGAAGAGCTCACTCTATACAAAAC</u>

<u>CAATATGCAAGGCATGTGTTTGTCCAAGCAATTGGATGTGTGCAGTAGCCAATTTCATTTACTGCATTACTCT</u>

<u>TTGGCCTGGGAACCCTGTGGTCTGCACTACATGTGAATGGCCTTCCACTTCAAGTCTTAGGCAGATTTGACCT</u>

<u>TTTAGGGGCAGCAATGCTGAAGGACACAGCAATTTAAATTATAATGTGTCAGGCTGTGTTTTCACTTCAAACA</u>

<u>TGTATGAGTAGTCAGCTGTAATTAGAGAAATGATGACTTCCTAAGAGTTCAGCCACGCATAATTCTAGATTTC</u>

<u>AAGAGCATCTAAGACTTGTGGATTAGCCTCATGGCATGAGAGTTTCAGACTCAGCCTTCTGAGCCAGTCAGG</u>

<u>GAAAGTGGAGTTCTGCAGCGCAAATGAGAGCCTGGGCTTGGTGTCGAGGGAGCTGGCTTCTAGTTGTGCCAC</u>

<u>CTTGGGCCTTGTCTTTTCCTCTCTCTGCCTCAGTTTCTCGTCTGCCAATGAGATGTTAGTTAGTGATTCTATAA</u>

<u>TTGGGGCAGGTAGGGTTCAGGTGAGCAAAAAGAAAGTGGAGCTATAGGAAATGCCAGGCCTTTGAGGTGCTC</u>

<u>TATGGAAGTCAACACAGTGTGGTTTGTCCATTTAAATGGAATAAAAACAGAAAAACTCAGACTTGGCATTT</u>

TABLE 5-continued

Human DL Exon/Intron Sequence

TCACAATAACTGCAATGGTTTGACATAACATTTATAGGCAGAAAGTTAATAAACTGGCATTGTTCTTGGCATA

TTATTGTACTATCCCTGTAACTGCCAAGAGCTCAGGAGCCAGGCTAGTGATCACACCAGGGGTTAGAGTTCA

CTGCTGAACTCCCTGATGGCAGGTCTGTGTTTATTACTACATTAAAACAAAGTCTCTGACTTATAAAGCGAGG

TCGTAAAAATTACAAGTTGCATGACTGAAAAAATGCTTTAGGGGGAAAATCAGTCATATCTTTAACACCAAC

AAGCAATTTCCCACCAACGAATGTAGTACATACTGTGAGAGGATCATAATGAGGTCCTGAATATTTAATATC

ATCATTTACTGTGTCTGTTTGCTGCTGTTTTTCGAACCTATTTGGTTTACCCTGCAAGCTAAATACTCCACGGC

AGANCTTAATTATCCTTTTAATTCCTCTTTGAAATCCTGTGGTGCCCCCTTCCCCCTGCCTTGTGATGATGATG

CCTCCTCAGAATGTTTTCAGCGAAAGAGTGGGGTGGCTGTTCTCTGCTCCTGGTGCTTTGGCCTCATTTCACA

CTATTAGAATTCTGGGGCTGTAAGGCCAGCCAGTGTCAGCTCATGTTCCATTGGCTCTCCACCTGCCATTTTT

AGGGAGCTATTCCTTATATAGTTACAAATTCCCTTGTCATTTACTTATTTGGAAACATGGGATTTACTCTGAC

AAGCTTTAGCCTATGTTATGGGATTCAGAACAATGAGATCATAATAATTCTCACTGACCAAAGCTGGGACTCC

ATCCTGCCATTTTTGTGTGGAGATATTCATAATTCTGCAATACTTTAAAACATTTAGAAAACACCCCAGGGTA

GGTCTGTGGCCCTTANACAGTGAAAGTCTTAATTGGCAATATTATTTTTGCTAATTCTGGATATATATAACNN

ATTATATTTATAAATCTCAATAAACCCCATTTANTAAAAAAAAAAAAAAAAAAAAAAAAAA

To identify families whose disorder may map to the candidate region, three microsatellite markers were chosen for haplotype analysis. One marker (D2S1893) locus is present on the same YAC (851H5) as the candidate gene, while two others (D2S1890 and D2S1892) flank it (FIG. 7b). The disorder and marker loci showed co-segregation in seven of twelve families with recessive inheritance. The genomic DNAs from these families were analyzed for mutations by single-strand-conformation-polymorphism-analysis (SSCP). Two families displayed dominant inheritance, and their disorder co-segregated with the markers. Affected individuals from these families had better heat tolerance and fuller scalp hair than individuals from families with recessive inheritance. Recessive families not co-segregating with the candidate locus may have mutations in the human ortholog of the murine crinkled (cr) gene.

Seven variants, two of which were detected in the control population were identified and are shown in Table 6. Both dominant families and three recessive families had putative mutations. A single change was found in each dominant family, involving a base pair transition in exon 12. One, a nonsense mutation (Arg358Ter, where Ter stands for termination), if translated, would truncate the predicted cytoplasmic portion of the protein. This is similar to the effect of the dominant mutation ($Dl^{slk}$) in the mouse, which truncates the protein prior to the possible death domain (Example 2). Previous experiments demonstrated that co-expression of a truncated TNFR with a wild-type receptor results in a dominant negative effect on function (Fisher et al., 1995, Cell 81:935–46; Tartaglia & Goeddel, 1992, J. Biol. Chem. 267:4304–7), presumably due to lack of homo-trimerization of the death domains. The variant in the second family, a non-conserved missense mutation (Arg420Gln), is also in the predicted cytoplasmic portion of the protein within the potential death domain. Dominant negative mutations have also been described in the FAS antigen, a member of the TNFR family, in patients with autoimmune lymphoproliferative syndrome (Bettinardi et al., 1997, Blood 89:902–9; Infante et al., 1998, J. Pediat. 133:629–33).

TABLE 6

DL gene variants detected

| Family | Sequence Change | Exon | Predicted Effect |
|---|---|---|---|
| Putative Mutations | | | |
| ED1206 (AR) | IvS2 −25 to −8 del (homozygous) | — | reduction of poly-pyrimidine tract of acceptor splice site |
| ED1237 (AR) | 266 G→ A 175-356 del* | 4 | Arg 89 His |
| ED1238 (AR) | 259 T→ C (homozygous) | 4 | Cys 87 Arg |
| ED1012 (AD) | 1072 C→ T (heterozygous) | 12 | Arg 358 Ter |
| ED1029 (AD) | 1259 G→ A (heterozygous) | 12 | Arg 420 Gln |
| Polymorphisms | | | |
| | 1056 C→ T | 12 | Cys 352 Cys |
| | 750 C→ T | 9 | Ser 250 Ser |

*deletion includes at least exon 4 but exact size is unknown.

AR=autosomal recessive; AD=autosomal dominant

Both affected individuals from families with known consanguinity were homozygous for their putative mutations, and their parents were heterozygous. One had an 18 bp deletion at the 3' end of IVS-2. The deletion alters 7 of the 10 bp that constitute a polypyrimidine stretch at the acceptor splice site, reducing the number of pyrimidines from 8 to 3. The importance of an intact polypyrimidine tract for normal splicing is supported by both experimental evidence and by splice site mutations described in human disorders (Beldjord et al., 1988, Nucleic Acids Res. 16:4927–35; Coolidge et al., 1997, Nucleic Acids Res. 25:888–96). The deletion is likely to result in skipping of exon 3 or use of an alternative splice site, but no relevant cell line is available from affected individuals to directly examine RNA. In the other family, a homozygous Cys87Arg mutation results in a non-conservative change in the extracellular domain, possibly affecting intra- or inter-chain disulfide bond formation. The two affected siblings in the third family (non-consanguineous) appeared to be homozygous for a 266G→A mutation, which results in a non-conservative change (Arg89His) in the extracellular domain. The affected children were heterozygous at flanking polymorphic loci, but failed to inherit a paternal allele at the D2S1893 locus (FIG. 6). Sequencing revealed the mother to be heterozygous for the variant, while their father was hemizygous wild-type (FIG. 6). Thus, the affected individuals are compound heterozygotes, with their paternally inherited allele containing a large deletion of indeterminate size.

In summary, mutations in the candidate gene, can produce both recessive loss of function, as well as likely dominant negative affects. One hypothesis is that the protein functions as a multimeric receptor and is related to the TNFR family. Of relevance, ectodysplasin-A, the abnormal protein in X-linked hypohidrotic ectodermal dysplasia, shows a highly significant match (pfscan N=9.9) in its extracellular domain with the TNF family profile (FIG. 4).

Analysis of dl and DL Protein Sequences

Figure 8:
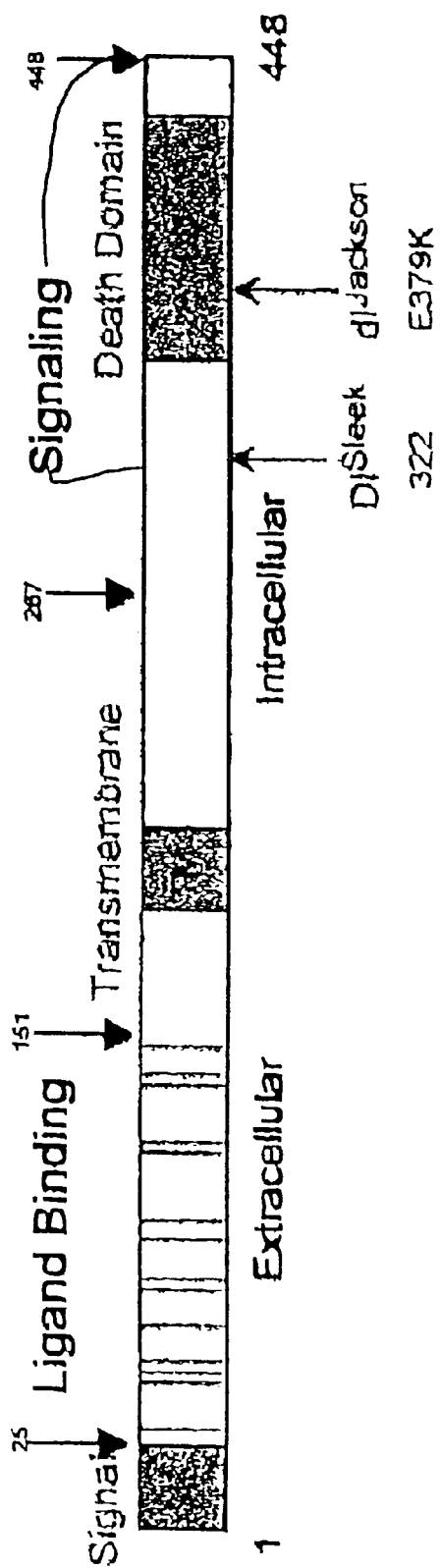
FIG. 8 is a schematic diagram illustrating domains of the dl and DL receptor proteins.

In FIG. 7, the amino acid sequences of the encoded mouse dl and human DL protein (see Example 3) are aligned and compared, and a schematic diagram of the dl and DL proteins is shown in FIG. 8. The signal sequence of dl (FIG. 7, first 24 amino acid residues) is involved in insertion of the protein into the plasma membrane in an appropriate orientation, but the signal sequence is cleaved before the receptor becomes functional. A signal sequence of this type is found in many proteins, and although it serves a function in the localization of the protein in a cell, this sequence is not a unique characteristic of the protein, and can be substituted by other signal sequences. In vitro assays which are designed to determine binding of the functional receptor to a ligand do not require the signal sequence. Hence, in some embodiments of the dl sequence, the signal sequence can be eliminated altogether. No signal sequence was predicted for the human DL homolog, due to differences in non-conserved amino acids.

The predicted ligand binding region of dl and DL are shown as amino acid residues 25–151 in FIG. 7, although the minimal binding region may be smaller than this. Also shown in FIG. 7 is the cysteine-rich region (residues 30–71, boxed with cysteines in bold), the potential transmembrane domain (residues 190–211, underlined). In addition, the open box (residues 410–431) identifies the potential death domain region. Some amino acids are conserved between the human DL and mouse dl, and would be less likely candidates for mutations in variant peptides that retain the biological activity of DL or dl. However certain amino acids appear not to be crucial by sequence comparison (e.g. residues 25, 28, 37, 46, 51, 58 and 67). However the cysteine residues in the binding region (and the spacing between them) are thought to be important.

The binding region can be subdivided into a TNF receptor type fold (the region containing the first 6 cysteine residues (amino acid residues 25 to 71) and the remainder of the sequence (amino acid residues 72 to 151). Studies of other TNF receptor type proteins indicate that either of these domains could individually bind ligand. (Chen et al., 1995, *J. Biol. Chem.* 270:2874–2878; Corcoran et al., 1994, *Eur. J. Biochem.* 223:831–840). The protein domain prediction was performed using PSORTII (http://psort.nibb.ac.jp:8800/) as described by Chen et al. (1995). Sequences consisting of the ligand binding domain, or either of the subregions of the binding domain, can be used in assays to detect binding of agonists or antagonists to the receptor.

The potential transmembrane domain (FIG. 8) is underlined in FIG. 7, and extends from residues 195 to 211. This region is not believed to have any properties unique to the DL or dl proteins. A similar domain is found in many proteins, and it could be predicted that replacement of the transmembrane domain with that of another protein would have no significant effect on the biological activity of the DL or dl protein.

The regions immediately upstream and downstream of the transmembrane domain (for example residues 155 to 194, particularly 155 to 165, and residues 212 to 266, particularly 222 to 266) are not very well conserved between human and mouse, and therefore are likely regions in which mutations can be made to produce variant proteins that preserve the biological activity of DL or dl.

The domain from about residue 300 to 448 is considered more critical to the function of the DL and dl proteins. This domain is well conserved between mouse and human, and homology searches of the sequence databases indicate that this region is similar to important signaling regions of other receptors. Moreover, both of the known mouse mutations that destroy gene function are found in this region.

Therapeutic Applications

Antagonists of the DL and dl protein could be generated (for the purpose of reducing hair growth) by producing C-terminally truncated proteins. Based upon mutation analysis, it is believed that deletion of residues 358–448 in DL or residues 332–448 in dl, generate dominant negative phenotypes, such that these proteins could bind wild-type receptors and/or ligands, but not activate downstream components of the signaling pathway. Therefore, it is anticipated that such peptides expressed or applied therapeutically would abrogate signaling in vivo. Alternatively, it is believed that secreted forms of the dl or DL extracellular domain (1–183) could compete for available EDA1-II/Ta, and thus generate an apparent loss of signaling through DL or dl.

To reduce hair growth, a truncated portion of the DL or dl protein would be produced, including only the extracellular domain 1–183 and variants thereof, and delivered to the tail and bellies of mice using the methods described above in connection with the delivery of the DL or dl protein. Hair growth would be monitored following the therapies.

Antibodies raised against the extracellular portion of the DL or dl protein (residues 1–183) may be functional as agonists of DL or dl. These molecules, or any others that cause multimerization (such as dimerization or trimerization) of the DL or dl proteins, are likely to cause activation of the downstream pathway. Similarly, overexpression of the DL or dl proteins can compensate for the absence of the likely ligand, EDA/Ta, presumably by causing spontaneous multimerization (e.g. trimerization) through crowding of receptors.

Screening of potential agonists and antagonists is facilitated by the knowledge that such ligands can interact at the DL or dl receptor. A labeled ligand or receptor (such as a radioactively labeled ligand or receptor) can be used to probe compounds or peptides arranged in an array on a substrate. The array can be used as a probe to determine which of the compounds or peptides hybridize to the labeled ligand or receptor. Such hybridized compounds or peptides can then be tested in the mouse model for biological function.

EXAMPLE 4

Variant DNA Molecules

Having presented the nucleotide sequences of the human EDA1-II, murine dl and human DL cDNAs, and the amino acid sequences of the EDA1-II, dl and DL encoded proteins, this invention now also facilitates the creation of DNA molecules, and thereby proteins, which are derived from those disclosed but which vary in their precise nucleotide or amino acid sequence from those disclosed. Such variants may be obtained through a combination of standard molecular biology laboratory techniques and the nucleotide sequence information disclosed by this invention. Particular guidance about the structure of the proteins, and proposed variants that retain biological activity, have already been provided. In addition, specific mutations that abolish biological activity of the ligand and receptor in humans and mice have also been given to provide additional evidence of mutations that should be avoided when making variant peptides that retain biological activity. This example provides some additional general teaching about techniques for preparing variant DNA sequences that encode these and other peptide sequences.

Variant DNA molecules include those created by standard DNA mutagenesis techniques, for example, M13 primer mutagenesis. Details of these techniques are provided in Sambrook et al. (1989), Ch. 15. By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the biological activity of the EDA1-II protein are comprehended by this invention.

In conjunction with randomized site-directed mutagenesis, one skilled in the art could use either simple predictive algorithms (Chou and Fasman 1974; Garnier et al. 1978) or computer software (for example MOLSCRIPT, Kraulis 1991; in addition see http://hera.lmb.uni-muenchen.de/groups/gbm-pd/int-soft.html or http://www.public.iastate.edu/~pedro/research_tools.html for software and email server links) to predict the peptide secondary structure of wild-type and mutated synthetic peptides. Mutated peptides that maintain the same predicted secondary structure as the wild-type peptide can be tested for their ability to promote hair growth.

DNA molecules and nucleotide sequences which are derived from the disclosed DNA molecules as described above may also be defined as DNA sequences which hybridize under stringent conditions to the DNA sequences disclosed, or fragments thereof. Hybridization conditions resulting in particular degrees of stringency will vary depending upon the nature of the hybridization method of choice and the composition and length of the hybridizing DNA used. Generally, the temperature of hybridization and the ionic strength (especially the Na$^+$ concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference. By way of illustration only, a hybridization experiment may be performed by hybridization of a DNA molecule (for example, a variant of the EDA1-II cDNA) to a target DNA molecule (for example, the EDA1-II cDNA) which has been electrophoresed in an agarose gel and transferred to a nitrocellulose membrane by Southern blotting (Southern, 1975), a technique well known in the art and described in Sambrook et al. (1989).

Hybridization with a target probe labeled, for example, with [$^{32}$P]-dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to 10$^9$ CPM/$\mu$g or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, 1962):

$$T_m = 81.5\ C. - 16.6(\log_{10}[Na^+]) + 0.41(\%G+C) - 0.63(\%\ formamide) - (600/l)$$

Where l=the length of the hybrid in base pairs.

This equation is valid for concentrations of Na$^+$ in the range of 0.01 M to 0.4 M, and it is less accurate for calculations of $T_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989).

Thus, by way of example, for a 150 base pair DNA probe with a hypothetical GC content of 45%, and assuming that the filter will be washed in 0.3×SSC solution following hybridization, a calculation of hybridization conditions required to give particular stringencies may be made as follows:

[Na$^+$]=0.045M

%GC=45%

Formamide concentration=0 l=150 base pairs $T_m = 81.5 - 16(\log_{10}[Na^+]) + (0.41 \times 45) - (600/150)$ and so $T_m = 74.4$ C.

The $T_m$ of double-stranded DNA decreases by 1–1.5° C. with every 1% decrease in homology (Bonner et al., 1973). Therefore, for this given example, washing the filter in 0.3×SSC at 59.4–64.4° C. will produce a stringency of hybridization equivalent to 90%; that is, DNA molecules with more than 10% sequence variation relative to the target CDNA will not hybridize. Alternatively, washing the hybridized filter in 0.3×SSC at a temperature of 65.4–68.4° C. will yield a hybridization stringency of 94%; that is, DNA molecules with more than 6% sequence variation relative to the target cDNA molecule will not hybridize. The above example is given entirely by way of theoretical illustration. One skilled in the art will appreciate that other hybridization techniques may be utilized and that variations in experimental conditions will necessitate alternative calculations for stringency.

For purposes of the present invention, "stringent conditions" encompass conditions under which hybridization will only occur if there is less than 25% mismatch between the hybridization probe and the target sequence. "Stringent conditions" may be broken down into particular levels of stringency for more precise definition. Thus, as used herein, "moderate stringency" conditions are those under which DNA molecules with more than 25% sequence variation (also termed "mismatch") will not hybridize; conditions of "medium stringency" are those under which DNA molecules with more than 15% mismatch will not hybridize, and conditions of "high stringency" are those under which DNA sequences with more than 10% mismatch will not hybridize. Conditions of "very high stringency" are those under which DNA sequences with more than 4 or 5% mismatch will not hybridize.

The degeneracy of the genetic code further widens the scope of the present invention as it enables major variations in the nucleotide sequence of a DNA molecule while maintaining the amino acid sequence of the encoded protein. For example, the second amino acid residue of the DL protein is alanine. This is encoded in the DL cDNA by the nucleotide codon triplet GCC. Because of the degeneracy of the genetic code, three other nucleotide codon triplets, GCG, GCT and GCA, also code for alanine. Thus, the nucleotide sequence of the DL cDNA could be changed at this position to any of these three codons without affecting the amino acid composition of the encoded protein or the characteristics of the protein. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein also comprehended by this invention.

One skilled in the art will recognize that the DNA mutagenesis techniques described above may be used not only to produce variant DNA molecules, but will also facilitate the production of proteins which differ in certain structural aspects from the EDA1-II, dl and DL proteins, yet which proteins are clearly derivative of these proteins and which maintain the essential functional characteristic of the protein as defined above. Newly derived proteins may also be selected in order to obtain variations on the characteristic of the protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for optimal activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure.

Substitutional variants are those in which at least one residue in the amino acid sequence has been removed and a different residue inserted in its place. Such substitutions generally are conservative when it is desired to finely modulate the characteristics of the protein. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Substantial changes in function or immunological identity are made by selecting substitutions that are less conservative than those listed above, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the EDA1-II, dl or DL protein by transient expression of the protein in question in cells.

An in vitro screening system can also be devised, by using the dl or DL cDNA to express the receptor on a cell surface. A promoter can be selected that switches on a marker gene (such as an antibiotic resistance gene), in which the promoter is directly controlled by dl or DL signaling. When pools of compounds are added to the cells in culture, it can be determined which of the compounds activate the receptor, and therefore allow the cells to grow in the presence of an antibiotic that would otherwise kill the cell. A similar strategy can be used to screen for antagonists, which will switch off expression of a gene that usually activated in the presence of the promoter.

EXAMPLE 5

Expression of Proteins

With the provision of the human EDA1-II, murine dl, and human DL cDNAs and amino acid sequences, the expression and purification of the corresponding proteins by standard laboratory techniques is now enabled. The purified protein may be used for functional analyses, antibody production and patient therapy. Furthermore, the DNA sequence of the EDA1-II cDNA and the mutant EDA1-II cDNAs isolated from patients, as well as the dl and DL cDNA and mutant dl and DL cDNAs, can be manipulated in studies to understand the expression of the gene and the function of its product. In this way, the underlying biochemical defect which results in the symptoms of HED can be established. The mutant versions of the cDNAs isolated to date, and others which may be isolated based upon information contained herein, may be studied in order to detect other alterations in expression patterns in terms of relative quantities, tissue specificity and functional properties of the encoded mutant protein.

Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in E. coli in large amounts for functional studies. Methods and plasmid vectors for producing fusion proteins and intact native proteins in bacteria are described in Sambrook et al. (1989) (ch. 17, herein incorporated by reference). Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (1989) and are well known in the art. Often, proteins expressed at high levels are found in insoluble inclusion bodies. Methods for extracting proteins from these aggregates are described by Sambrook et al. (1989) (ch. 17).

Vector systems suitable for the expression of lacZ fusion genes include the pUR series of vectors (Ruther and Muller-Hill, 1983), pEX1-3 (Stanley and Luzio, 1984) and pMR100 (Gray et al., 1982). Vectors suitable for the production of intact native proteins include pKC30 (Shimatake and Rosenberg, 1981), pKK177-3 (Amann and Brosius, 1985) and pET-3 (Studiar and Moffatt, 1986). EDA1-II, dl and DL fusion proteins may be isolated from protein gels, lyophilized, ground into a powder and used as an antigen. The DNA sequence can also be transferred to other cloning vehicles, such as other plasmids, bacteriophages, cosmids, animal viruses and yeast artificial chromosomes (YACs) (Burke et al., 1987). These vectors may then be introduced into a variety of hosts including somatic cells, and simple or complex organisms, such as bacteria, fungi (Timberlake and Marshall, 1989), invertebrates, plants (Gasser and Fraley, 1989), and mammals (Pursel et al., 1989), which cell or organisms are rendered transgenic by the introduction of the heterologous EDA1-II, dl, or DL cDNA.

For expression in mammalian cells, the cDNA sequence may be ligated to heterologous promoters, such as the simian virus (SV40), promoter in the pSV2 vector (Mulligan and Berg, 1981), and introduced into cells, such as monkey COS-1 cells (Gluzman, 1981), to achieve transient or long-term expression. The stable integration of the chimeric gene construct may be maintained in mammalian cells by biochemical selection, such as neomycin (Southern and Berg, 1982) and mycophoenolic acid (Mulligan and Berg, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with or without an intron and a promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of SV40 or long terminal repeat (LTR) of Rous Sarcoma virus and polyadenylation and splicing signal from SV40 are readily available (Mulligan et al., 1981; Gorman et al., 1982). The level of expression of the cDNA can be manipulated with this type of vector, either by using promoters that have different activities (for example, the baculovirus pAC373 can express cDNAs at high levels in S. frugiperda cells (Summers and Smith, 1985) or by using vectors that contain promoters amenable to modulation, for example, the glucocorticoid-responsive promoter from the mouse mammary tumor virus (Lee et al., 1982). The expression of the cDNA can be monitored in the recipient cells 24 to 72 hours after introduction (transient expression).

In addition, some vectors contain selectable markers such as the gpt (Mulligan and Berg, 1981) or neo (Southern and Berg, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., 1981) or Epstein-Barr (Sugden et al., 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, 1973) or strontium phosphate (Brash et al., 1987), electroporation (Neumann et al., 1982), lipofection (Felgner et al., 1987), DEAE dextran (McCuthan et al., 1968), microinjection (Mueller et al., 1978), protoplast fusion (Schafner, 1980), or pellet guns (Klein et al., 1987). Alternatively, the cDNA can be introduced by infection with virus vectors. Systems are developed that use, for example, retroviruses (Bernstein et al., 1985), adenoviruses (Ahmad et al., 1986), or Herpes virus (Spaete et al., 1982).

These eukaryotic expression systems can be used for studies of the EDA1-II, dl and DL genes, and mutant forms of these genes, the encoded protein and mutant forms of this protein. Such uses include, for example, the identification of regulatory elements located in the 5' region of the EDA1-II gene on genomic clones that can be isolated from human genomic DNA libraries using the information contained in the present invention. The eukaryotic expression systems may also be used to study the function of the normal complete protein, specific portions of the protein, or of naturally occurring or artificially produced mutant proteins. Naturally occurring mutant proteins exist in patients with EDA1-II, while artificially produced mutant proteins can be designed by site directed mutagenesis as described above. These latter studies may probe the function of any desired amino acid residue in the protein by mutating the nucleotide coding for that amino acid.

Using the above techniques, the expression vectors containing the EDA1-II, dl or DL gene, or cDNA sequence or fragments or variants or mutants thereof, can be introduced into human cells, mammalian cells from other species or non-mammalian cells as desired. The choice of cell is determined by the purpose of the treatment. For example, monkey COS cells (Gluzman, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

Expression of the protein in eukaryotic cells may be used as a source of proteins to raise antibodies. The protein may be extracted following release of the protein into the supernatant as described above, or, the cDNA sequence may be incorporated into a eukaryotic expression vector and expressed as a chimeric protein with, for example, β-globin or glutathione S-transferase (GST). Antibody to β-globin is thereafter used to purify the chimeric protein. Corresponding protease cleavage sites engineered between the β-globin gene and the cDNA are then used to separate the two polypeptide fragments from one another after translation. One useful expression vector for generating β-globin chimeric proteins is pSG5 (Stratagene). This vector encodes rabbit β-globin.

The recombinant cloning vector, according to this invention, then comprises the selected DNA of the DNA sequences of this invention for expression in a suitable host. The DNA is operatively linked in the vector to an expression control sequence in the recombinant DNA molecule so that the polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this invention, may be selected from the group consisting of bacteria; yeast; fungi; plant; insect; mouse or other animal; or human tissue cells.

It is appreciated that for mutant or variant DNA sequences, similar systems can be employed to express and produce the mutant or variant product.

EXAMPLE 6
Production and Use of Antibodies
Production of Antibodies

Monoclonal or polyclonal antibodies may be produced to either the normal EDA1-II, dl or DL protein, or mutant forms of these proteins. Optimally, antibodies raised against the protein will specifically detect the protein. That is, antibodies raised against the protein (e.g. EDA1-II) would recognize and bind the protein and would not substantially recognize or bind to other proteins found in human cells. The determination that an antibody specifically detects an EDA1-II, dl or DL protein is made by any one of a number of standard immunoassay methods; for instance, the Western blotting technique (Sambrook et al., 1989).

To determine that a given antibody preparation (such as one produced in a mouse against the EDA1-II protein) specifically detects the EDA1-II protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the protein will, by this technique, be shown to bind to the protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-EDA1-II protein binding.

Antibodies that specifically bind to an EDA1-II protein (or any of the other novel proteins disclosed herein) belong to a class of molecules that are referred to herein as "specific binding agents." Specific binding agents that are capable of specifically binding to an EDA1-II protein may include polyclonal antibodies, monoclonal antibodies (including humanized monoclonal antibodies) and fragments of monoclonal antibodies such as Fab, F(ab')2 and Fv fragments, as well as any other agent capable of specifically binding to an EDA1-II protein (or the other disclosed proteins).

Substantially pure protein suitable for use as an immunogen is isolated from the transfected or transformed cells as described above. Concentration of protein in the final preparation is adjusted, for example, by concentration on an Amicon filter device, to the level of a few micrograms per milliliter. Monoclonal or polyclonal antibody to the protein can then be prepared as follows.

Monoclonal antibody to epitopes of the EDA 1-II, dl or DL protein, identified and isolated as described, can be prepared from murine hybridomas according to the classical method of Kohler and Milstein (1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988). In addition, protocols for producing humanized forms of monoclonal antibodies (for therapeutic applications) and fragments of monoclonal antibodies are known in the art.

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher (1980).

A third approach to raising antibodies against the EDA1-II, dl or DL protein is to use synthetic peptides synthesized on a commercially available peptide synthesizer based upon the predicted amino acid sequence of the EDA1-II, dl or DL protein.

Antibodies may be raised against the EDA 1-II, dl or DL protein by subcutaneous injection of a DNA vector which expresses the EDA1-II, dl or DL protein into laboratory animals, such as mice. Delivery of the recombinant vector into the animals may be achieved using a hand-held form of the Biolistic system (Sanford et al., 1987) as described by Tang et al. (1992). Expression vectors suitable for this purpose may include those which express the EDA1-II, dl or DL cDNA under the transcriptional control of either the human actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample.

Therapeutic Uses For Antibodies

The antibodies described above can be used as either agonists or antagonists of the dl and DL receptors. Assays to determine whether an antibody functions as an agonist or antagonist of the dl or DL receptor are described in Examples 1–3. Antibodies which recognize the EDA1-II ligand, may prevent EDA1-II from binding to the DL receptor. Such antibodies would serve as antagonists of the DL receptor, which may therefore be used to reduce hair growth.

Alternatively, antibodies which recognize the dl or DL receptor may function as agonists of the receptor. These antibodies may cause a multimerization or crosslinking of the receptors, which in turn may activate the downstream pathway. Such antibodies may be used to stimulate the growth of hair, hair follicles, teeth and/or eccrine sweat glands.

EXAMPLE 7

Use of EDA1-II, dl and DL Nucleotide Sequences for Diagnosis

One major application of the EDA1-II cDNA, dl and DL cDNA sequence information presented herein is in the area of genetic testing, carrier detection and prenatal diagnosis for HED, in both its autosomal and X-linked forms. Individuals carrying mutations in the EDA1-II, dl or DL gene (disease carrier or patients) may be detected at the DNA level with the use of a variety of techniques. For such a diagnostic procedure, a biological sample of the subject, containing either DNA or RNA derived from the subject, is assayed for the presence of a mutant gene. Suitable biological samples include samples containing genomic DNA or RNA obtained from body cells, such as those present in peripheral blood, urine, saliva, tissue biopsy, surgical specimen, amniocentesis samples and autopsy material. The detection of mutations in the EDA1-II, dl or DL gene may be detected using a SSCP analysis as described above in Examples 1–3. The detection in the biological sample of either a mutant EDA1-II, dl or DL gene or a mutant EDA1-II, dl or DL RNA may also be performed by a number of other methodologies known in the art, as outlined below.

One suitable detection technique is the polymerase chain reaction amplification of reverse transcribed RNA (RT-PCR) of RNA isolated from lymphocytes followed by direct DNA sequence determination of the products. The presence of one or more nucleotide difference between the obtained sequence and the EDA1-II, dl or DL cDNA sequence presented herein, and especially, differences in the ORF portion of the nucleotide sequence, are taken as indicative of a potential EDA1-II, dl or DL gene mutation. The phenotypes of persons in whom the mutation is detected may be noted, and the same mutations in other samples considered to predict a similar phenotype. If the cells (or the subject from whom the sample is taken) are normal, then the observed nucleotide differences are regarded as "neutral," and the subject is not classified as a carrier or sufferer on the basis of this nucleotide difference. On the other hand, if the altered cDNA reveals an abnormal result in the assay, the nucleotide difference is regarded as a mutation rather than a natural difference, the protein is an aberrant (or mutant) EDA1-II, dl or DL gene product, and the subject is classified as a sufferer or carrier.

Because of the diploid nature of the human genome, both copies of the EDA1-II gene may need to be examined to distinguish between carriers and sufferers. In females, if a single copy of the EDA1-II gene is found to be mutated and the other copy is "normal," then the subject is classified as an XLHED carrier or heterozygote. In females, if both copies of the EDA1-II gene are found to be mutated, then the subject is classified as a sufferer. In cases of males, only a single copy of the EDA1 gene exists, hence if it is mutated, the individual is a sufferer.

Alternatively, DNA extracted from lymphocytes or other cells may be used directly for amplification. The direct amplification from genomic DNA would be appropriate for analysis of the entire EDA1-II gene including regulatory sequences located upstream and downstream from the open reading frame. Reviews of direct DNA diagnosis have been presented by Caskey (1989) and by Landegren et al. (1989).

Further studies of EDA1-II genes isolated from XLHED patients may reveal particular mutations which occur at a high frequency within this population of individuals. In this case, rather than sequencing the entire EDA1-II gene, it may be possible to design DNA diagnostic methods to specifically detect the most common mutations.

The detection of specific DNA mutations may be achieved by methods such as hybridization using specific oligonucleotides (Wallace et al., 1986), direct DNA sequencing (Church and Gilbert, 1988), the use of restriction enzymes (Flavell et al., 1978; Geever et al., 1981), discrimination on the basis of electrophoretic mobility in gels with denaturing reagent (Myers and Maniatis, 1986), RNase protection (Myers et al., 1985), chemical cleavage (Cotton et al., 1993), and the ligase-mediated detection procedure (Landegren et al., 1988).

By way of example, oligonucleotides specific to normal or mutant sequences may be chemically synthesized using commercially available machines, labeled radioactively with isotopes (such as $^{32}$P) or non-radioactively (with tags such as biotin (Ward and Langer et al., 1981), and hybridized to individual DNA samples immobilized on membranes or other solid supports by dot-blot or transfer from gels after electrophoresis. The presence or absence of these specific sequences may then visualized by methods such as autoradiography or fluorometric (Landegren, et al., 1989) or colorimetric reactions (Gebeyehu et al., 1987).

Sequence differences between normal and mutant forms of that gene may also be revealed by the direct DNA sequencing method of Church and Gilbert (1988). Cloned DNA segments may be used as probes to detect specific DNA segments. The sensitivity of this method is greatly enhanced when combined with PCR (Wrichnik et al., 1987; Wong et al., 1987; Stoflet et al., 1988). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags.

Sequence alterations may occasionally generate fortuitous restriction enzyme recognition sites or may eliminate existing restriction sites. Changes in restriction sites are revealed by the use of appropriate enzyme digestion followed by conventional gel-blot hybridization (Southern, 1975). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence differences may be achieved by detection of alteration in electrophoretic mobility of DNA fragments in gels with or without denaturing reagent. Small sequence deletions and insertions can be visualized by high-resolution gel electrophoresis. For example, a PCR product with small deletions is clearly distinguishable from a normal sequence on an 8% non-denaturing polyacrylamide gel (Nagamine et al., 1989). DNA fragments of different sequence compositions may be distinguished on denaturing formamide gradient gels in which the mobilities of different DNA fragments are retarded in the gel at different positions according to their specific "partial-melting" temperatures (Myers et al., 1985). Alternatively, a method of detecting a mutation comprising a single base substitution or other small change could be based on differential primer length in a PCR. For example, an invariant primer could be used in addition to a primer specific for a mutation. The PCR products of the normal and mutant genes can then be differentially detected in acrylamide gels.

In addition to conventional gel-electrophoresis and blot-hybridization methods, DNA fragments may also be visualized by methods where the individual DNA samples are not immobilized on membranes. The probe and target sequences may be both in solution, or the probe sequence may be immobilized (Saiki et al., 1989). A variety of detection methods, such as autoradiography involving radioisotopes, direct detection of radioactive decay (in the presence or absence of scintillant), spectrophotometry involving calorigenic reactions and fluorometry involved fluorogenic reactions, may be used to identify specific individual genotypes.

If more than one mutation is frequently encountered in the gene, a system capable of detecting such multiple mutations would be desirable. For example, a PCR with multiple, specific oligonucleotide primers and hybridization probes may be used to identify all possible mutations at the same time (Chamberlain et al., 1988). The procedure may involve immobilized sequence-specific oligonucleotides probes (Saiki et al., 1989). One method that is expected to be particularly suitable for detecting mutations in the genes of the present invention is the use of high density oligonucleotide arrays (also known as "DNA chips") as described by Hacia et al. (1996).

EXAMPLE 8

Quantitation of EDA1-II, dl or DL Protein

An alternative method of diagnosing sufferers or carrier status may be to quantitate the level of EDA1-II, dl or DL protein in the cells of an individual in which expression of the protein is expected to occur. This diagnostic tool would be useful for detecting reduced levels of the EDA1-II, dl or DL protein which result from, for example, mutations in the promoter regions of the EDA1-II, dl or DL gene, or mutations within the coding region of the gene which produced truncated, non-functional polypeptides. The determination of reduced EDA1-II, dl or DL protein levels would be an alternative or supplemental approach to the direct determination of status by nucleotide sequence determination outlined above. The availability of antibodies specific to the EDA1-II, dl or DL protein would allow the quantitation of cellular EDA1-II, dl or DL protein by one of a number of immunoassay methods which are well known in the art and are presented in Harlow and Lane (1988). Such assays permit both the detection of EDA1-II, dl and DL protein in a biological sample and the quantitation of such protein. Typical methods involve combining the biological sample with an EDA1-II, dl or DL specific binding agent, such as an anti-EDA1-II, dl or DL protein antibody, so that complexes form between the binding agent and the EDA1-II, dl or DL protein present in the sample, and then detecting or quantitating such complexes.

In particular forms, these assays may be performed with the EDA1-II, dl or DL specific binding agent immobilized on a support surface, such as in the wells of a microtiter plate or on a column. The biological sample is then introduced onto the support surface and allowed to interact with the specific binding agent so as to form complexes. Excess biological sample is then removed by washing, and the complexes are detected with a reagent, such as a second anti-EDA1-II, dl or DL protein antibody that is conjugated with a detectable marker.

For the purposes of quantitating the EDA1-II, dl or DL protein, a biological sample of the subject, which sample includes cellular proteins, is required. Such a biological sample may be obtained from body cells, such as those present in which expression of the protein has been detected. As described in Example 1, for example, Northern analysis could be used to analyze EDA1-II expression in the heart, pancreas, prostate, testis or uterus, but its expression in the skin is clearly the most accessible and convenient source from which specimens can be obtained. Specimens can be obtained from amniocentesis samples, surgical specimens and autopsy material. Quantitation of EDA1-II protein would be made by immunoassay and compared to levels of the protein found in non-XLHED human cells. A significant (preferably 50% or greater) reduction in the amount of EDA1-II protein in the cells of a subject compared to the amount of EDA1-II protein found in non-XLHED human cells would be taken as an indication that the subject may be an XLHED sufferer or carrier. Correspondingly, a significant (preferably 50% or greater) reduction in the amount of dl or DL protein in the cells of a subject compared to the amount of dl or DL protein found in non-autosomal HED human cells would be taken as an indication that the subject may be an autosomal HED sufferer or carrier.

EXAMPLE 9
Peptide Modifications

The present invention includes biologically active molecules that mimic the action (mimetics) of the EDA1-II, dl and DL proteins of the present invention. The invention therefore includes synthetic embodiments of naturally-occurring peptides described herein, as well as mimetics (non-peptide organic molecules), derivatives (chemically functionalized peptide molecules obtained starting with the disclosed peptide sequences) and variants (homologs) of these peptides that specifically inhibit the conversion assay reaction. Each peptide ligand of the invention is comprised of a sequence of amino acids, which may be either L- and/or D- amino acids, naturally occurring and otherwise.

Peptides may be modified by a variety of chemical techniques to produce derivatives having essentially the same activity as the unmodified peptides, and optionally having other desirable properties. For example, carboxylic acid groups of the peptide, whether carboxyl-terminal or side chain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_6$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide.

Hydroxyl groups of the peptide side chain may be converted to $C_1$–$C_{16}$ alkoxy or to a $C_1$–$C_{16}$ ester using well-recognized techniques. Phenyl and phenolic rings of the peptide side chain may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the peptide side chains can be extended to homologous $C_2$–$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

In order to maintain an optimally functional peptide, particular peptide variants will differ by only a small number of amino acids from the peptides disclosed in this specification. Such variants may have deletions (for example of 1–3 or more amino acid residues), insertions (for example of 1–3 or more residues), or substitutions that do not interfere with the desired activity of the peptides. Substitutional variants are those in which at least one residue in the amino acid sequence has been removed and a different residue inserted in its place. In particular embodiments, such variants will have amino acid substitutions of single residues, for example 1, 3, 5 or even 10 substitutions in the full length EDA1-II, dl or DL protein.

Peptidomimetic and organomnimetic embodiments are also within the scope of the present invention, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides of this invention having substantial specific hair growth promoting and/or blocking activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165–174 and *Principles of Pharmacology* (ed. Munson, 1995), chapter 102 for a description of techniques used in CADD. Also included within the scope of the invention are mimetics prepared using such techniques that produce either peptides or conventional organic pharmaceuticals that retain the biological activity of the ligand or receptor.

EXAMPLE 10
Peptide Synthesis and Purification

The peptides provided by the present invention can be chemically synthesized by any of a number of manual or automated methods of synthesis known in the art. For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/ hydroxybenzotriazole or 2-(1H-benzo-triazol-1-yl)-1,1,3,3-tetramethyluronium hexafluorophosphate/ hydroxybenzotriazole (HBTU/HOBT), and using p-hydroxymethylphenoxymethylpolystyrene (HMP) or Sasrin resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. (1989).

Sasrin resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5–3 hours at room temperature.

Crude peptides are purified by preparative high pressure liquid chromatography (HPLC), for example using a Waters Delta-Pak C18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

EXAMPLE 11
Pharmaceutical Compositions

The invention provides homogeneous compositions of the inhibitory peptides, for example a composition that is comprised of at least 90% of the peptide, variant, analog, derivative or mimetic in the composition. Such compositions are useful as therapeutic agents when constituted as pharmaceutical compositions with the appropriate carriers or diluents. A particular mode of administration would be direct topical application, or intradermal injection.

Any of the common pharmaceutical carriers, such as sterile saline solution or sesame oil, can be used. The medium may also contain conventional pharmaceutical adjunct materials such as, for example, pharmaceutically acceptable salts to adjust the osmotic pressure, buffers, preservatives and the like. Among the preferred media are normal saline and sesame oil.

Embodiments of the invention comprising medicaments can be prepared with conventional pharmaceutically acceptable carriers, adjuvants and counterions as would be known to those of skill in the art.

EXAMPLE 12
Gene Therapy

In some embodiments, the present invention relates to a method of promoting the development of hair and sweat glands in persons suffering from HED by introducing a gene coding for EDA1-II, dl or DL into the person. A general strategy for transferring genes into donor cells is disclosed in U.S. Pat. No. 5,529,774, which is incorporated by reference. Generally, a gene encoding a protein having therapeutically desired effects is cloned into a viral expression vector, and that vector is then introduced into the target organism. The virus infects the cells, and produces the protein sequence in vivo, where it has its desired therapeutic effect. See, for example, Zabner et al. (1993).

In some of the foregoing examples, it may only be necessary to introduce the genetic or protein elements into certain cells or tissues. For example, in the case of HED, introducing them into only the skin may be sufficient. However, in some instances, it may be more therapeutically effective and simple to treat all of the patients cells, or more broadly disseminate the vector, for example by intravascular administration.

The nucleic acid sequence encoding the therapeutic agent (s) can be placed under the control of a suitable promoter. Suitable promoters which may be employed include, but are not limited to, the gene's native promoter; retroviral LTR promoter; adenoviral promoters, such as the adenoviral major late promoter; the cytomegalovirus (CMV) promoter; the Rous Sarcoma Virus (RSV) promoter; inducible promoters, such as the MMTV promoter; the metallothionein promoter; heat shock promoters; the albumin promoter; the histone promoter; the β-actin promoter; TK promoters; B19 parvovirus promoters; and the ApoAI promoter. However the scope of the present invention is not limited to specific foreign genes or promoters.

The recombinant nucleic acid can be administered to the animal host by any method which allows the recombinant nucleic acid to reach the appropriate cells. These methods include injection, infusion, deposition, implantation, or topical administration. Injections can be intradermal or subcutaneous. The recombinant nucleic acid can be delivered as part of a viral vector, such as avipox viruses, recombinant vacciniavirus, replication-deficient adenovirus strains or poliovirus, or as a non-infectious form such as naked DNA or liposome encapsulated DNA.

EXAMPLE 13
Viral Vectors for Gene Therapy

Adenoviral vectors may include essentially the complete adenoviral genome (Shenk et al., 1984). Alternatively, the adenoviral vector may be a modified adenoviral vector in which at least a portion of the adenoviral genome has been deleted. In one embodiment, the vector includes an adenoviral 5' ITR; an adenoviral 3' ITR; an adenoviral encapsidation signal; a DNA sequence encoding a therapeutic agent such as EDA1-II, dl or DL; and a promoter for expressing the DNA sequence encoding a therapeutic agent. The vector is free of at least the majority of adenoviral E1 and E3 DNA sequences, but is not necessarily free of all of the E2 and E4 DNA sequences, and DNA sequences encoding adenoviral proteins transcribed by the adenoviral major late promoter.

Such a vector may be constructed according to standard techniques, using a shuttle plasmid which contains, beginning at the 5' end, an adenoviral 5' ITR, an adenoviral encapsidation signal, and an E1a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. The DNA segment serves as a substrate for homologous recombination with a modified or mutated adenovirus, and may encompass, for example, a segment of the adenovirus 5' genome no longer than from base 3329 to base 6246. The plasmid may also include a selectable marker and an origin of replication. The origin of replication may be a bacterial origin of replication. A desired DNA sequence encoding a therapeutic agent may be inserted into the multiple cloning site of the plasmid.

The plasmid may be used to produce an adenoviral vector by homologous recombination with a modified or mutated adenovirus in which at least the majority of the E1 and E3 adenoviral DNA sequences have been deleted. Homologous recombination may be effected through co-transfection of the plasmid vector and the modified adenovirus into a helper cell line, such as 293 cells, by $CaPO_4$ precipitation. The homologous recombination produces a recombinant adenoviral vector which includes DNA sequences derived from the shuttle plasmid between the Not I site and the homologous recombination fragment, and DNA derived from the E1 and E3 deleted adenovirus between the homologous recombination fragment and the 3' ITR.

In one embodiment, the adenovirus may be constructed by using a yeast artificial chromosome (or YAC) containing an adenoviral genome according to the method described in Ketner et al. (1994), in conjunction with the teachings contained herein. In this embodiment, the adenovirus yeast artificial chromosome is produced by homologous recombination in vivo between adenoviral DNA and yeast artificial chromosome plasmid vectors carrying segments of the adenoviral left and right genomic termini. A DNA sequence encoding a therapeutic agent then may be cloned into the adenoviral DNA. The modified adenoviral genome then is excised from the adenovirus yeast artificial chromosome in order to be used to generate adenoviral vector particles as hereinabove described.

The adenoviral particles are administered in an amount effective to produce a therapeutic effect in a host. The exact dosage of adenoviral particles to be administered is dependent upon a variety of factors, including the age, weight, and sex of the patient to be treated, and the nature and extent of the disease or disorder to be treated. The adenoviral particles may be administered as part of a preparation having a titer of adenoviral particles of at least $1 \times 10^{10}$ pfu/ml, and in general not exceeding $2 \times 10^{11}$ pfu/ml. The adenoviral particles may be administered in combination with a pharmaceutically acceptable carrier in a volume up to 10 ml. The pharmaceutically acceptable carrier may be, for example, a liquid carrier such as a saline solution, protamine sulfate (Elkins-Sinn, Inc., Cherry Hill, N.J.), or Polybrene (Sigma Chemical).

In another embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus. The vector is generally a replication defective retrovirus particle.

Retroviral vectors are useful as agents to effect retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

New genes may be incorporated into proviral backbones in several general ways. In the most straightforward constructions, the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter. Alternatively, two genes may be expressed from a single promoter by the use of an Internal Ribosome Entry Site.

EXAMPLE 14

Ligand-Receptor Binding

The EDA1-II ligand is also used to quantitatively assay DL receptor binding affinity. The Tabby ligand could be used for dl. Membranes from dl or DL transfected CHO cells (LC-7) are incubated with increasing concentrations of ($^{125}$I)-EDA1-II in a final volume of 0.2 mL binding buffer (50 mM Hepes, pH 7.4, 10 mM NaCl, 1 mM $MgCl_2$, 2.5 mM $CaCl_2$, 0.1% bovine serum albumin, 0.025% bacitracin) containing 1 mg wheat germ agglutinin-coated SA beads (Amersham). Iodinated peptide may be synthesized using the chloramine T method. Assays are then performed in 96-well plates (OptiPlate, Caberra Packard), and the mixtures incubated with shaking for 1 hour. Bound ligand-associated radioactivity is determined by scintillation proximity (see, for example, Nelson, 1987, *Anal. Biochem.* 165:287; Bosworth and Towers, 1989, *Nature* 341:167) using a TopCount microplate scintillation counter (Canberra packard). Concentrations of free ligand are calculated by subtracting the amount of specifically-bound ligand from the total amount of radioligand added.

A Scatchard analysis may be performed to determine whether the radiolabeled monoiodo-peptide displays saturable and displaceable binding to membranes of EDR-expressing transfected cells, by determining the $K_D$ (slope of Scatchard line=$-1/K_D$) and a $B_{max}$ (Scatchard line abscissa intercept) of membrane protein. $K_D$ may be determined as in Munson, Principles of Pharmacology (Chapman & Hall), 1995, Chapter 1. These experiments may be used to demonstrate that the novel ligand peptide EDA1-II binds saturably to DL with high affinity, to further confirm that this peptide is a naturally-occurring, endogenous ligand for this receptor. The iodinated peptide can also be used as a radioligand to detect and quantify DL receptor levels.

Variant EDA1-II peptides, with deletions, substitutions, or insertions can also be tested for high affinity binding to the DL receptor using the same assay, and determining the $K_D$ of the variant peptide. For example, a variant peptide having a $K_d$ less than about $10^{-6}$ M, for example $10^{-9}$ M, such as 2 nM or 20 nM, would be considered a peptide that is suitable for further investigation in biological assays of hair growth stimulation.

Many other variations of the invention are possible. For example, the invention could include peptides consisting only of the dl or DL intracellular signaling domain, which is believed to include the mouse and human amino acid residues 267–448 of Seq. I.D. NOS. 19 and 17 respectively.

The therapeutic peptides disclosed herein may also be used to contribute to skin regeneration upon wounding. Stimulation of growth in the hair follicles (dl and DL are expressed in the hair matrix, the proliferating cells of the follicle) may help to advance healing of the skin in cases of trauma or burns. Dev. Biol. 1988, 130:610–20. Outer root sheath cells of human hair follicle are able to regenerate a fully differentiated epidermis in vitro. Also, it has recently been reported that in the pig, at least, the sweat glands can re-epithelialize damaged skin, thus their stimulation may be therapeutic. J. Invest. Dermatol. 1998, 110:13–9.

The predicted furin cleavage site of EDA1-II is important because mutations in the site result in a loss of function phenotype. This region is presumably recognized and cleaved by the furin protease, and this event is required to make active EDA1-II. If excess peptide from this region, preferably in a recognizable, but non-hydrolysable form, were applied to the skin it could compete with the wild type EDA1-II, greatly reducing its processing efficiency and reducing signaling. See for example the fusing of protease recognition sites to proteins known to be protease inhibitors (see Biochem. J. 1997, 326:507–14). A similar technique could be adapted to the present invention by cloning the putative EDA1-II cleavage sequence (e.g. residues 145 to 165) into such a protein.

The collagenous domains of EDA1-II must pull it together to make a functional trimeric ligand with three receptor binding domains brought together. If this trimerization occurs after proteolytic release from the membrane, it should be possible to interfere with it by introducing C-terminally truncated EDA1-II, such as the amino acids 153 to 239.

Having illustrated and described the EDA1-II isoform, the murine dl and the human DL genes, their coding sequences, the proteins encoded by these genes, and modes of use of these biological molecules, it should be apparent to one skilled in the art that the invention can be modified in arrangement and detail without departing from such principles. We claim all modifications coming within the spirit and scope of the claims presented herein.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

REFERENCES

Acton et al., *J Biol Chem* 268:3530–3537 (1993).
Ahmad et al., *J. Virol.* 57:267 (1986).

Alt et al., *J. Biol. Chem.* 253:1357–70 (1978).
Altschul et al., *J. Mol. Biol.,* 215, 403–410 (1990).
Altschul et al., *Nature Genet.,* 6, 119–129 (1994).
Amann and Brosius, *Gene,* 40:183–90 (1985).
Arnold and Hodgson, *PCR Methods Appl* 1:39–42 (1991).
Arte et al., *J Dent Res* 75:1346–1352 (1996).
Atherton et al. (Eds.), *Solid Phase Peptide Synthesis,* IRL Press: Oxford (1989).
Ausubel et al. *Current Protocols in Molecular Biology,* Greene Publishing
Associates and Wiley-Intersciences (1987).
Bernstein et al., *Gen. Engr'g* 7:235 (1985).
Better & Horowitz, *Methods Enzymol* 178: 476–496 (1989).
Bolton and McCarthy, *Proc. Natl. Acad. Sci. USA* 48:1390 (1962).
Bonner et al., *J. Mol. Biol.* 81:123 (1973).
Brash et al., *Mol. Cell Biol.* 7:2013 (1987).
Brockdorff et al. *Genomics* 10:17–22 (1991).
Brodsky and Shah, *Faseb J* 9:1537–1546 (1995).
Burke et al., *Science* 236:806–12 (1987).
Caskey, *Science* 236:1223–1228 (1989).
Chamberlain et al., *Nucl. Acids Res.* 16:1141–1155 (1988).
Chou and Fasman, *Biochem.* 13:222–245 (1974).
Church and Gilbert, *Proc. Natl. Acad. Sci. USA* 81:1991–1995 (1988).
Clarke et al., *Arch Dis Child* 62:989–996 (1987).
Corpet et al., *Nucleic Acids Research* 16, 10881–10890 (1988).
Cotton et al., *Mutat Res.* 1993 285:125–44 (1993).
Crocker and Cattanach, Genet. Res. 34(3):231–238 (1979).
Engvall, *Methods Enzymol.* 70(A):419–39 (1980).
Ezer et al., *Hum Mol Genet* 6:1581–1587 (1997).
Felgner et al., *Proc. Natl. Acad. Sci. USA.* 84:7413–7 (1987).
Ferguson et al., *Hum Mol Genet* 6:1589–1594 (1997).
Ferguson et al., *J Med Genet* 35:112–115 (1998).
Fisher, *Manual of Clinical Immunology,* Chapter 42 (1980).
Flavell et al., *Cell* 15:25 (1978).
Garnier et al., *J. Mol. Biol.* 120:97–120, (1978).
Gasser and Fraley, *Science* 244:1293 (1989).
Gatalica et al., *Am J Hum Genet* 60:352–365 (1997).
Gebeyehu et al., *Nucleic Acids Res.* 15:4513–4534 (1987).
Geever et al., *Proc. Natl. Acad. Sci USA* 78:5081 (1981).
Gluzman, *Cell* 23:175–182 (1981).
Gorman et al., *Proc. Natl. Acad. Sci USA* 78:6777–6781 (1982).
Graham and vander Eb, *Virology* 52:466 (1973).
Gray et al., *Proc. Natl. Acad. Sci. USA* 79:6598–602 (1982).
Grompe, *Nature Genet.* 5:111–117 (1993).
Hacia et al., *Nature Genetics* 14(4): 441–447 (1996).
Harlow and Lane, *Antibodies, A Laboratory Manual,* Cold Spring Harbor Laboratory, New York (1988).
Higgins and Sharp, *Gene,* 73: 237–244 (1988).
Higgins and Sharp, *CABIOS* 5: 151–153 (1989).
Hoffman, R. M., *J Drug Target;* 5(2):67–74 (1998).
Huang, et al., *Computer Applications in the Biosciences* 8, 155–165 (1992).
Innis et al. (Eds), *PCR Protocols, A Guide to Methods and Applications,* Academic Press, Inc., San Diego, Calif. (1990).
Illel, B., *Crit Rev Ther Drug Carrier Syst;* 14(3):207–219 (1997).
Kendrew et al (Eds.), *The Encyclopedia of Molecular Biology,* Blackwell Science Ltd. (1994).
Kere et al., *Nature Genetics* 13:409–416 (1996).
Ketner et al., *Proc. Natl. Acad. Sci., USA,* 91:6186–6190 (1994).
Klein et al., *Nature* 327:70 (1987).
Kohler and Milstein, *Nature* 256:495 (1975).
Kraulis, *J. Appl. Crystallog.* 24:946–950 (1991).
Landegren et al., *Science* 241:1077 (1988).
Landegren et al., *Science* 242:229–237 (1989).
Laurer et al., *Phann Res* 12(2):179–186 (1995).
Lee et al. *Nature* 294:228 (1982).
Lewin, (Ed.) *Genes V,* Oxford University Press, (1994).
Li and Hoffman, *Nat Med* 1(7):705–706 (1995).
Lieb et al., *J Pharm Sci* 86(9):1022–1009 (1997).
Liu et al., *Hum Mol Genet* 5:107–114 (1996).
Majumder et al., *Mammalian Genome* 9:863–868 (1998).
McCuthan et al., *J. Natl Cancer Inst.* 41:351 (1968).
Meyers (Ed.), *Molecular Biology and Biotechnology: a Comprehensive Desk Reference,* VCH Publishers, Inc. (1995).
Mueller et al., *Cell* 15:579 (1978).
Mulligan et al., *Proc. Natl Acad. Sci. USA* 78:1078–2076 (1981).
Mulligan and Berg, *Proc. Natl. Acad. Sci. USA* 78:2072–2076 (1981).
Munoz et al., *Am J Hum Genet* 61 :94–100 (1997).
Munson (Ed.), *Principles of Pharmacology,* Chapter 102 (1995).
Myers et al., *Science* 230:1242 (1985).
Myers and Maniatis, *Cold Spring Harbor Symp. Quant. Biol.* 51:275–284 (1986).
Nagamine et al., *Am. J. Hum. Genet.* 45:337–339 (1989).
Needleman and Wunsch, *J. Mol. Biol.* 48: 443 (1970).
Neumann et al., *EMBO J* 1:841 (1982).
Ouchterlony et al., In: *Handbook of Experimental Immunology,* Wier, D. (Ed.) Chapter 19, Blackwell (1973).
Pearson et al., *Methods in Molecular Biology* 24, 307–331 (1994).
Pearson and Lipman, *Proc. Natl. Acad. Sci. USA* 85: 2444 (1988).
Peltonen et al., *DNA Cell Biol* 16:227–234 (1997).
Pursel et al., *Science* 244:1281–1288 (1989).
Rohrer et al., *Nature* 343:570–572 (1990).
Ruther and Muller-Hill, *EMBO J.* 2:1791–4 (1983).
Saiki et al., *Proc. Nat. Acad. Sci. USA* 86:6230–6234.
Sambrook et al., In *Molecular Cloning: A Laboratory Manual,* Cold Spring Harbor, New York (1989).
Sanford et al., *Particulate Sci. Technol.* 5:27–37 (1987).
Sarver et al., i Mol. Cell Biol. 1:486 (1981).
Schafner, *Proc. Natl. Acad. Sci. USA* 77:2163–2167 (1980).
Segre, et al., *Genomics* 28: 549–559 (1995).
Shawlott et al., *Mol. Biol. Med.* 6, 299–307 (1989).
Sheffield et al., *Genomics* 16:325–332 (1993).
Shenk et al., *Curr. Top. Microbiol. Inununol.* 111: 1–39 (1984).
Simatake and Rosenberg, *Nature* 292:128(1981).
Smith and Waterman, *Adv. Appl. Math.* 2: 482 (1981).
Soafer, *Dev. Biol.* 34, 289–296 (1973).
Southern, *J. Mol. Biol.* 98:503 (1975).
Southern and Berg, *J. Mol. Appl. Genet.* 1:327–341 (1982).
Spaete et al., *Cell* 30:295 (1982).
Srivastava et al., *American Journal of Human Genetics* 58:126–132 (1996).
Srivastava et al., *Proc Natl Acad Sci USA* 94:13069–13074 (1997).
Stanley and Luzio, *EMBO J.* 3:1429–34 (1984).
Stoflet et al., *Science* 239:491–494 (1988).
Studiar and Moffatt, *J. Mol. Biol.* 189:113 (1986).
Sugden et al., *Mol Cell. Biol.* 5:410–3 (1985).
Summers and Smith, In: *Genetically Altered Viruses and the Environment,* Fields et al. (Eds.) 22:319–328, Cold Spring Harbor Laboratory Press, Cold Spring Harbor, N.Y. (1985).

Tang et al., *Nature* (London) 356:152–154 (1992).
Tijssen, In: *Laboratory Techniques in Biochemistry and Molecular Biology— Hybridization with Nucleic Acid Probes Part I*, Chapter 2, Elsevier, N.Y. (1993).
Timberlake and Marshall, *Science* 244:1313–1317 (1989).
Vaitukaitis et al., *J. Clin. Endocrinol. Metab.* 33:988–991 (1971).
Wallace et al., *Cold Spring Harbor Symp. Quant. Biol.* 51:257–261 (1986).
Walters, "Computer-Assisted Modeling of Drugs," in: Klegerman & Groves (Eds.) *Pharmaceutical Biotechnology*, Interpharm Press: Buffalo Grove, Ill., 165–174 (1993).
Ward and Langer, *Proc. Natl. Acad. Sci. USA* 78:6633–6657 (1981).
Wong et al., *Nature* 330:384–386 (1987).
Wrichnik et al., *Nucleic Acids Res.* 15:529–542 (1987).
Zabner et al., *Cell* 75:207–216 (1993).
Zonana, *Semin Dernatol* 12:241–246 (1993).
Zonana et al., *Am J Hum Genet* 43:75–85 (1988).
Zonana et al., *Am J Hum Genet* 51:1036–1046 (1992).
Zonana et al., *J Pediatr* 114:392–399 (1989).

We claim:

1. A purified protein that promotes the development of hair follicles, comprising an amino acid sequence selected from the group consisting of:
   (a) the amino acid sequence shown in SEQ ID NO 2;
   (b) the amino acid sequence shown in SEQ ID NOS 19 and 17;
   (c) amino acid residues 239–391 of SEQ ID NO 2;
   (d) amino acid residues 25–151 of SEQ ID NO 17;
   (e) amino acid sequences that differ from those specified in (b) by one or more conservative amino acid substitutions;
   (f) amino acid sequences having at least 80% sequence identity to the sequences specified in (b), (e), or (d);
   (g) amino acid sequences having at least 95% sequence identity to the sequences specified in (a) or (c);and
   (h) amino acid sequences having at least 98% sequence identity to the sequences specified in (a) or (c).

2. A purified protein that promotes the development of hair follicles, wherein the protein comprises the amino acid sequence shown in SEQ ID NO: 2, or amino acid residues 153–391 thereof.

3. A purified protein that promotes the development of hair follicles, wherein the protein comprises the amino acid sequence shown in SEQ ID NO: 17, and acts as a receptor for the protein of claim 2.

4. A purified protein that promotes the development of hair follicles, comprising an amino acid sequence having at least 95% sequence identity to amino acid residues 239–391 of SEQ ID NO 2.

5. The purified protein of claim 4, wherein the amino acid sequence has at least 98% sequence identity to amino acid residues 239–391 of SEQ ID NO 2.

6. A purified protein that promotes the development of hair follicles, comprising an amino acid sequence having at least 95% sequence identity to an amino acid sequence shown in SEQ ID NO 2.

7. The purified protein of claim 4, wherein the amino acid sequence has at least 98% sequence identity to the amino acid sequence shown in SEQ ID NO 2.

8. A purified protein that promotes the development of hair follicles, comprising an amino acid sequence shown as amino acid residues 239–391 of SEQ ID NO 2.

9. A purified protein that promotes the development of hair follicles, comprising the amino acid sequence shown in SEQ ID NO 2.

10. A purified protein that promotes the development of hair follicles, comprising an amino acid sequence having at least 80% sequence identity to amino acid residues 25–151 of SEQ ID NO 17.

11. The purified protein of claim 10, wherein the amino acid sequence comprises amino acid residues 25–151 of SEQ ID NO 17.

12. A purified protein that promotes the development of hair follicles, comprising an amino acid sequence having at least 80% sequence identity to an amino acid sequence shown in SEQ ID NO 17.

13. The purified protein of claim 12, wherein the amino acid sequence comprises the amino acid sequence shown in SEQ ID NO 17.

14. A purified protein that promotes the development of hair follicles, comprising an amino acid sequence having at least 80% sequence identity to an amino acid sequence shown SEQ ID NO 19.

15. The purified protein of claim 14, wherein the amino acid sequence comprises the amino acid sequence shown in SEQ ID NO 19.

16. A purified protein that promotes the development of hair follicles, comprising an amino acid sequence having at least 80% sequence identity to an amino acid sequence that differs from SEQ ID NO 17 by one or more conservative amino acid substitutions.

17. The purified protein of claim 16, wherein the amino acid sequence comprises an amino acid sequence that differs from SEQ ID NO 17 by one or more conservative amino acid substitutions.

18. A purified protein that promotes the development of hair follicles, comprising an amino acid sequence having at least 80% sequence identity to an amino acid sequence that differs from SEQ ID NO 19 by one or more conservative amino acid substitutions.

19. The purified protein of claim 18, wherein the amino acid sequence comprises an amino acid sequence that differs from SEQ ID NO 19 by one or more conservative amino acid substitutions.

* * * * *

UNITED STATES PATENT AND TRADEMARK OFFICE
CERTIFICATE OF CORRECTION

| | |
|---|---|
| PATENT NO. | : 6,355,782 B1 |
| APPLICATION NO. | : 09/342681 |
| DATED | : March 12, 2002 |
| INVENTOR(S) | : Zonana et al. |

It is certified that error appears in the above-identified patent and that said Letters Patent is hereby corrected as shown below:

<u>In the Specification:</u>

Column 5, line 39-40 (specification page 8, line 9), "EDA1-II, or DL" should be --EDA1-II, dl, or DL--.

Column 5, lines 62, "EDAL" should be --EDA1--.

Column 11, line 49, both instances of "C." should be --C--.

Column 14, lines 9-10, each instance of "C." should be --C--.

Column 14, lines 31-32, both instances of "C." should be --C--.

Column 17, line 52, "finction" should be --function--.

Column 18, line 52, "finction" should be --function--.

Column 20, line 43, "fmgerprinting" should be --fingerprinting--.

Column 22, line 44, "C." should be --C--.

Column 22, lines 61-62, each instance of "C." should be --C--.

Column 23, lines 17, 25-26, 48-49, and 61-63, each instance of "C." should be --C--.

UNITED STATES PATENT AND TRADEMARK OFFICE
CERTIFICATE OF CORRECTION

PATENT NO.      : 6,355,782 B1
APPLICATION NO. : 09/342681
DATED           : March 12, 2002
INVENTOR(S)     : Zonana et al.

It is certified that error appears in the above-identified patent and that said Letters Patent is hereby corrected as shown below:

Column 24, lines 7-8, 33, 35, and 66, each instance of "C." should be --C--.

Column 25, line 1, "C." should be --C--.

Column 26, line 11, "sldn" should be --skin--.

Column 27, line 50, "(1 7-24 week EGA)" should be --(17-24 week EGA)--.

Column 28, line 21, "intronlexon" should be --intron/exon--.

Column 29, lines 13-16, each instance of "C." should be --C--.

Column 29, line 20, "Exons 7/18-HindII" should be --Exons 7/8-HindII--.

Columns 33-34, in the fourth line of IVS 6 (SINE-MIR repeat - 104 bp - italicized) (Seq. I.D. No. 103), "M" should be --AA--, so that the sequence listing reads as follows:

--IVS 6 (SINE-MIR repeat - 104bp - italicized) (Seq. I.D. No. 103)

GTGAGTGTCTTTGTCCTTCCACCAGCACGGTATTTGTTCAGGCACGGATCTCTTTCACTACAGAGGG
TGTAGGAAAGAGCCGGTCCTGGCACCTGGACAAGGTGAATCACAGTAACAGCACTAGTGAAAGTGCT
CCTGTGGCCTGTCCAGGCAGGTCTATGAAGGGAGGGGCGTTTGCCACATCTGAGCCTTGAGTCAGAG
GCTGAGGTTCTAGTGCAGGTTGGCCACCAGCTACCTGACAAGTCACTTAACCTCCATGAGCCTCGGT
TTTCTCATCGGTAATATGGGGGTGA...AGAAAGNACAATANCGATGACTCTTTAGGGTTCATTAAA
CAGTCTAAGAAATACAAATATTTAGCTCCCCTCAGCCATCACTGCCTCAGGCCCATTCATGATCATG
AATCCAGATCCATGAGCTCTGTGGCAGCGTGCTTTGAAGGTGGAGCTTCTCTGGATCATTTGAGGGA
CTCTATTTTGCCTTGCAG--.

UNITED STATES PATENT AND TRADEMARK OFFICE
CERTIFICATE OF CORRECTION

PATENT NO. : 6,355,782 B1
APPLICATION NO. : 09/342681
DATED : March 12, 2002
INVENTOR(S) : Zonana et al.

It is certified that error appears in the above-identified patent and that said Letters Patent is hereby corrected as shown below:

Column 37, in the 12th line of Exon 12 (3' UTR underlined) (Seq. I.D. No. 116), "CTTAA" should be --CGTTAA--, and in Column 39, the last line of Exon 12 (3' UTR underlined) (Seq. I.D. No. 116), the string of 25 "A"s "AAAAAAAAAAAAAAAAAAAAAAAAA" should be a string of 24 "A"s --AAAAAAAAAAAAAAAAAAAAAAAA-- so that Seq. 1.D. No. 116 reads as follows:

-- Exon 12 (3' UTR underlined) (seq. I.D. No. 116)

```
GTCTTAGCCCCACGGAGCTGCCATTTGATTGCCTCGAGAAGACTAGCCGAATGCTCAGCTCCACGTA
CAACTCTGAGAAGGCTGTTGTGaAAACGTGGCGCCaCCTCGCCGAGAGCTTCGGCCTGAAGAGGGAT
GAGATTGGGGGCATGACAGACGGCATGCAACTCTTTGACCGCATCAGCACGGCAGGCTACAGCATCC
CTGAGCTACTCACAAAACTGGTGCAGATTGAGCGGCTGGATGCTGTGGAGTCCTTGTGTGCAGACAT
ACTGGAGTGGGCGGGGGTTGTGCCACCTGCCTCCCAGCCACATGCTGCATCCTGA
AAAGCATGCCTGTGGGCTGTCCTCCCAgGACAAGCCAAGGATCCAACGAGGGCTCTGGAGCTGTGAG
TGGTGCCAAAAGACTGCCAAGAATCaGGCTTTTGTGATATGTCACCGTATGCCTTAGGATGTTCAA
GGAGCCAGACGAAATAAGGCCTGTCTTCCAATTTAACCAAAGATAAAGGACTAGAGCCGGGATACTT
TCANATGCTCGCCTGTACCTCACCAGGCAGAGTAAATATCTACTCACTCATACAGCCAGCCCACCAG
CCCACCATTAACTCACTGAACAATGAGACAATGTNGAGGACTCAAATGAATCAAACCCCGTGGGAAT
GACAGANTGAAGAATCTGGTCCCTGTCTTTAAGGAGTTTGCACTCCAGTAGAAGCAGAAGGAACGT
ATGTTTACAAAGCACTTCACTGGAAGACGTCAAACAAGCTGAATGAAGGGGCGCTTAGAAAACGTTA
ATAGAAGTTCTAAGCGGGAGATGACTCCCTACTGGGATGATGAAGGATGGCATCCTAGTGAAGAAGC
AGCTCAAACATTTTGATAAAATGGCAACAAAATGCAGACACCCTGCTCCAGGTATTATTTCAGGTTT
AGTACAAGTCTGTTAATACCCTATGTGGTTTCATTAGGATAACTTTTTACCTATCCTTGAGGTCATC
CATATTCTTACAGGCCTTCCAGTCAATAATGGAAGAGCTCACTCTATACAAAACCAATATGCAAGGC
ATGTGTTTGTCCAAGCAATTGGATGTGTGCAGTAGCCAATTTCATTTACTGCATTACTCTTTGGCCT
GGGAACCCTGTGGTCTGCACTACATGTGAATGGCCTTCCACTTCAAGTCTTAGGCAGATTTGACCTT
TTAGGGGCAGCAATGCTGAAGGACACAGCAATTTAAATTATAATGTGTCAGGCTGTGTTTTCACTTC
AAACATGTATGAGTAGTCAGCTGTAATTAGAGAAATGATGACTTCCTAAGAGTTCAGCCACGCATAA
TTCTAGATTTCAAGAGCATCTAAGACTTGTGGATTAGCCTCATGGCATGAGAGTTTCAGACTCAGCC
TTCTGAGCCAGTCAGGGAAAGTGGAGTTCTGCAGCGCAAATGAGAGCCTGGGCTTGGTGCGAGGGA
GCTGGCTTCTAGTTGTGCCACCTTGGGCCTTGTCTTTTCCTCTCTCTGCCTCAGTTTCTCGTCTGCC
AATGAGATGTTAGTTAGTGATTCTATAATTGGGGCAGGTAGGGTTCAGGTGAGCAAAAAGAAAGTGG
AGCTATAGGAAATGCCAGGCCTTTGAGGTGCTCTATGGAAGTCAACACAGTGTGGTTTGTCCATTTA
AATGGGAATAAAAACAGAAAAACTCAGACTTGGCATTTTCACAATAACTGCAATGGTTTGACATAAC
ATTTATAGGCAGAAAGTTAATAAACTGGCATTGTTCTTGGCATATTATTGTACTATCCCTGTAACTG
CCAAGAGCTCAGGAGCCAGGCTAGTGATCACACCAGGGGTTAGAGTTCACTGCTGAACTCCCTGATG
GCAGGTCTGTGTTTATTACTACATTAAAACAAAGTCTCTGACTTATAAAGCGAGGTCGTAAAAATTA
CAAGTTGCATGACTGAAAAAATGCTTTAGGGGGAAAATCAGTCATATCTTTAACACCAACAAGCAAT
TTCCCACCAACGAATGTAGTACATACTGTGAGAGGATCATAATGAGGTCCTGAATATTTAATATCAT
CATTTACTGTGTCTGTTTGCTGCTGTTTTTCGAACCTATTTGGTTTACCCTGCAAGCTAAATACTCC
ACGGCAGANCTTAATTATCCTTTTAATTCCTCTTTGAAATCCTGTGGTGCCCCCTTCCCCCTGCCTT
GTGATGATGATGAGTGAGTCTCCCCTTAATTAGACTGCAAATGTCACTTGTGATGAGTGTGCCATTC
CAGGATAACAGCTTGCACCCTCCTCAGAATGTTTTCAGCGAAAGAGTGGGGTGGCTGTTCTCTGCTC
CTGGTGCTTTGGCCTCATTTCACACTATTAGAATTCTGGGGCTGTAAGGCCAGCCAGTGTCAGCTCA
TGTTCCATTGGCTCTCCACCTGCCATTTTTAGGGAGCTATTCCTTATATAGTTACAAATTCCCTTGT
CATTTACTTATTTGGAAACATGGGATTTACTCTGACAAGCTTTAGCCTATGTTATGGGATTCAGAAC
AATGAGATCATAATAATTCTCACTGACCAAAGCTGGGACTCCATCCTGCCATTTTTGTGTGGAGATA
TTCATAATTCTGCAATACTTTAAAACATTTAGAAAACACCCCAGGGTAGGTCTGTGGCCCTTANACA
GTGAAAGTCTTAATTGGCAATATTATTTTTGCTAATTCTGGATATATATAACNNATTATATTTATAA
ATCTCAATAAACCCCATTTANTAAAAAAAAAAAAAAAAAAAAAAAA--.
```

UNITED STATES PATENT AND TRADEMARK OFFICE
CERTIFICATE OF CORRECTION

PATENT NO. : 6,355,782 B1
APPLICATION NO. : 09/342681
DATED : March 12, 2002
INVENTOR(S) : Zonana et al.

It is certified that error appears in the above-identified patent and that said Letters Patent is hereby corrected as shown below:

Column 39, line 29, "famifies" should be --families--.

Column 55, line 25, "$C_1$–$C_6$" should be --$C_1$–$C_{16}$--.

Column 59, line 49, "Caberra" should be --Canberra--.

Column 62, line 5, "*Phann Res*" should be --*Pharm Res*--.

Column 62, line 43, "i Mol. Cell Biol." should be --*Mol. Cell Biol.* --.

Signed and Sealed this

Twenty-eighth Day of November, 2006

JON W. DUDAS
*Director of the United States Patent and Trademark Office*